(12) United States Patent
Koehler et al.

(10) Patent No.: US 10,758,513 B2
(45) Date of Patent: Sep. 1, 2020

(54) MODULATORS OF MITOCHONDRIAL PROTEIN IMPORT

(71) Applicant: THE REGENTS OF THE UNIVERSITY OF CALIFORNIA, Oakland, CA (US)

(72) Inventors: Carla M. Koehler, Los Angeles, CA (US); Samuel A. Hasson, Portland, OR (US); Kiyoko Miyata, Los Angeles, CA (US); Michael A. Teitell, Tarzana, CA (US); Deepa Dabir, Redondo Beach, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/815,565

(22) Filed: Nov. 16, 2017

(65) Prior Publication Data
US 2018/0221330 A1   Aug. 9, 2018

Related U.S. Application Data

(63) Continuation of application No. 14/111,265, filed as application No. PCT/US2012/033279 on Apr. 12, 2012, now abandoned.

(60) Provisional application No. 61/474,724, filed on Apr. 12, 2011.

(51) Int. Cl.
| | |
|---|---|
| *A61K 31/343* | (2006.01) |
| *A61K 31/137* | (2006.01) |
| *A61K 31/15* | (2006.01) |
| *A61K 31/404* | (2006.01) |
| *A61K 31/4196* | (2006.01) |
| *C12Q 1/02* | (2006.01) |
| *C12Q 1/18* | (2006.01) |
| *G01N 33/50* | (2006.01) |

(52) U.S. Cl.
CPC .......... *A61K 31/343* (2013.01); *A61K 31/137* (2013.01); *A61K 31/15* (2013.01); *A61K 31/404* (2013.01); *A61K 31/4196* (2013.01); *C12Q 1/025* (2013.01); *C12Q 1/18* (2013.01); *G01N 33/5079* (2013.01)

(58) Field of Classification Search
CPC .................................................. A61K 31/343
See application file for complete search history.

(56) References Cited

PUBLICATIONS

Banci, L., et al., Molecular recognition and substrate mimicry drive the electron-transfer process between MIA40 and ALR. Proc Natl Acad Sci U S A 108, 4811-4816 (2011).

Beverly et al., The Tim8-Tim13 complex has multiple substrate binding sites and binds cooperatively to Tim23. J Mol Biol 382:1144-1156 (2008).

Bernardi, P., and Azzone, G.F. Cytochrome c as an electron shuttle between the outer and inner mitochondrial membranes. J Biol Chem 256, 7187-7192 (1981).

Bihlmaier, K. et al., The disulfide relay system of mitochondria is connected to the respiratory chain. J Cell Biol 179, 389-395 (2007).

Brandner et al., Taz1, an outer mitochondrial membrane protein, affects stability and assembly of inner membrane protein complexes: implications for Barth Syndrome. Mol Biol Cell 16:5202-5214 (2005).

Cassidy-Stone, A. et al., Chemical inhibition of the mitochondrial division dynamin reveals its role in Bax/Bak-dependent mitochondrial outer membrane permeabilization. Dev Cell 14, 193-204 (2008).

Castellano, S. et al., Small-molecule inhibitors of protein geranylgeranyltransferase type I. J Am Chem Soc 129, 5843-5845 (2007).

Cavallaro, G. (Abstract) Genome-wide analysis of eukaryotic twin CX9C proteins. Mol Biosyst 6, 2459-2470 (2010).

Chacinska et al. Importing mitochondrial proteins: machineries and mechanisms. Cell 138:628-644 (2009).

Chacinska, A. et al., Mitochondrial biogenesis, switching the sorting pathway of the intermembrane space receptor Mia40. J Biol Chem 283, 29723-29729 (2008).

Chacinska, A., Essential role of Mia40 in import and assembly of mitochondrial intermembrane space proteins. EMBO J 23, 3735-3746 (2004).

Claypool et al., Mitochondrial mislocalization and altered assembly of a cluster of Barth syndrome mutant tafazzins. J Cell Biol 174:379-390 (2006).

Claypool et al., Cardiolipin defines the interactome of the major ADP/ATP carrier protein of the mitochondrial inner membrane. J Cell Biol 182:937-950 (2008).

Claypool, S.M. et al., The cardiolipin transacylase, tafazzin, associates with two distinct respiratory components providing insight into Barth syndrome. Mol Biol Cell 19, 5143-5155 (2008).

Crugeiras, J. et al., Substituent effects on the thermodynamic stability of imines formed from glycine and aromatic aldehydes: implications for the catalytic activity of pyridoxal-5'-phosphate. J Am Chem Soc 131, 15815-15824 (2009).

Curado, S. et al., The mitochondrial import gene tomm22 is specifically required for hepatocyte survival and provides a liver regeneration model. Dis Model Mech 3, 486-495 (2010).

Curran et al. The Tim9p-Tim10p complex binds to the transmembrane domains of the ADP-ATP carrier. EMBO J. 21:942-953 (2002).

Curran et al. The role of the Tim8p-Tim13p complex in a conserved import pathway for mitochondrial polytopic inner membrane proteins. J Cell Biol 158:1017-1027 (2002).

(Continued)

*Primary Examiner* — Kortney L. Klinkel
*Assistant Examiner* — Tori Strong
(74) *Attorney, Agent, or Firm* — Morgan, Lewis & Bockius LLP; Jeffry S. Mann; Louis T. Nguyen

(57) ABSTRACT

The present invention provides compounds that modulate protein translocation in mitochondria, compositions thereof, and methods of identifying, making and using these.

10 Claims, 26 Drawing Sheets

(56) References Cited

PUBLICATIONS

Dabir, D.V., et al., A role for cytochrome c and cytochrome c peroxidase in electron shuttling from Erv1. EMBO J 26, 4801-4811 (2007).
Daithankar, V.N. et al., Structure of the human sulfhydryl oxidase augmenter of liver regeneration and characterization of a human mutation causing an autosomal recessive myopathy. Biochemistry 49, 6737-6745 (2010).
Davis et al., Two intermembrane space TIM complexes interact with different domains of Tim23p during its import into mitochondria. J Cell Biol 150:1271-1282 (2000).
Davis et al., The Tim9p/10p and Tim8p/13p complexes bind to specific sites on Tim23p during mitochondrial protein import. Mol Biol Cell 18:475-486 (2007).
Deponte, M., and Hell, K. (Abstract) Disulphide bond formation in the intermembrane space of mitochondria. J Biochem 146, 599-608 (2009).
Devi et al., Accumulation of amyloid precursor protein in the mitochondrial import channels of human Alzheimer's disease brain is associated with mitochondrial dysfunction. J Neurosci 26:9057-9068 (2006).
Di Fonzo, A. et al. The mitochondrial disulfide relay system protein GFER is mutated in autosomal-recessive myopathy with cataract and combined respiratory-chain deficiency. Am J Hum Genet 84, 594-604. (2009).
Duncan et al., Composite synthetic lethal identification of membrane traffic inhibitors. Proc Natl Acad Sci U S A 104:6235-6240 (2007).
Doorn, J.A., and Petersen, D.R. Covalent adduction of nucleophilic amino acids by 4-hydroxynonenal and 4-oxononenal. Chem Biol Interact 143-144, 93-100 (2003).
Emaus RK, Grunwald R, Lemasters JJ, Rhodamine 123 as a probe of transmembrane potential in isolated rat-liver mitochondria: spectral and metabolic properties. Biochim Biophys Acta 850:436-448 (1986).
Farrell, S.R., and Thorpe, C. Augmenter of liver regeneration: a flavin-dependent sulfhydryl oxidase with cytochrome c reductase activity. Biochemistry 44, 1532-1541 (2005).
Gerber, J. et al., Yeast ERV2p is the first microsomal FAD-linked sulfhydryl oxidase of the Erv1p/Alrp protein family. J Biol Chem 276, 23486-23491 (2001).
Glick, B.S., and Pon, L.A. Isolation of highly purified mitochondria from *Saccharomyces cerevisiae*. Methods Enzymol 260, 213-223. (1995).
Goyon V, et al., Yeast cells depleted in Atp14p fail to assemble Atp6p within the ATP synthase and exhibit altered mitochondrial cristae morphology. J Biol Chem 283:9749-9758 (2008).
Gross, E. et al., A new FAD-binding fold and intersubunit disulfide shuttle in the thiol oxidase Erv2p. Nat Struct Biol 9, 61-67 (2002).
Gueldener et al., A second set of loxP marker cassettes for Cre-mediated multiple gene knockouts in budding yeast. Nucleic Acids Res 30 (2002).
Guldener et al., A new efficient gene disruption cassette for repeated use in budding yeast. Nucleic Acids Res 24:2519-2524 (1996).
Guthrie C, Fink GR Guide to yeast genetics and molecular biology (Academic Press, San Diego, CA) (1991).
Hansson Petersen et al., The amyloid beta-peptide is imported into mitochondria via the TOM import machinery and localized to mitochondrial cristae. Proc Natl Acad Sci U S A 105:13145-13150 (2008).
Hasson, S. et al., Substrate specificity of the TIM22 mitochondrial import pathway revealed with small molecule inhibitor of protein translocation. PNAS, 107, 21: pp. 9578-9583 (2010).
Herrmann, J.M., and Hell, K. Chopped, trapped or tacked-protein translocation into the IMS of mitochondria. Trends Biochem Sci 30, 205-211 (2005).
Hofmann, S. et al., Functional and mutational characterization of human MIA40 acting during import into the mitochondrial intermembrane space. J Mol Biol 353, 517-528 (2005).
Hoppins and Nargang, The Tim8-Tim13 complex of Neurospora crassa functions in the assembly of proteins into both mitochondrial membranes. J. Biol. Chem. 279:12396-12405 (2004).
Horn, D., Al-Ali, H., and Barrientos, A. Cmc1p is a conserved mitochondrial twin CX9C protein involved in cytochrome c oxidase biogenesis. Mol Cell Biol 28, 4354-4364 (2008).
Ivanova, N.B., et al., A stem cell molecular signature. Science 298, 601-604 (2002).
Jin H, et al. A novel X-linked gene, DDP, shows mutations in families with deafness (DFN-1), dystonia, mental deficiency and blindness. Nat Genet 14:177-180 (1996).
Kirdant, A.S. et al., Kinetic study of hydrolysis of N-salicylidene-m-methyl aniline spectrophotometrically. J Chem Pharm Res 3, 790-796 (2011).
Koehler et al., Tim9p, an essential partner subunit of Tim10p for the import of mitochondrial carrier proteins. EMBO J 17:6477-6486 (1998).
Koehler CM, et al. Import of mitochondrial carriers mediated by essential proteins of the intermembrane space. Science 279:369-373 (1998).
Koehler et al., Human deafness dystonia syndrome is a mitochondrial disease. Proc Natl Acad Sci U S A 96:2141-2146 (1999).
Koehler CM, Merchant S, Schatz G., How membrane proteins travel across the mitochondrial intermembrane space. Trends Biochem Sci 24:428-432 (1999).
Koehler CM, Beverly KN, Leverich EP, Redox pathways of the mitochondrion. Antioxid Redox Signal 8:813-822 (2006).
Lange, H. et al., An essential function of the mitochondrial sulfhydryl oxidase Erv1p/ALR in the maturation of cytosolic Fe/S proteins. EMBO Rep 2, 715-720 (2001).
Leuenberger et al., Different import pathways through the mitochondrial intermembrane space for inner membrane proteins. EMBO J 17:4816-4822 (1999).
Leuenberger et al. The Role of Tim9p in the Assembly of the TIM22 Import Complexes. Traffic 4:144-152 (2003).
Lumsden, A.L. et al., Huntingtin-deficient zebrafish exhibit defects in iron utilization and development. Hum Mol Genet 16, 1905-1920 (2007).
Mendelsohn, B.A. et al., Atp7a determines a hierarchy of copper metabolism essential for notochord development. Cell Metab 4, 155-162 (2006).
Mills RD, et al., Biochemical aspects of the neuroprotective mechanism of PTEN-induced kinase-1 (PINK1). J Neurochem 105:18-33 (2008).
Milenkovic, D. et al., Identification of the signal directing Tim9 and Tim10 into the intermembrane space of mitochondria. Mol Biol Cell 20, 2530-2539 (2009).
Mochizuki, Y., and Furukawa, K. Application of coomassie brilliant blue staining to cultured hepatocytes. Cell Biol Int Rep 11, 367-371 (1987).
Mokranjac, D., and Neupert, W. Thirty years of protein translocation into mitochondria: unexpectedly complex and still puzzling. Biochim Biophys Acta 1793, 33-41 (2009).
Murphey, R.D., and Zon, L.I. Small molecule screening in the zebrafish. Methods 39, 255-261 (2006).
Murphy et al., The essential function of the small Tim proteins in the TIM22 import pathway does not depend on formation of the soluble 70-kilodalton complex. Mol Cell Biol 21:6132-6138 (2001).
Nordfelth, R. et al., Small-molecule inhibitors specifically targeting type III secretion. Infect Immun 73, 3104-3114 (2005).
Parone, P.A., et al., Inhibiting the mitochondrial fission machinery does not prevent Bax/Bak-dependent apoptosis. Mol Cell Biol 26, 7397-7408 (2006).
Ramalho-Santos, M. et al., "Sternness": transcriptional profiling of embryonic and adult stem cells. Science 298, 597-600 (2002).
Riemer, J., et al., Oxidation-driven protein import into mitochondria: Insights and blind spots. Biochim Biophys Acta 1808, 981-989 (2011).
Roesch et al., The calcium-binding aspartate/glutamate carriers, citrin and aralar1, are new substrates for the DDP1/TIMM8a-TIMM13 complex. Hum. Mol. Genet. 13:2101-2111 (2004).

(56) References Cited

PUBLICATIONS

Ryan et al., Functional Staging of ADP/ATP Carrier Translocation across the Outer Mitochondrial Membrane. J. Biol. Chem. 274:20619-20627 (1999).

Schiestl RH, Manivasakam P, Woods RA, Gietz RD Introducing DNA into Yeast by Transformation. Methods 5:79-85 (1993).

Schmidt, O., Pfanner, N., and Meisinger, C. (2010). Mitochondrial protein import: from proteomics to functional mechanisms. Nat Rev Mol Cell Biol 11, 655-667.

Scorrano, L. et al., A distinct pathway remodels mitochondrial cristae and mobilizes cytochrome c during apoptosis. Dev Cell 2, 55-67 (2002).

Senkevich, T.G. et al., Complete pathway for protein disulfide bond formation encoded by poxviruses. Proc Natl Acad Sci U S A 99, 6667-6672 (2002).

Shamblott, M.J. et al., Derivation of pluripotent stem cells from cultured human primordial germ cells. Proc Natl Acad Sci U S A 95, 13726-13731 (1998).

Shaw, G.C. et al., Mitoferrin is essential for erythroid iron assimilation. Nature 440, 96-100 (2006).

Shu, X., et al., Na,K-ATPase alpha2 and Ncx4a regulate zebrafish left-right patterning. Development 134, 1921-1930 (2007).

Sideris, D.P. et al., A novel intermembrane space-targeting signal docks cysteines onto Mia40 during mitochondrial oxidative folding. J Cell Biol 187, 1007-1022 (2009).

Sideris, D.P., and Tokatlidis, K. Oxidative protein folding in the mitochondrial intermembrane space. Antioxid Redox Signal 13, 1189-1204 (2010).

Sikorski and Hieter, A system of shuttle vectors and yeast host strains designed for efficient manipulation of DNA in *Saccharomyces cerevisiae*. Genetics 122:19-27 (1989).

Silvestri L, et al., Mitochondrial import and enzymatic activity of PINK1 mutants associated to recessive parkinsonism. Hum Mol Genet 14:3477-3492 (2005).

Stojanovski, D. et al., Mitochondrial protein import: precursor oxidation in a ternary complex with disulfide carrier and sulfhydryl oxidase. J Cell Biol 183, 195-202 (2008).

Stojanovski, D., Muller et al.,The MIA system for protein import into the mitochondrial intermembrane space. Biochim Biophys Acta 1783, 610-617 (2008).

Terziyska, N., et al., The sulfhydryl oxidase Erv1 is a substrate of the Mia40-dependent protein translocation pathway. FEBS Lett 581, 1098-1102 (2007).

Terziyska, N., et al., Structural and functional roles of the conserved cysteine residues of the redox-regulated import receptor Mia40 in the intermembrane space of mitochondria. J Biol Chem 284, 1353-1363 (2009).

Thorpe, C. et al., Sulfhydryl oxidases: emerging catalysts of protein disulfide bond formation in eukaryotes. Arch Biochem Biophys 405, 1-12 (2002).

Tienson, H.L. et al., Reconstitution of the Mia40-Erv1 oxidative folding pathway for the small tim proteins. Mol Biol Cell 20, 3481-3490 (2009).

Todd, L.R., et al., Growth factor erv1-like modulates Drp1 to preserve mitochondrial dynamics and function in mouse embryonic stem cells. Mol Biol Cell 21, 1225-1236 (2010).

Todd, L.R., et al. A novel Gfer-Drp1 link in preserving mitochondrial dynamics and function in pluripotent stem cells. Autophagy 6, 821-822 (2010).

Truscott, K.N. et al., Mitochondrial import of the ADP/ATP carrier: the essential TIM complex of the intermembrane space is required for precursor release from the TOM complex. Mol Cell Biol 22, 7780-7789 (2002).

Vitu, E. et al., Gain of function in an ERV/ALR sulfhydryl oxidase by molecular engineering of the shuttle disulfide. J Mol Biol 362, 89-101 (2006).

Webb et al. Crystal structure of the mitochondrial chaperone TIM9. 10 reveals a six-bladed alpha-propeller. Mol Cell 21:123-133 (2006).

Wiedemann et al., Biogenesis of the protein import channel Tom40 of the mitochondrial outer membrane: intermembrane space components are involved in an early stage of the assembly pathway. J. Biol. Chem. 279:18188-18194 (2004).

Wingert, R.A. et al., Deficiency of glutaredoxin 5 reveals Fe-S clusters are required for vertebrate haem synthesis. Nature 436, 1035-1039 (2005).

Wu, C.K. et al., The crystal structure of augmenter of liver regeneration: A mammalian FAD-dependent sulfhydryl oxidase. Protein Sci 12, 1109-1118 (2003).

Zhang, J. et al., UCP2 regulates energy metabolism and differentiation potential of human pluripotent stem cells. EMBO J 30, 4860-4873 (2011).

Curran et al., The Role of Hot13p and Redox Chemistry in the Mitochondrial TIM22 Import Pathway, JBC, 279: 42, pp. 43744-43751 (2004).

Herndon, J. et al., The Tazlp Transacylase is Imported and Sorted into the Outer Mitochondrial Membrane via a Membrane Anchor Domain. Eukaryotic Cell, 12: 12, pp. 1600-1608 (2013).

Figure 2
2A
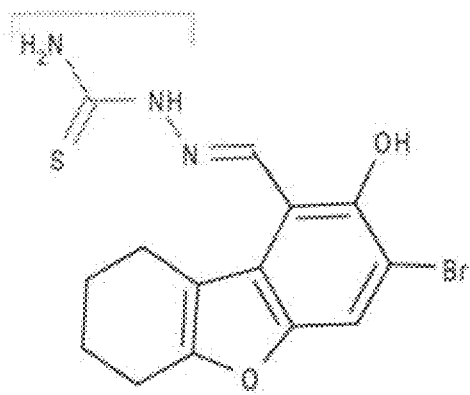
2B
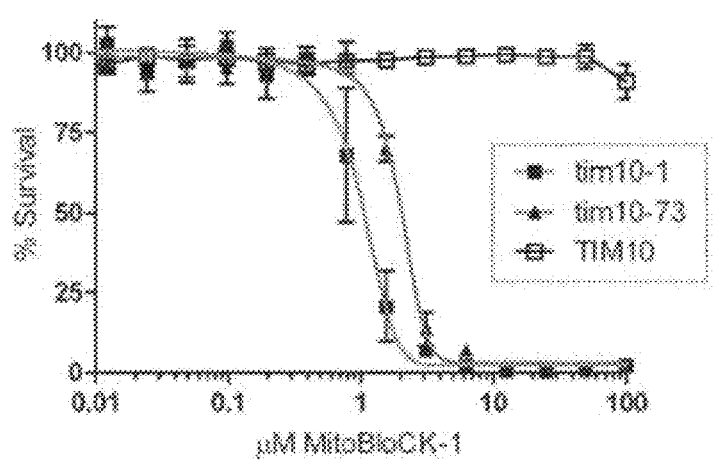

Figure 3
3A 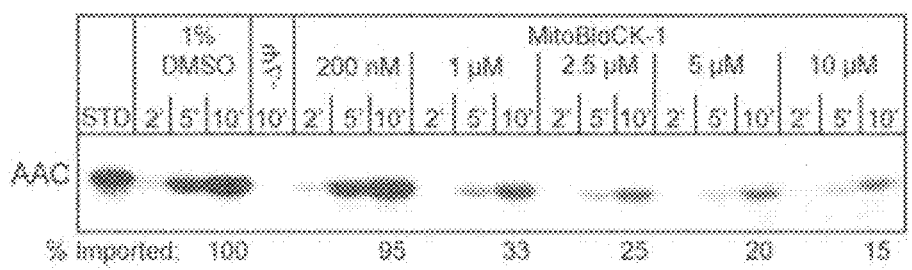
3B 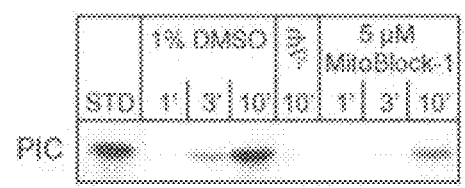
3C 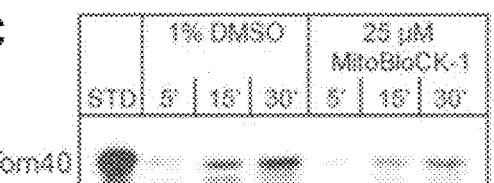
3D 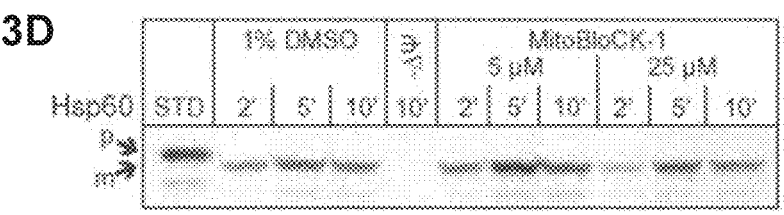

Figure 5
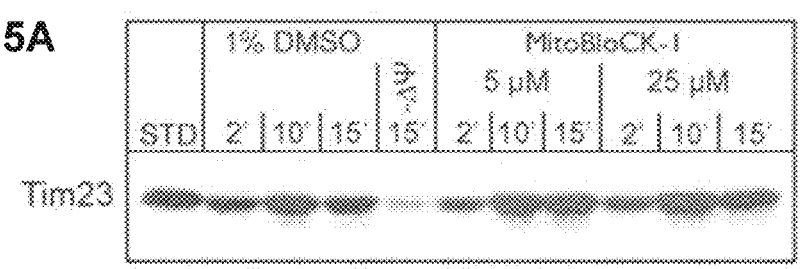
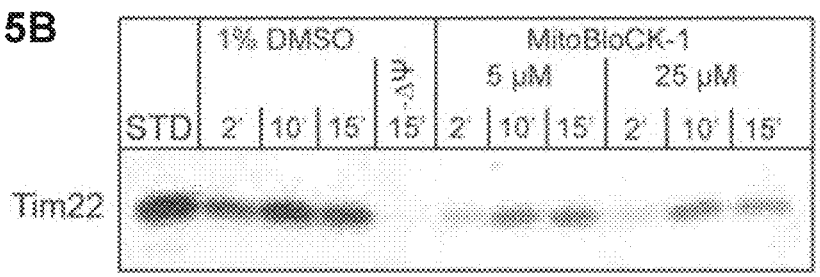
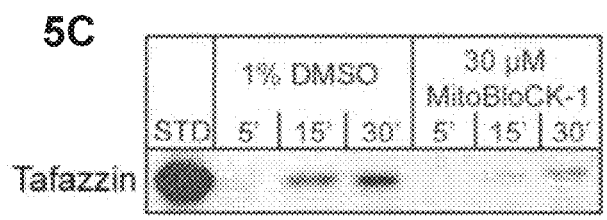

Figure 6
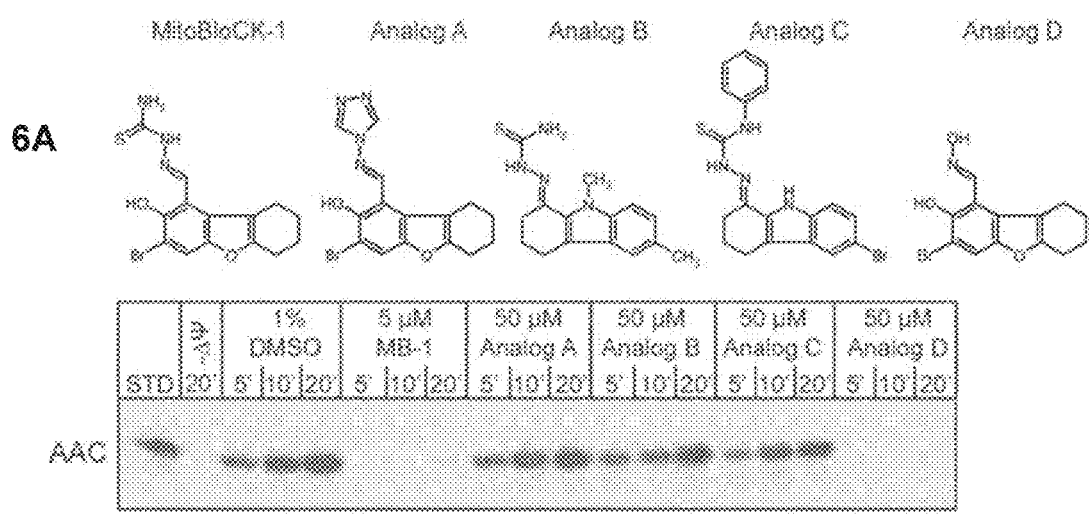
6A
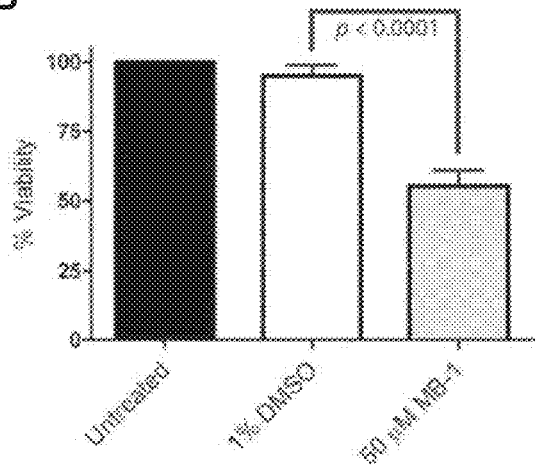
6B
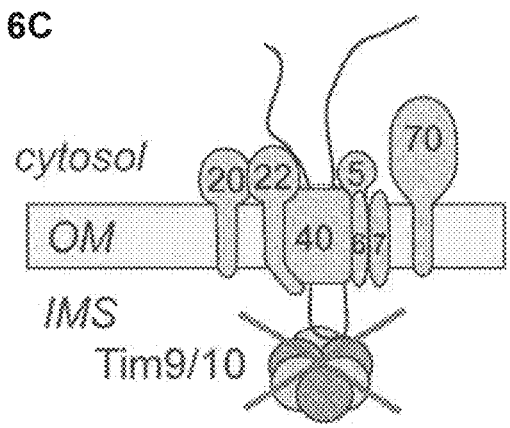
6C

Figure 7
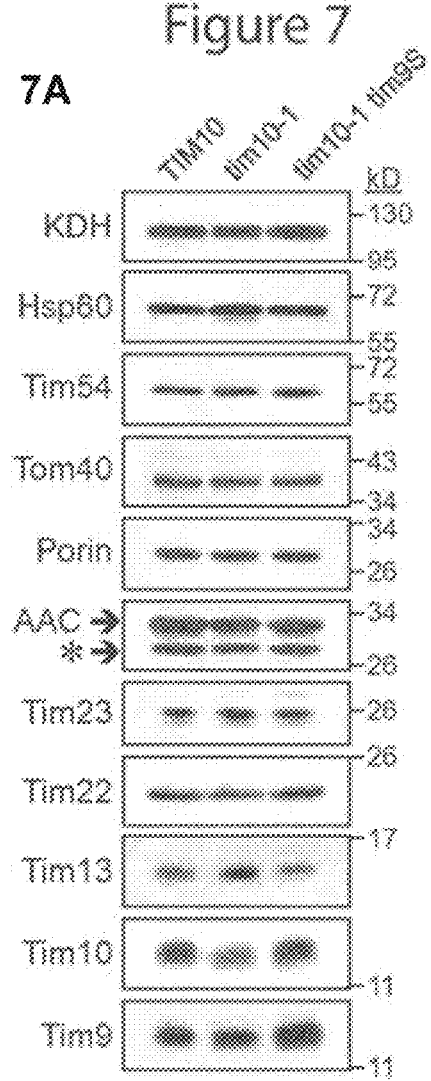
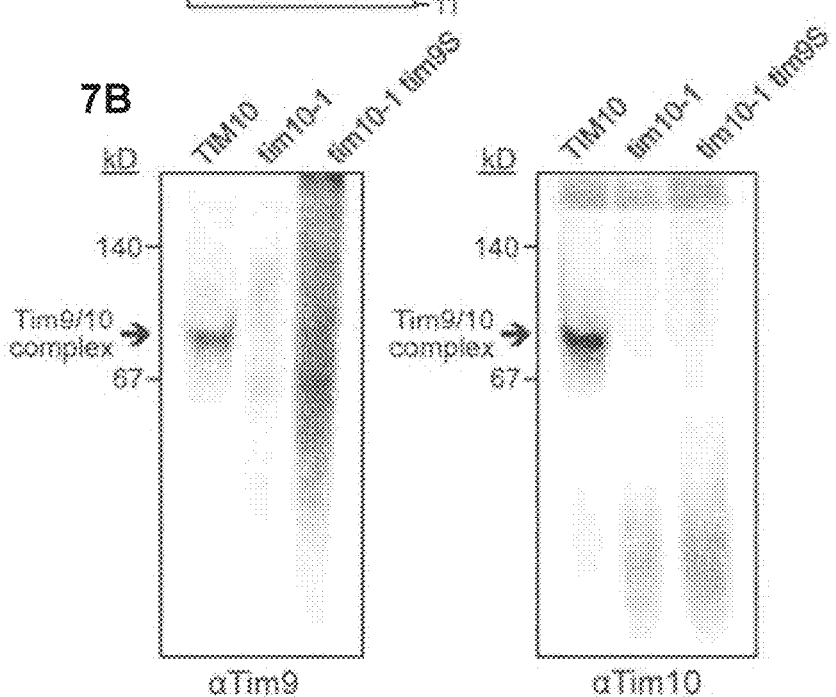

Figure 10
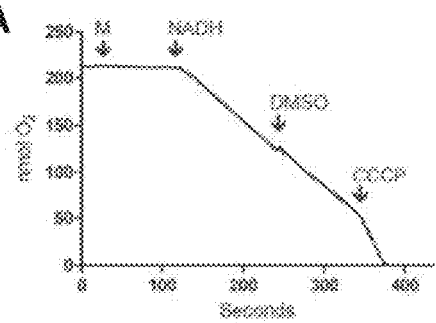
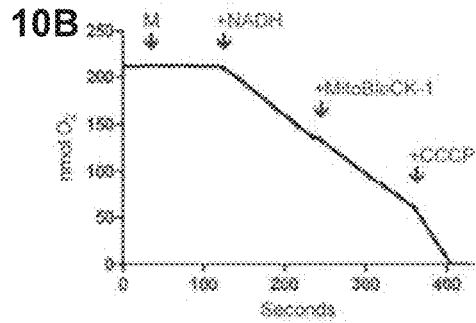
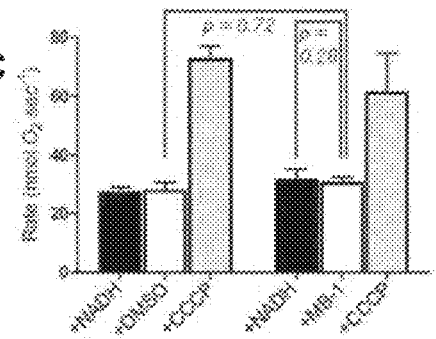
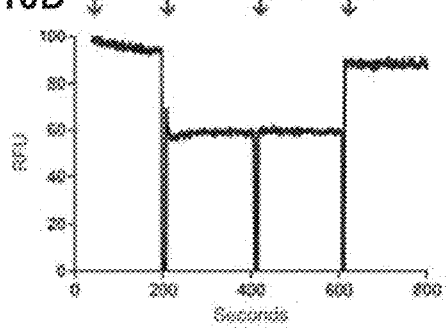
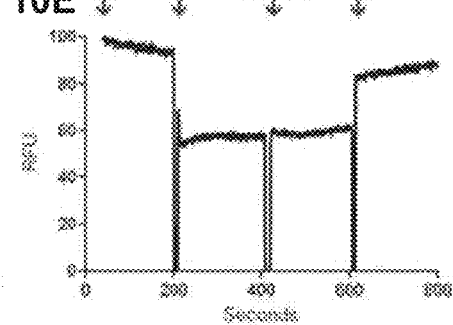
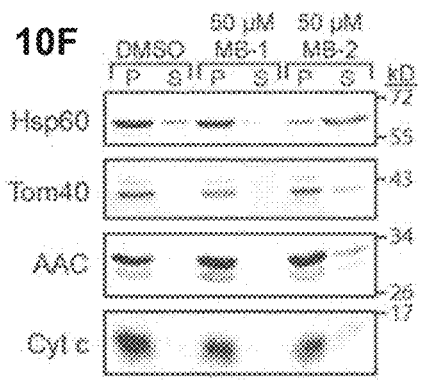
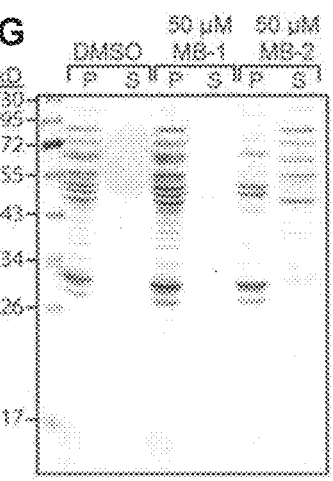
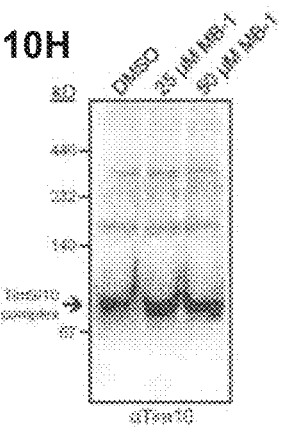

Figure 11
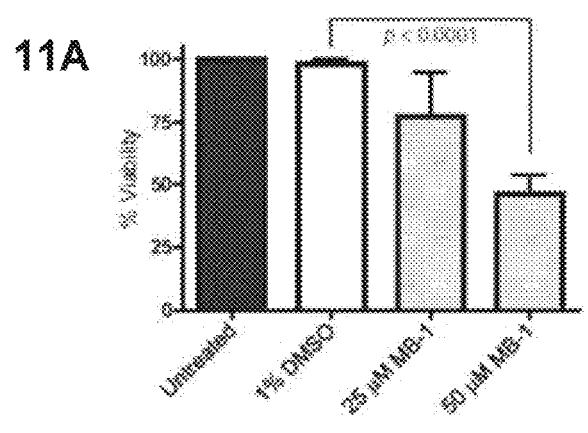
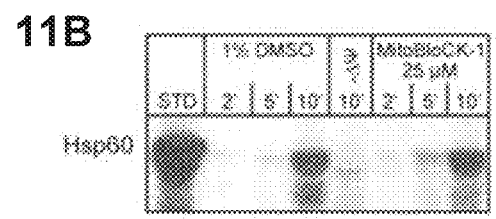
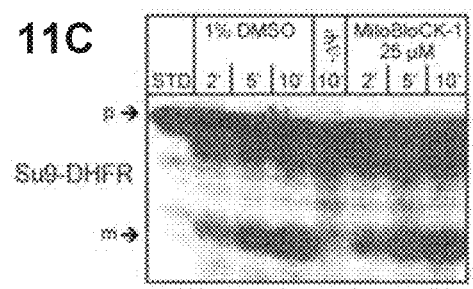

Figure 12
12A
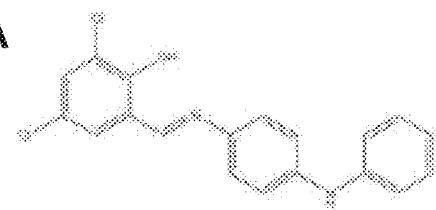
MitoBloCK-6
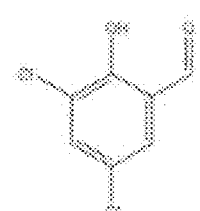
3,5-dichlorosalicylaldehyde
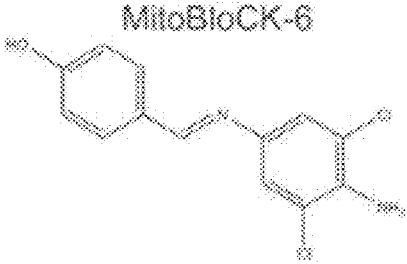
ES-1
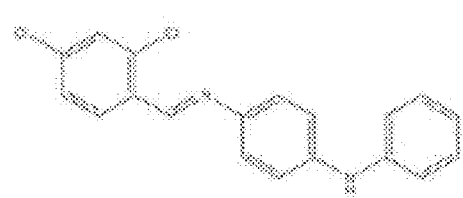
ES-2
12B
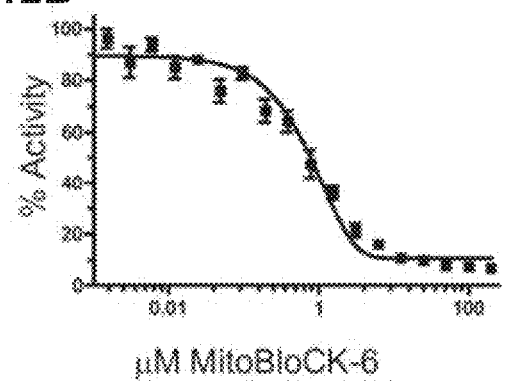
µM MitoBloCK-6
12C
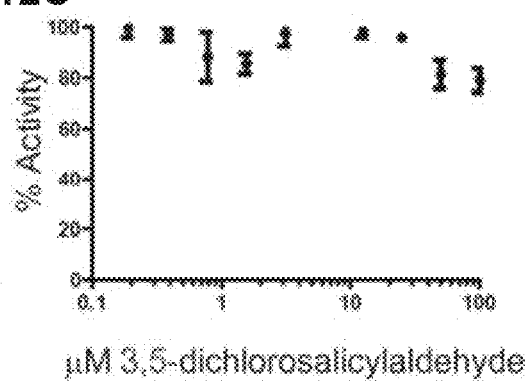
µM 3,5-dichlorosalicylaldehyde

Dispense protein into assay plate

↓ Pin DMSO or compound from library plate into assay plate

Pin DMSO or compounds from library

↓ Incubate plate at 25°C for 1 hr

Dispense Amplex Red/HRP mix

↓ Incubate plate at 25°C for 12 min

Read fluorescent signal in HTS plate reader

13B Summary of screening campaign

| Library: | Number of compounds | Number of hits | Hit rate | Hits confirmed in rescreening |
|---|---|---|---|---|
| Chembridge | 30,000 | 132 | 0.44% | 128 (97%) |
| Asinex | 28,400 | 23 | 0.08% | 18 (78%) |
| Other (UCLA chemist collections/ focused libraries) | 9,900 | 39 | 0.40% | 38 (97%) |
| TOTAL | 68,300 | 194 | 0.28% | 184 (95%) |

13C

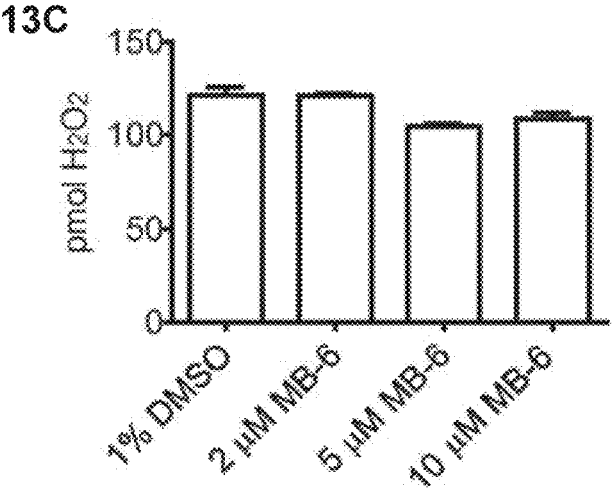

Figure 14
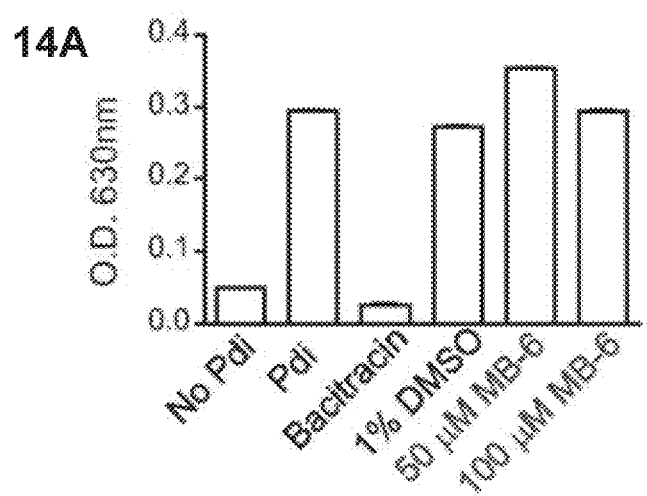
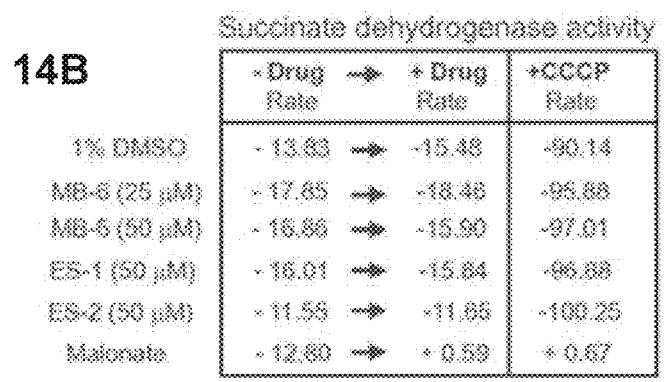

Figure 22
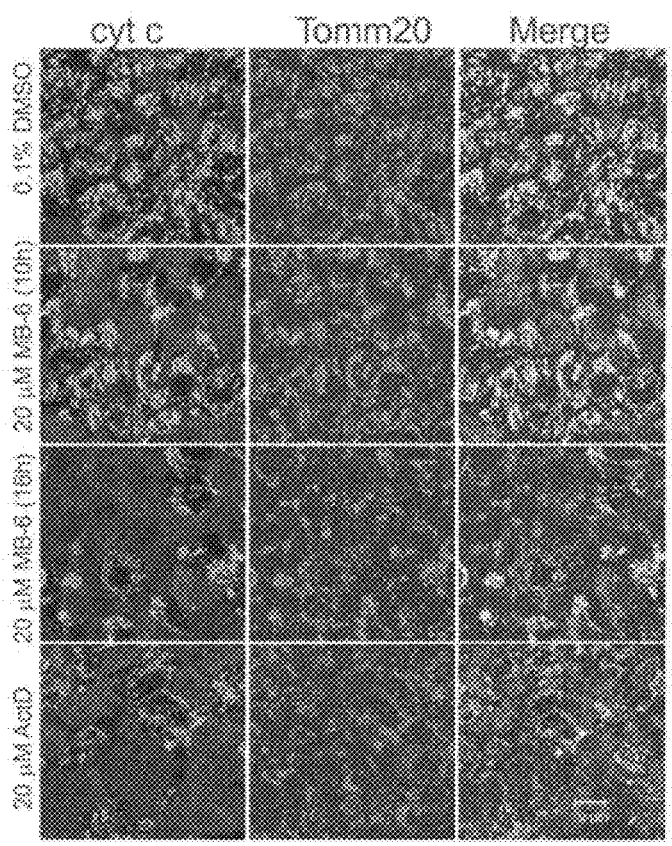
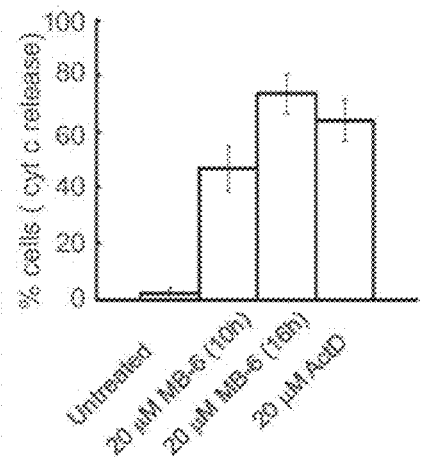
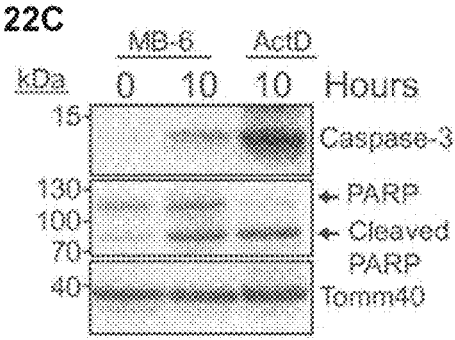
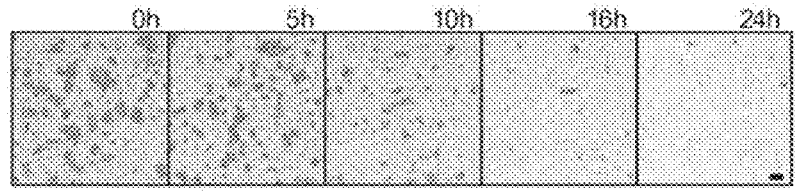
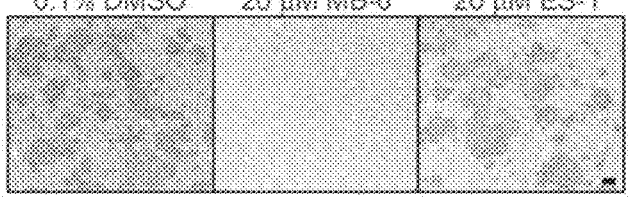

Figure 23
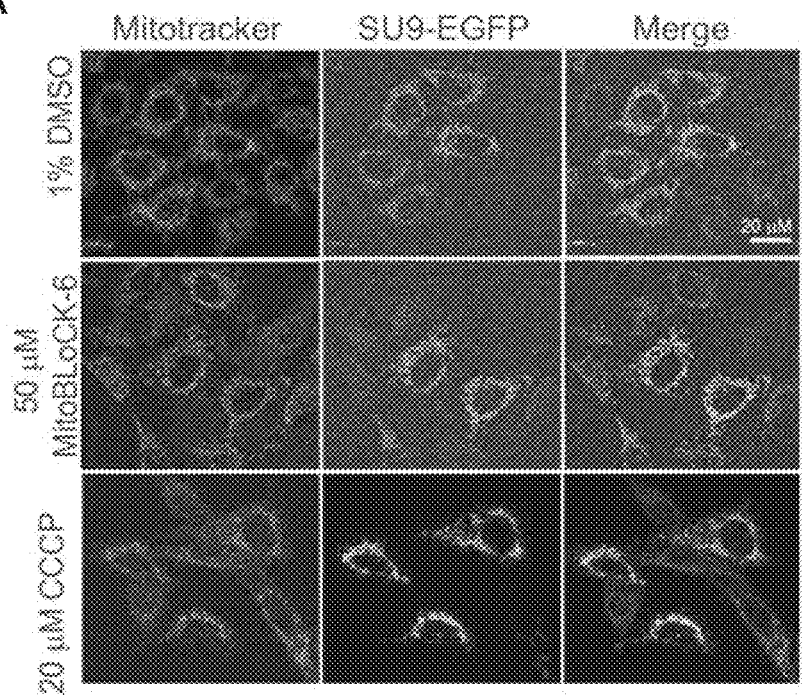
23A
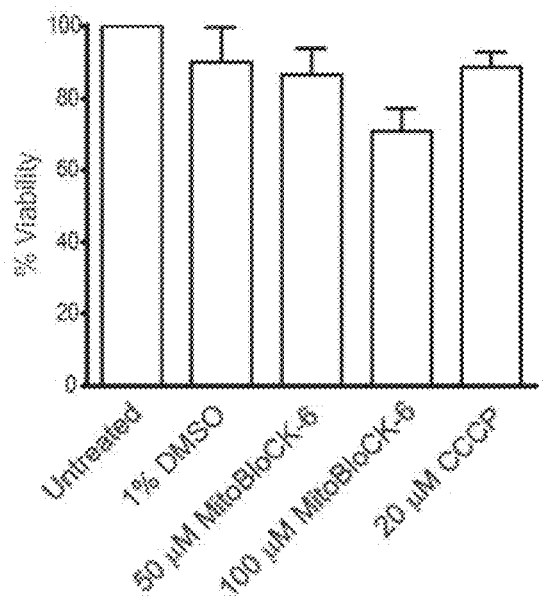
23B
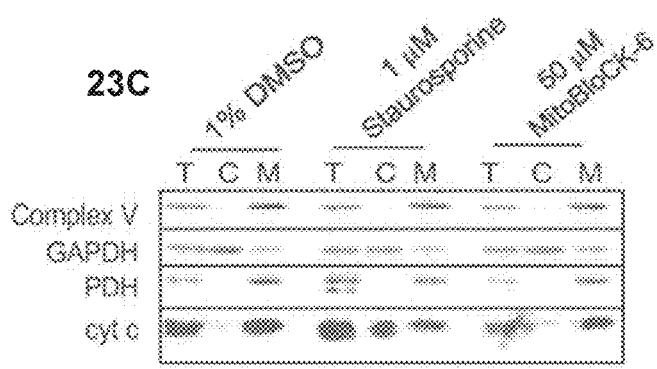
23C

Figure 24
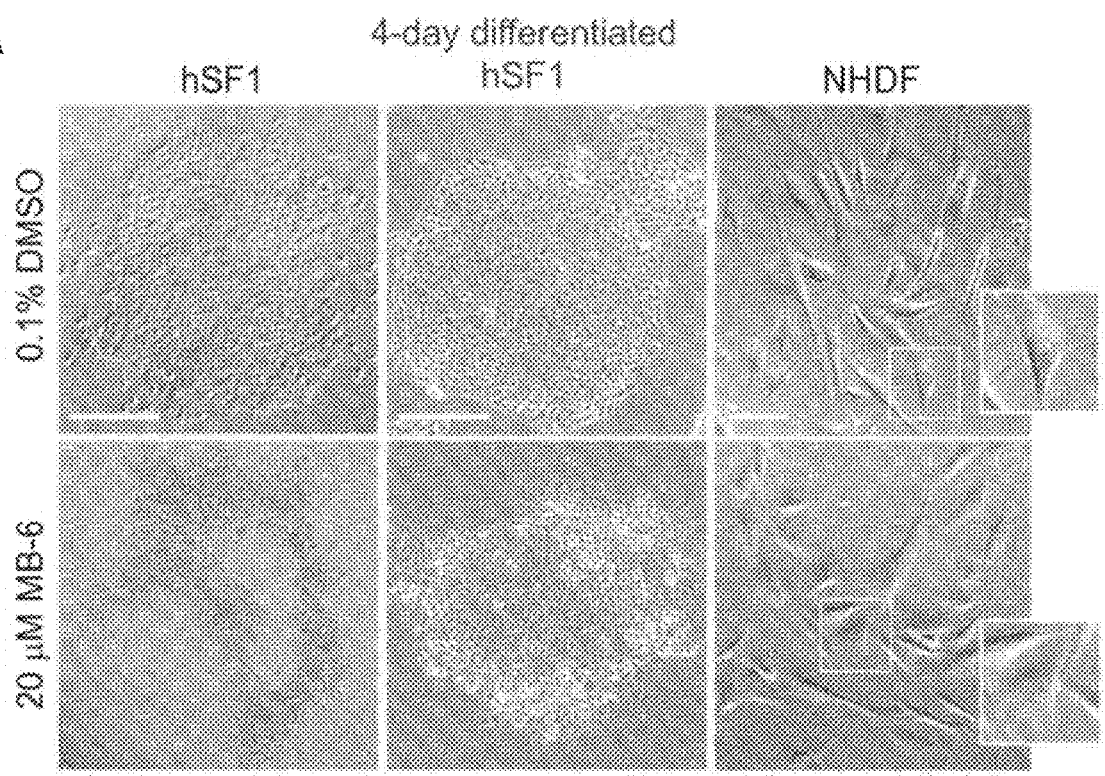
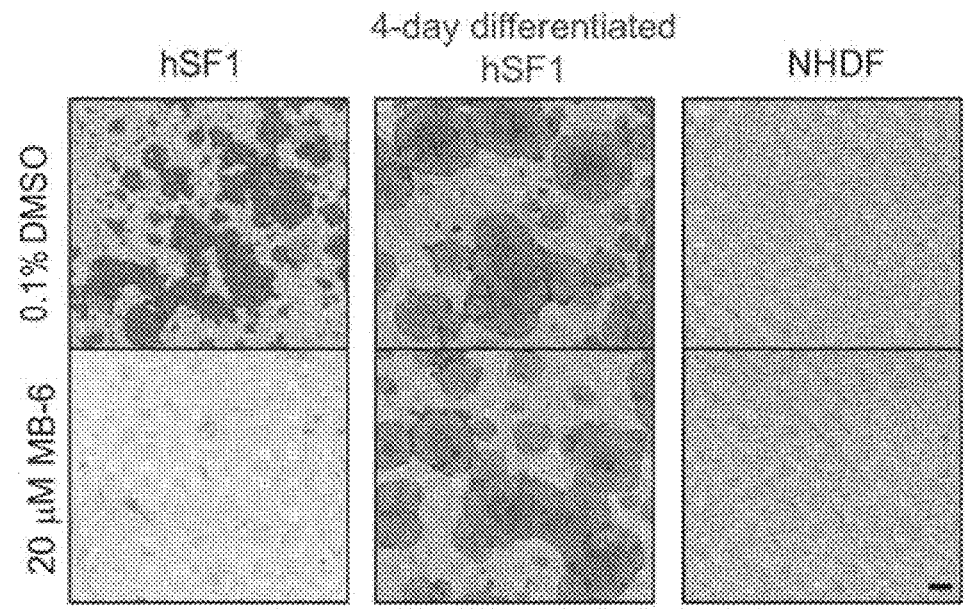

MODULATORS OF MITOCHONDRIAL PROTEIN IMPORT

CROSS-REFERENCES TO RELATED APPLICATIONS

This application is a Continuation of U.S. application Ser. No. 14/111,265 filed May 16, 2014, which is a 371 National Phase of PCT Application No. PCT/US2012/033279 filed Apr. 12, 2012, which claims priority benefit of U.S. Provisional Application No. 61/474,724 filed Apr. 12, 2011, the disclosures of each are incorporated by reference their entireties.

STATEMENT OF RIGHTS

This invention was made with Government support of Grant No. GM061721, awarded by the National Institutes of Health. The Government has certain rights in the invention.

FIELD OF THE INVENTION

The present invention generally relates to the field of providing therapeutics.

BACKGROUND OF THE INVENTION

All eukaryotic cells contain specialized organs called mitochondria that produce energy and house a host of metabolic processes essential for life. To achieve a fully functional state, mitochondria require proteins synthesized in the cell's cytosol to be imported into the proper location on or within them. This process is complicated because each mitochondrion is composed of two distinct compartments arising from the set of lipid membranes that surround them. Genetic, biochemical, and cellular studies have identified a complex translocation system, including translocons on the mitochondrial outer and inner membranes and intermembrane space of the mitochondrial FIG. 26.

The outer membrane contains the TOM (translocon of the outer membrane) protein complex, whereas the inner membrane contains the TIM23 (translocase of the inner membrane) and TIM22 complexes, which differ in their substrate specificity. Defects in the TIM22 import pathway lead to an inherited disease called deafness-dystonia syndrome, in which patients have deafness, blindness, and dystonia.

There is a need for compounds that are specific inhibitors of mitochondrial protein translocation. The inhibitors modulate the assembly or function of mitochondria.

There is a need for compounds effective for a disorder related to mitochondrial protein translocation.

The embodiments below address the above identified needs and issues.

SUMMARY OF THE INVENTION

In one aspect of the present invention, it is provided a method for identifying a specific inhibitor of mitochondrial protein translocation, which method comprising culturing a tim10-1 mutant strain of yeast in a medium with a library of drug-like compounds, identifying a drug-like compound as a hit compound if the drug-like compound significantly inhibits growth of the tim10-1 mutant strain of yeast, subjecting the hit compound to a counter screen which comprises incubating the hit compound with the tim10-1 mutant strain and an isogenic control strain carrying an integrated version of the TIM10 gene at the leu2 locus, and identifying the hit compound that selectively inhibits growth of the mutant strain but not the isogenic control strain as a hit compound for second counter screen where the second counter screen comprises:

incubating the hit compound for second counter screen with the tim10-1 mutant strain and a tim10-1 mutant strain harboring a plasmid containing a wild-type TIM10 gene, and identifying the hit compound that selectively inhibits growth of the tim10-1 mutant but not the tim10-1 mutant harboring a plasmid containing the wild-type TIM10 gene; and designating the hit compound that selectively inhibits growth of only the tim10-1 mutant in both the first counter screen and the second counter screen as the specific inhibitor of mitochondrial protein translocation ("MitoBloCk").

In some embodiments of the method, the drug-like compound inhibits growth of the tim10-1 mutant strain of yeast by 50% or above.

In some embodiments of the method, in combination with any of the above various embodiments, the hit compound selectively inhibits growth of the mutant strain by 50% or above.

In some embodiments of the method, in combination with any of the above various embodiments, the hit compound selectively inhibits growth of the mutant strain by 80% or above.

In some embodiments of the method, in combination with any of the above various embodiments, the hit compound selectively inhibits growth of the mutant strain by 90% or above.

In some embodiments of the method, in combination with any of the above various embodiments, the hit compound selectively inhibits growth of the mutant strain by 99% or above.

In some embodiments of the method, in combination with any of the above various embodiments, the tim10-1 mutant has a concentration of about 10 µM.

In some embodiments of the method, in combination with any of the above various embodiments, the method comprises an integrated robotic system.

In another aspect of the present invention, it is provided a method for identifying a specific inhibitor or activator of mitochondrial disulfide relay pathways. The method comprises providing a system of testing purified components of the mitochondrial oxidative folding and disulfide relay pathway including Mia40, Cmc1, Erv1, ALR, cytochrome c, and small Tim proteins in a medium with a library of drug-like compounds, identifying a drug-like compound as a hit compound if the drug-like compound significantly inhibits or activates the activity of at least one of redox-active enzymes, subjecting the hit compound to a counter screen which comprises incubating the hit compound with a yeast or mammalian cell line that reports the growth inhibition of a yeast strain or mammalian cell line that had attenuated activity in its mitochondrial disulfide relay pathway and an isogenic control strain or cell line carrying a non-attenuated version of the mitochondrial disulfide relay system, and identifying the hit compound that selectively inhibits or promotes the growth of the attenuated stain or cell line but not the strain or cell line as a hit compound for second counter screen where the second counter screen comprises:

incubating the hit compound for second counter screen with the a member of a redox-active enzyme family other than ALR or Erv1, and identifying the hit compound that selectively inhibits or activates the activity of ALR or Erv1 but not the related redox-active enzyme; and designating the hit compound that selectively inhibits or activates the activity of ALR or Erv in both the first counter screen and the second counter screen as the specific inhibitor of the mitochondrial disulfide relate system ("MitoBloCk").

In some embodiments of the method, the drug-like compound inhibits or activates the activity of ALR or Erv1 by 50% or above.

In some embodiments of the method, the hit compound selectively inhibits or activates the activity of ALR or Erv1 by 50% or above.

In some embodiments of the method, the hit compound selectively inhibits or activates the activity of ALR or Erv1 by 80% or above.

In some embodiments of the method, the hit compound selectively inhibits or activates the activity of ALR or Erv1 by 90% or above.

In some embodiments of the method, the compound selectively inhibits or activates the activity of ALR or Erv1 by 99% or above.

In some embodiments of the method, in combination with any of the above various embodiments, the tim10-1 mutant has a concentration of Erv1 or ALR is at or below its Michaelis-Menten constant (Km).

In some embodiments of the method, in combination with any of the above various embodiments, the tim10-1 mutant has a concentration of Erv1 or ALR is at or below its Michaelis-Menten constant (Km).

In some embodiments of the method, in combination with any of the above various embodiments, the tim10-1 mutant has a concentration of Erv1 or ALR is about 1 μM.

In some embodiments of the method, in combination with any of the above various embodiments, the method comprises an integrated robotic system.

In another aspect of the present invention, embodiments of the invention herein provide a specific inhibitor of mitochondrial protein translocation, which the inhibitor specifically targets the protein translocation pathway thereby modulating the assembly and function of the mitochondrion with respect to protein translocation and import. In some embodiments, the inhibitors are molecules or compounds, derivatives thereof or pharmaceutically acceptable salts thereof. In some embodiments, the compound has a structure of formula I, II or III:

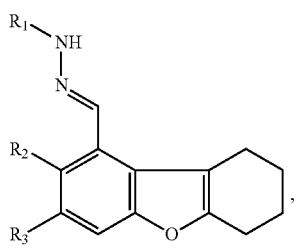

Formula I

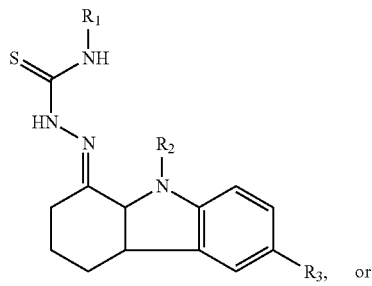

Formula II

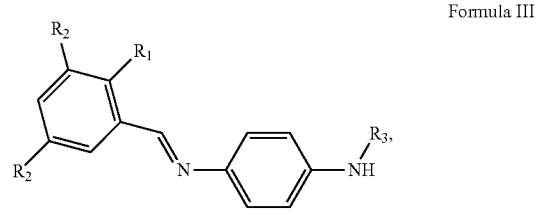

Formula III a derivative thereof, or pharmaceutically acceptable salt thereof, wherein each $R_1$, $R_2$, and $R_3$ is independently H, C1-C10 straight-chained or branched alkyl (substituted or unsubstituted), C1-C10 cycloalkyl (substituted or unsubstituted), C1-C10 straight-chained or branched alkeynyl (substituted or unsubstituted), C1-C10 cycloalkenyl (substituted or unsubstituted), C1-C10 aryl (substituted or unsubstituted), phenyl, carboxyl, hydroxyl, amino, carbonyl, carbonate, halo (F, Cl, Br, or I), thiol, thiourea, urea, or triazole groups. In some embodiments, the compound is

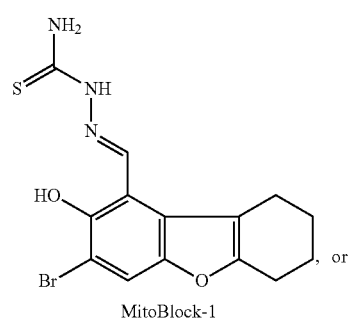

MitoBlock-1

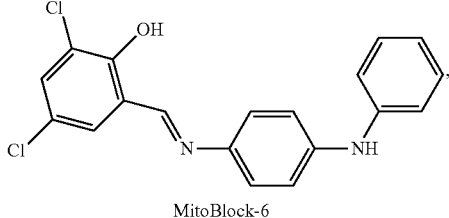 [SMILES: Oc1c(Cl)cc(Cl)cc1/C=N/c1ccc(Nc2ccccc2)cc1]

MitoBlock-6 a derivative thereof, or a pharmaceutically acceptable salt thereof. In some embodiments, the compound has a structure of formula A-D:

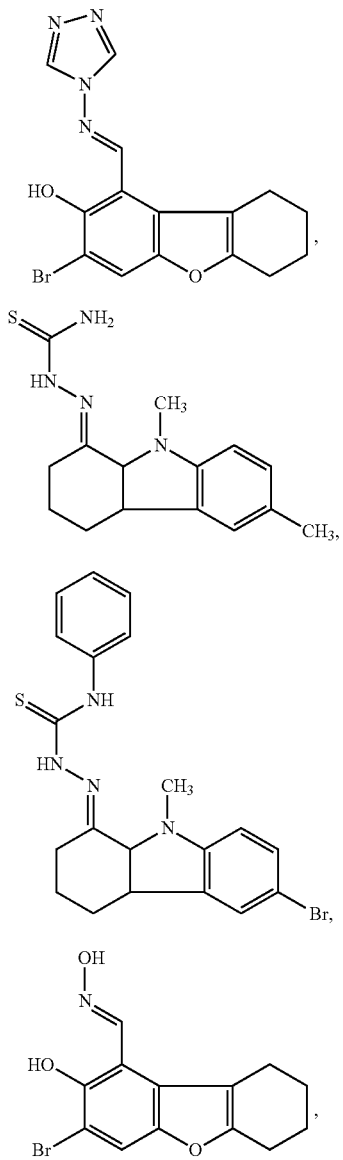

derivatives thereof, or pharmaceutically acceptable salts thereof.

The molecules are effective for treating or ameliorating disorders related to mitochondrial protein import. In some embodiments, the disorder is related to deafness-dystonia syndrome (e.g., blindness, deafness, and dystonia). In some embodiments, the disorder is a disease caused by defects in mitochondrial function. Some examples of such diseases are cancer, Parkinson's disease, or Alzheimer's disease.

In some embodiments, it is provided a composition comprising the compound disclosed herein. Compositions can be formed to include an effective amount of a compound disclosed herein. In some embodiments, the composition can include a carrier, e.g., a pharmaceutically acceptable carrier.

In some embodiments, it is provided a method of using the compound. Generally, the method comprises modulating the assembly and/or function of mitochondria by applying a compound disclosed herein to a body of mitochondria or a cell. The cell can be cultured cell, or an organism dissolved in solution, or a living organism such as an animal (e.g., human being). In some embodiments, the compound can be included in a composition which optionally includes a pharmaceutically acceptable carrier.

Other embodiments of the present invention include method of making the compound disclosed herein and method of forming a composition disclosed herein.

BRIEF DESCRIPTION OF THE DRAWINGS

FIG. 2A-FIG. 2B: show MitoBloCK-1 exhibits a chemical synthetic lethality with the tim10-1 mutant. (A) The structure of MitoBloCK-1, a tetrahydrodibenzofuran compound. (B) $MIC_{50}$ analysis of two tim10 mutants (tim10-1 and tim10-73) and the parental (TIM10) strain with MitoBloCK-1. Average % survival±SD of n=3 trials. The $R^2$ values for tim10-1 and tim10-73 curve fits were 0.98 and 0.99, respectively.

FIG. 3A-FIG. 3D: show MitoBloCK-1 inhibits the import of substrates that use the TIM22 import pathway. Import assays were performed with radiolabeled precursors into mitochondria from the tim10-1 tim9S suppressor strain, which has restored import of AAC. Time course assays were completed with various concentrations of MitoBloCK-1 or the vehicle control (1% DMSO). Non-imported precursor was removed by protease treatment. Precursors include (A) AAC, (B) the phosphate carrier (PIC), (C) Tom40, and (D) Hsp60, Panels a-c represent precursors that use the TIM22 import pathway whereas panel d is a substrate of the TIM23 import pathway. p, precursor; m, mature.

FIG. 5A-FIG. 5C: show MitoBloCK-1 facilitates substrate specificity analysis. Tim22 (A), Tim23 (B), and Tafazzin (C) were imported into tim10-1 tim9S mitochondria in the presence of MitoBloCK-1 or the vehicle (1% DMSO) followed by carbonate extraction to confirm insertion into the membrane.

FIG. 6A-FIG. 6C: show MitoBloCK-1 activity is influenced by specific chemical characteristics and inhibits AAC imported into mammalian mitochondria. (A) Analogs of MitobloCK-1 were purchased from Chembridge and assayed in import assays with radiolabled AAC as previously described. (B) AAC was imported into isolated mouse liver mitochondria in the presence of 25 µM MitoBloCK-1 as in FIG. 3A. (C) Model of MitoBloCK-1 activity from experimental evidence. See text for more details.

FIG. 7A-FIG. 7B: show phenotypic analysis of the strains used for the chemical synthetic-lethality screen for inhibitors of the TIM22 protein import pathway. (A) Steady-state levels of mitochondrial proteins determined by immunoblot analysis. Equivalent amounts of purified mitochondria were prepared from each strain and mitochondrial proteins were subsequently immunoblotted with polyclonal antibodies. The antibody against AAC also cross-reacted with porin (denoted by *) (B) Mitochondria were solubilized in buffer with 1.6 mg/ml n-dodecylmaltoside and separated on a 6-16% blue-native gel. Proteins were transferred to a PVDF membrane and blotted with antibodies against Tim9 and Tim10.

FIG. 10A-FIG. 10H: show MitoBloCK-1 does not impair general mitochondrial function. Respiration measurements were performed with an oxygen electrode using yeast mitochondria (M) from the tim10 tim9S suppressor strain in the presence of (A) 1% DMSO (vehicle control for drug) and (B) MitoBloCK-1. Respiration was initiated with NADH addition. 25 µM MitoBloCK-1 or 1% DMSO was added once steady-state respiration had been established. As a control, CCCP was added to uncouple the electron transport chain. (C) Respiration for series with DMSO or MitoBloCK-1 addition was quantitated (n=3). Bars represent mean rates with standard deviations as error bars. (D) Membrane potential (Δψ) of mitochondria measurements of purified mitochondria were performed with the fluorescent dye rhodamine 123 using a fluorimeter. Coupled mitochondria (M) sequestered and quenched the dye fluorescence; 1% DMSO was added to determine its effect on the A. Collapse of the Δψ initiated by CCCP was included as a control. (E) As in D, but 25 µM MitoBloCK-1 was added to determine its effect on the A. (F) 50 µM MitoBloCK-1 (MB-1) was added to purified 100 ug/ml tim10-1 tim9S mitochondria for 30 min at 25° C. in import buffer and released proteins (S) were separated from mitochondria (P) by centrifugation. Immunoblot analysis was performed to determine fractionation for Hsp60, Tom40, AAC, cyt c, and Tim10. As a control, treatment with the vehicle (1% DMSO) and MitoBloCK-2 (MB-2, disrupts mitochondrial membranes) was included. (G) As in 'F', but integrity was investigated with Coomassie staining. (H) As in 7B, MitoBloCK-1 (25 and 50 µM) was incubated with mitochondria and assembly of the Tim9-Tim10 complex was monitored by BN gels and immunoblotting with antibodies against Tim 10.

FIG. 11A-FIG. 11C: show MitoBloCK-1 inhibits import into mammalian mitochondria and growth of HeLa cells. (A) The effect of MitoBloCK-1 (MB-1) on HeLa cells was demonstrated with an MTT cell viability assay. Cultured cells were treated for 24-hours with DMSO or 25 and 50 µM MitoBloCK-1. Bars display mean cell viability where 100% was defined as signal from untreated samples. Error bars are standard deviations (n=3 trials). P value for t-tests between DMSO and MitoBloCK-1 illustrated with bracket lines. (B, C) As a control for FIG. 7B, the import of Hsp60 and Su9-DHFR that are targeted to the matrix was also tested in isolated mouse liver mitochondria in the presence and absence of a membrane potential. Note for Su9-DEFR import, the mitochondria were not treated with protease after import to remove non-imported Su9-DHFR because the DHFR is resistant to protease degradation. The processed fowl (mature, m) indicates the amount of precursor that has been imported. p, precursor; m, mature.

FIG. 12A-FIG. 12C: show that MitoBloCK-6 inhibits Erv1 activity. (A) The structure of MitoBloCK-6, Erv1 SAR compound-1 (ES-1) and compound-2 (ES-2), and 3,5-dichlorosalicyclaldehyde. (B) IC$_{50}$ analysis of MitoBloCK-6 in the in vitro Erv1 activity assay. 10 µM Erv1 was incubated with varying concentrations of MitoBloCK-6 as described for the chemical screen (C) As in 'B', IC$_{50}$ analysis with 3,5-dichlorosalicylaldehyde and Erv1.

FIG. 13A-FIG. 13C: illustrate the high-throughput screen to identify Erv1 inhibitors. (A) Schematic of the Erv1 high-throughput screen. (B) Summary of the screening analysis. (C) 2, 5, and 10 µM of MitoBloCK-6 were preincubated with Amplex Red/HRP before the reaction was initiated by the addition of 800 nM H$_2$O$_2$. The fluorescence intensity was measured after 12 min. (n=5)

FIG. 14A-FIG. 14B: show that MitoBloCK-6 does not inhibit PDI-mediated insulin reduction or succinate dehydrogenase activity. (A) 160 µM insulin was reacted with 3 units of PDI in the presence of buffer, 1 mM bacitracin, or MitoBloCK-6 (MB-6). Reduction of insulin chains was initiated by the addition of DTT. The samples were incubated for 30 min at room temperature and then the turbidity was measured at a wavelength of 630 nm using a Bio-Tek plate-reader. (B) Succinate dehydrogenase activity was measured in WT mitochondria using a Clark-type oxygen electrode. Respiration was initiated with 10 mM succinate and, when steady-state respiration was established, 25 or 50 µM MitoBloCK-6, 50 µM ES-1, 50 µM ES-2, or 1% DMSO was added. Controls included 20 mM malonate that inhibits succinate dehydrogenase activity and CCCP that uncouples electron transport. The rate is reported as nmol O$_2$ consumed/sec.

FIG. 22A-FIG. 22E: show that MitoBloCK-6 induces apoptosis in pluripotent stem cells. (A) HSF1 cells were treated with 20 μM MitoBloCK-6 or 0.1% DMSO. As a positive control, apoptosis was induced in cells by treatment with 20 μM actinomycin D (ActD) and 100 μM z-VAD-fmk for 16 hours. Cells were fixed and analyzed by immunofluorescence microscopy using antibodies against cyt c (green) and Tomm20 (Red). Merged images are also depicted in panels. (B) Quantification of data obtained in (A) and represented as % of cells that lost the mitochondrial cyt c staining but retained Tomm20 staining. Data was collected from three independent experiments. Error bars represent standard deviation. (C) As in 'A', HSF1 cells were treated with 20 μM MitoBloCK-6 or 20 μM ActD for the indicated time. Whole cell extracts were analyzed by SDS-PAGE and immunoblotted with antibodies for caspase-3 fragment and PARP. Tomm40 was included as a loading control. (D) As in 'A', HSF1 cells were treated with 20 μM MitoBloCK-6 for the indicated times followed by staining for alkaline phosphatase activity. Scale bar, 500 μm. (E) Analysis of alkaline phosphatase activity in HSF1 cells after treatment with either 0.1% DMSO, 20 μM MitoBloCK-6 or 20 μM ES-1 for 24 hours. Scale bar, 500 μm.

FIG. 23A-FIG. 23C: demonstrate that MitoBloCK-6 does not inhibit cell growth or alter mitochondrial morphology in HeLa cells. (A) HeLa cells were transiently transfected with Su9-EGFP. Following transfection, cells were treated for 12 hr with 50 μM MitoBloCK-6 or control 1% DMSO. As a positive control, cells were incubated with 20 μM CCCP to dissipate the membrane potential. Mitochondria were also stained with 10 μM MitoTracker Red. Mitochondrial morphology was assessed by fluorescence microscopy and the Mitotracker Red and GFP channels were superimposed (Merge). (B) The effect of MitoBloCK-6 on the viability of HeLa cells was assessed with a MTT-based toxicology assay. Cultured cells were treated for 12-16 hr with DMSO or 50 μM and 100 μM MitoBloCK-6. Bars display mean cell viability where 100% was defined as signal from untreated samples. Error bars display standard error of the mean (n=5). (C) The release of cyt c was investigated. Cells were treated with 1% DMSO or 50 μM MitoBloCK-6 for 12-16 hr and fractionated into mitochondrial (M) and cytosolic (C) fractions. Release of mitochondrial proteins was assessed by immunoblot analysis with antibodies against cyt c, Complex V (ATP synthase subunit alpha), pyruvate dehydrogenase (PDH), and cytosolic GAPDH. Treatment with 1 μM staurosporine for 4 hr induced apoptosis and was included as a positive control.

FIG. 24A-FIG. 24B: illustrate that MitoBloCK-6 inhibits growth of pluripotent but not differentiated cells. (A) Brightfield images of hSF1 cells, retinoic acid differentiated 4-day hSF1 cells, and NHDF cells treated with 20 μM MitoBloCK-6 or 0.1% DMSO for 16 hr. (B) As in 'A', cells were stained with Coomassie brilliant blue. Scale bar, 750 μm.

DETAILED DESCRIPTION OF THE INVENTION

Figure 1:
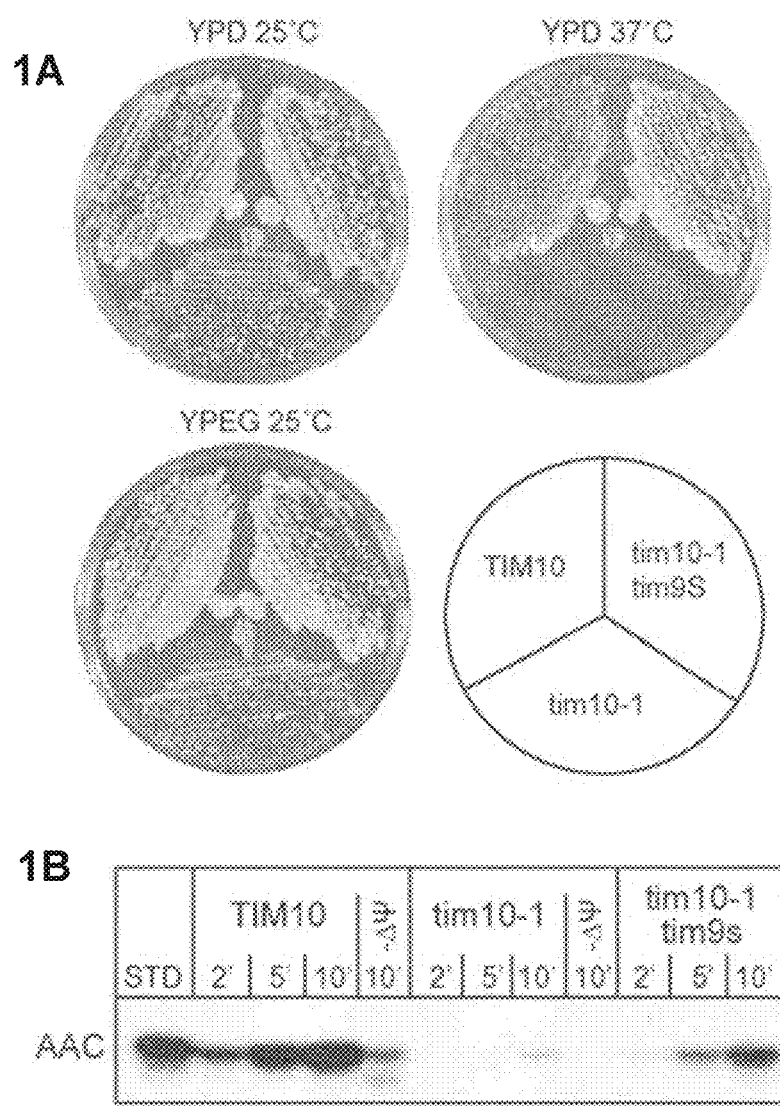
FIG. 1A-FIG. 1B: show a phenotypic analysis of the strains used for the chemical synthetic-lethality screen for inhibitors of the TIM22 protein import pathway. (A) Growth phenotypes of the control (TIM/0), the tim10-1 mutant, and tim10-1 suppressor (tim10-1 tim9S) strains used in the screen. Strains were plated on rich glucose (YPD) or ethanol-glycerol (YPEG) media and incubated at 25° C. or 37° C. All of these strains were isogenic except for their denoted genetic variation. (B) Radiolabeled AAC was imported into isolated mitochondria in the presence and absence of a membrane potential (Δψ). Aliquots were removed at the indicated time points and samples were treated with carbonate extraction to confirm that AAC was inserted into the IM.

In one aspect of the present invention, it is provided a method for identifying a specific inhibitor of mitochondrial protein translocation, which method comprising culturing a tim10-1 mutant strain of yeast in a medium with a library of drug-like compounds, identifying a drug-like compound as a hit compound if the drug-like compound significantly inhibits growth of the tim10-1 mutant strain of yeast, subjecting the hit compound to a counter screen which comprises incubating the hit compound with the tim10-1 mutant strain and an isogenic control strain carrying an integrated version of the TIM10 gene at the leu2 locus, and identifying the hit compound that selectively inhibits growth of the mutant strain but not the isogenic control strain as a hit compound for second counter screen where the second counter screen comprises:

incubating the hit compound for second counter screen with the tim10-1 mutant strain and a tim10-1 mutant strain harboring a plasmid containing a wild-type TIM10 gene, and identifying the hit compound that selectively inhibits growth of the tim10-1 mutant but not the tim10-1 mutant harboring a plasmid containing the wild-type TIM10 gene; and designating the hit compound that selectively inhibits growth of only the tim10-1 mutant in both the first counter screen and the second counter screen as the specific inhibitor of mitochondrial protein translocation ("MitoBloCk").

In some embodiments of the method, the drug-like compound inhibits growth of the tim10-1 mutant strain of yeast by 50% or above.

In some embodiments of the method, in combination with any of the above various embodiments, the hit compound selectively inhibits growth of the mutant strain by 50% or above.

In some embodiments of the method, in combination with any of the above various embodiments, the hit compound selectively inhibits growth of the mutant strain by 80% or above.

In some embodiments of the method, in combination with any of the above various embodiments, the hit compound selectively inhibits growth of the mutant strain by 90% or above.

In some embodiments of the method, in combination with any of the above various embodiments, the hit compound selectively inhibits growth of the mutant strain by 99% or above.

In some embodiments of the method, in combination with any of the above various embodiments, the tim10-1 mutant has a concentration of about 10 μM.

In some embodiments of the method, in combination with any of the above various embodiments, the method comprises an integrated robotic system.

In another aspect of the present invention, it is provided a method for identifying a specific inhibitor or activator of mitochondrial disulfide relay pathways. The method comprises providing a system of testing purified components of the mitochondrial oxidative folding and disulfide relay pathway including Mia40, Cmc1, Erv1, ALR, cytochrome c, and small Tim proteins in a medium with a library of drug-like compounds, identifying a drug-like compound as a hit compound if the drug-like compound significantly inhibits or activates the activity of at least one of redox-active enzymes, subjecting the hit compound to a counter screen which comprises incubating the hit compound with a yeast or mammalian cell line that reports the growth inhibition of a yeast strain or mammalian cell line that had attenuated activity in its mitochondrial disulfide relay pathway and an isogenic control strain or cell line carrying a non-attenuated version of the mitochondrial disulfide relay system, and identifying the hit compound that selectively inhibits or promotes the growth of the attenuated stain or cell line but not the strain or cell line as a hit compound for second counter screen where the second counter screen comprises:

incubating the hit compound for second counter screen with the a member of a redox-active enzyme family other than ALR or Erv1, and identifying the hit compound that selectively inhibits or activates the activity of ALR or Erv1 but not the related redox-active enzyme; and designating the hit compound that selectively inhibits or activates the activity of ALR or Erv in both the first counter screen and the second counter screen as the specific inhibitor of the mitochondrial disulfide relate system ("MitoBloCk").

In some embodiments of the method, the drug-like compound inhibits or activates the activity of ALR or Erv1 by 50% or above.

In some embodiments of the method, the hit compound selectively inhibits or activates the activity of ALR or Erv1 by 50% or above.

In some embodiments of the method, the hit compound selectively inhibits or activates the activity of ALR or Erv1 by 80% or above.

In some embodiments of the method, the hit compound selectively inhibits or activates the activity of ALR or Erv1 by 90% or above.

In some embodiments of the method, the compound selectively inhibits or activates the activity of ALR or Erv1 by 99% or above.

In some embodiments of the method, in combination with any of the above various embodiments, the tim10-1 mutant has a concentration of Erv1 or ALR is at or below its Michaelis-Menten constant (Km).

In some embodiments of the method, in combination with any of the above various embodiments, the tim10-1 mutant has a concentration of Erv1 or ALR is at or below its Michaelis-Menten constant (Km).

In some embodiments of the method, in combination with any of the above various embodiments, the tim10-1 mutant has a concentration of Erv1 or ALR is about 1 μM.

In some embodiments of the method, in combination with any of the above various embodiments, the method comprises an integrated robotic system.

In another aspect of the present invention, embodiments of the invention herein provide a specific inhibitor of mitochondrial protein translocation, which the inhibitor specifically targets the protein translocation pathway thereby modulating the assembly and function of the mitochondrion with respect to protein translocation and import. In some embodiments, the inhibitors are molecules or compounds, derivatives thereof or pharmaceutically acceptable salts thereof. In some embodiments, the compound has a structure of formula I, II or III:

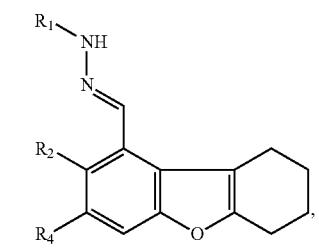

Formula I

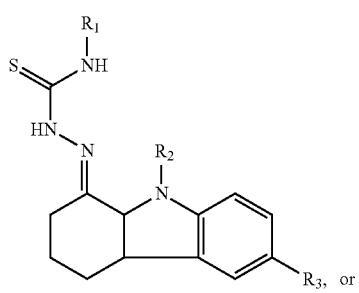

Formula II

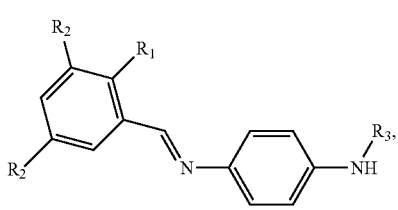

Formula III a derivative thereof, or pharmaceutically acceptable salt thereof, wherein each $R_1$, $R_2$, and $R_3$ is independently H, C1-C10 straight-chained or branched alkyl (substituted or unsubstituted), C1-C10 cycloalkyl (substituted or unsubstituted), C1-C10 straight-chained or branched alkeynyl (substituted or unsubstituted), C1-C10 cycloalkenyl (substituted or unsubstituted), C1-C10 aryl (substituted or unsubstituted), phenyl, carboxyl, hydroxyl, amino, carbonyl, carbonate, halo (F, Cl, Br, or I), thiol, thiourea, urea, or triazole groups. In some embodiments, the compound is

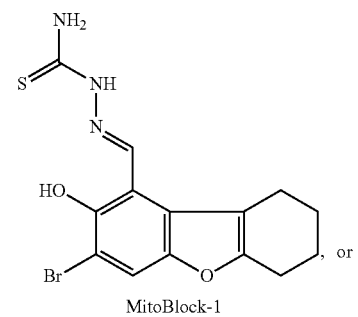

MitoBlock-1

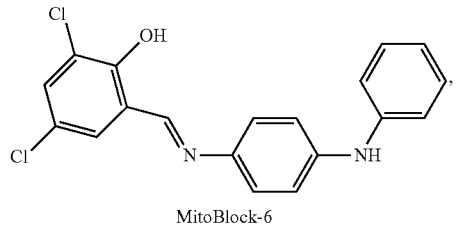 [SMILES: Oc1c(Cl)cc(Cl)cc1/C=N/c1ccc(Nc2ccccc2)cc1]

MitoBlock-6 a derivative thereof, or a pharmaceutically acceptable salt thereof. In some embodiments, the compound has a structure of formula A-D:

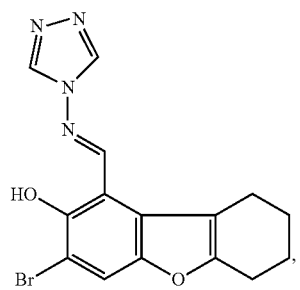

A

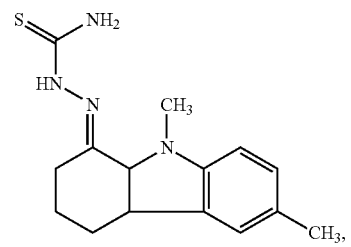

B

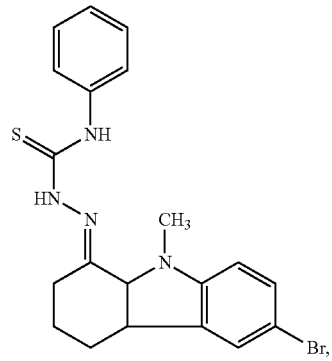

C

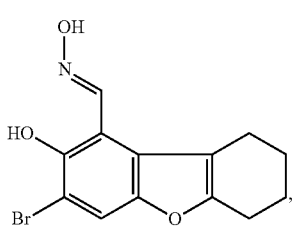

derivatives thereof, or pharmaceutically acceptable salts thereof.

The molecules are effective for disorders related to mitochondrial protein import. In some embodiments, the disorder is related to deafness-dystonia syndrome (e.g., blindness, deafness, and dystonia). In some embodiments, the disorder is a disease caused by defects in mitochondrial function. Some examples of such diseases are cancer, Parkinson's disease, or Alzheimer's disease.

In some embodiments, it is provided a composition comprising the inhibitor or compound disclosed herein. Compositions can be formed to include an effective amount of a compound disclosed herein. In some embodiments, the composition can include a carrier, e.g., a pharmaceutically acceptable carrier.

In some embodiments, it is provided a method of using the compound. Generally, the method comprises modulating the assembly and/or function of mitochondria by applying a compound disclosed herein to a body of mitochondria or a cell. The cell can be cultured cell, or an organism dissolved in solution, or a living organism such as an animal (e.g., human being). In some embodiments, the compound can be included in a composition which optionally includes a pharmaceutically acceptable carrier.

Other embodiments of the present invention include method of making the compound disclosed herein and method of forming a composition disclosed herein.

The present invention represents a significant innovation. Prior to the discovery of these compounds, scientists could only modulate the biogenesis of mitochondria using genetic manipulation or non-specific drug treatments. Genetic manipulations are mostly limited to single celled organisms such as yeast and are not titratable or reversible. The available chemical tools for mitochondrial biogenesis are limited in their utility since they are either nonspecific inhibitors or metabolic poisons that block cellular respiration. Recently, Nunnari and colleagues (U.S. patent application publication No. 20050038051) discovered a drug compound that regulated the fission and fusion of mitochondria. Their discovery of mdivi-1 was the first drug that could specifically alter mitochondrial dynamics. However, at this time there are no known drugs that target the assembly of the mitochondrion with respect to protein translocationl import. Our invention specifically targets the protein translocation pathway.

The studies disclosed in the present invention show that the inhibition by the invention compounds is specific to the protein import machinery. The following targets are the most probable ones for studying the mechanism of action:

i. MitoBloCK-1: Tim9/1 0 chaperone complex;
ii. MitoBloCK-2: Tom40 outer membrane translocation pore;
iii. MitoBloCK-3: Small Tim protein chaperones
iv. MitoBloCK-6: Redox cycling of small Tim protein chaperones We have shown that these drugs have activity in both biochemical experiments with purified cellular components and in live cells.

As used herein, the term "specific inhibitor of mitochondrial protein translocation" refers to a small molecule that specifically targets the protein translocation pathway so as to modulate the assembly and function of the mitochondrion with respect to protein translocation and import.

The term "tim10-1 mutant" is well known to a person of ordinary skill in the art.

"Small Tim proteins" are well documented in the art and marked by their conserved 'twin Cx(3)C' motif separated by 11-16 residues (see, e.g., C M Koehler, Trends Biochem Sci. 29(1):1-4 (2004); Webb, C. T., et al., Mol. Cell. 21(1): 123-133 (2006); and Mesecke, N., et al., Cell 121: 1059-1069 (2005)).

"Redox-active enzymes" are enzymes involved in redox reactions in a biological system. These enzymes are well known in the art and within the general knowledge of a person of ordinary skill in the art.

Method of Making

A compound disclosed herein can be readily prepared according to established methodology in the art of organic synthesis. General methods of synthesizing the compound can be found in, e.g., Stuart Warren and Paul Wyatt, Workbook for Organic Synthesis: The Disconnection Approach, second Edition, Wiley, 2010.

Methods of Use

In a further aspect, it is provided a method of using the compound disclosed herein. The method comprises applying the compound of invention to a subject to treat, prevent, or ameliorate a medical condition. The medical condition can be any disease or disorder caused by or otherwise associated with mitochondria protein translocation.

In some embodiments, the method can be conducted in living bodies of mammals. In such a case, the compounds may be administered to the mammals.

As used herein, the term disorder and medical condition include deafness-dystonia syndrome, cancer, Parkinson's disease, or Alzheimer's disease. In some embodiments, the deafness-dystonia syndrome includes deafness, blindness, and dystonia Pharmaceutical Compositions In another aspect of the present invention, a pharmaceutical composition for use in treatment or prevention of the diseases caused by or otherwise associated with mitochondria protein translocation. In some embodiments, the pharmaceutical composition comprises as an effective ingredient a compound expressed by any one of the aforementioned formulae a pharmacologically acceptable salt or prodrug thereof.

The pharmaceutical composition preferably comprises a compound described above or a pharmacologically acceptable salt or prodrug thereof.

The pharmaceutical composition more preferably comprises a compound shown in the aforementioned table.

In the aforementioned aspect of the present invention, the pharmaceutical composition may contain a pharmacologically acceptable carrier or excipients. An amount of the compound used in the pharmaceutical composition is not limited as far as it is an effective amount for treatment.

The pharmaceutical composition in the aspect of the present invention may contain, as active ingredients, the aforementioned compound and other compounds, or may contain a mixture of two or more aforementioned compounds.

The pharmacologically acceptable salt in the present specification is not specifically limited as far as it can be used in medicaments. Examples of a salt that the compound of the present invention forms with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

Further, the compounds of the present invention include hydrates thereof, various pharmaceutically acceptable solvates thereof, and polymorphic crystals thereof.

The pharmaceutical compositions of the present invention can be formulated in various dosage forms, which are exemplified by the following: oral administration forms such as tablets, capsules, powders, granules, pills, liquids, emulsions, suspensions, solutions, spirits, syrups, extracts, and elixirs; parenteral administration forms such as injections, for example, subcutaneous injections, intravenous injections, intramuscular injections, and intraperitoneal injections; transdermal administration forms, plasters and pressure sensitive adhesives, ointments or lotions; intramouth administration forms such as sublingual forms and oral patch preparations; and nasal administration forms such as aerosols, but are not limited thereto. These preparations can be manufactured by using a known method generally used in a drug manufacturing process. In one embodiment of the present invention, the pharmaceutical composition of the present invention may be administered for treating muscular disease as an injection such as an intramuscular injection for administering directly into muscle.

The pharmaceutical compositions may contain various kind of ingredients generally used, for example, one or more pharmaceutically acceptable fillers, disintegrators, diluents, lubricants, flavoring agents, colorants, sweetening agents, corrigents, suspending agents, humectants, emulsifying agents, dispersing agents, auxiliary agents, preservatives, buffers, binders, stabilizers, and coating agents. In addition, the pharmaceutical composition of the present invention may be sustained-release dosage forms or extended-release dosage forms.

Dosage ranges of the pharmaceutical compositions are not particularly limited, and can be determined in accordance with the following: effectiveness of the ingredients contained therein; the administration form; the route of administration; the type of disease; the characteristics of the subject (e.g., body weight, age, symptomatic conditions, and whether a subject is taking other pharmaceutical agents); and the judgment of a physician in charge. In general, a suitable dosage may fall, for example, within a range of about 0.01 µg to 100 mg, per 1 kg of the body weight of the subject, and preferably within a range of about 0.1 jag to 1 mg, per 1 kg of body weight. However, the dosage may be altered using conventional experiments for optimization of a dosage that are well known in the art. The aforementioned dosage can be divided for administration once to several times a day. Alternatively, periodic administration once every few days or few weeks can be employed.

The pharmaceutical compositions may be administered to a patient whose biological sample obtained in advance is subjected to a study for presence or absence of deafness-dystonia syndrome, cancer, Parkinson's disease, or Alzheimer's disease. A biological sample may be any ones insofar as it contains nucleic acids, and is exemplified by cells, bloods, cerebrospinal fluids, bronchoalveolar lavage fluids, expectorations, or other body fluids as well as biopsy tissues. Nucleic acid samples can be prepared from the biological samples for use. The nucleic acid samples can be prepared by well known nucleic acid preparation methods. The nucleic acid samples may be DNA or RNA. The nucleic acid samples prepared may be used directly for detection, or may be subjected to enzymatic amplification of predetermined region thereof by PCR or other amplification methods in advance for analysis.

In terms of a route of administration of the pharmaceutical composition, it may be either systemic administration or local administration. The route of administration that is appropriate for a particular disease, symptomatic condition, or other factors, should be selected. For example, parenteral administration including normal intravenous injection, intra-arterial administration, subcutaneous administration, intracutaneous administration, and intramuscular administration can be employed. Oral administration can be also employed. Further, transmucosal administration or transdermal administration can be employed.

Preferably the composition is adapted for oral administration, e.g. in the form of a tablet, coated tablet, dragee, hard or soft gelatin capsule, solution, emulsion or suspension. In general the oral composition will comprise from 1 mg to 400 mg of such agent. It is convenient for the subject to swallow one or two tablets, coated tablets, dragees, or gelatin capsules per day. However, the composition can also be adapted for administration by any other conventional means of systemic administration including rectally, e.g. in the form of suppositories, parenterally, e.g. in the form of injection solutions, or nasally.

The biologically active compounds can be processed with pharmaceutically inert, inorganic or organic carriers for the production of pharmaceutical compositions. Lactose, corn starch, or derivatives thereof, talc, stearic acid or its salts and the like can be used, for example, as such carriers for tablets, coated tablets, dragees and hard gelatin capsules. Suitable carriers for soft gelatin capsules are, for example, vegetable oils, waxes, fats, semi-solid and liquid polyols and the like. Depending on the nature of the active ingredient no carriers are, however, usually required in the case of soft gelatin capsules, other than the soft gelatin itself. Suitable carriers for the production of solutions and syrups are, for example, water, polyols, glycerol, vegetable oils and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, coating agents or antioxidants. They can also contain still other therapeutically valuable substances, particularly antidiabetic or hypolipidemic agents that act through mechanisms other than those underlying the effects of the compounds of the invention. Agents which can advantageously be combined with compounds of the invention in a single formulation include but are not limited to biguanides such as metformin, insulin releasing agents such as the sulfonylurea insulin releaser glyburide and other sulfonylurea insulin releasers, cholesterol-lowering drugs such as the "statin" HMG-CoA reductase inhibitors such as atrovastatin, lovastatin, pravastatin and simvastatin, PPAR-alpha agonists such as clofibrate and gemfibrozil, PPAR-gamma agonists such as thiazolidinediones (e.g. rosiglitazone and pioglitazone, alpha-glucosidase inhibitors such as acarbose (which inhibit starch digestion), and prandial insulin releasers such as repaglinide. The amounts of complementary agents combined with compounds of the invention in single formulations are in accord with the doses used in standard clinical practice. Established safe and effective dose ranges for certain representative compounds are set forth above.

The invention is described in more detail in the following illustrative examples. Although the examples can represent only selected embodiments of the invention, it should be understood that the following examples are illustrative and not limiting.

EXAMPLES

The following examples illustrate, but not limit, the embodiments of the invention.

Example 1. Studies on Substrate Specificity of the TIM22 Mitochondrial Import Pathway Revealed with Small Molecule Inhibitor of Protein Translocation Summary The TIM22 protein import pathway mediates the import of membrane proteins into the mitochondrial inner membrane and consists of two intermembrane space chaperone complexes, the Tim9-Tim10 and Tim8-Tim13 complexes. To facilitate mechanistic studies, we developed a chemical genetic approach to identify small molecule agonists that caused lethality to a tim10-1 yeast mutant at the permissive temperature. One molecule, MitoBloCK-1, attenuated the import of the carrier proteins including the ADP/ATP and phosphate carriers, but not proteins that used the TIM23 or the Mia40/Erv1 translocation pathways. MitoBloCK-1 impeded binding of the Tim9-Tim10 complex to the substrate during an early stage of translocation, when the substrate was crossing the outer membrane. As a probe to determine the substrate specificity of the small Tim proteins, MitoBloCK-1 impaired the import of Tim22 and Tafazzin, but not Tim23, indicating that the Tim9-Tim10 complex mediates the import of a subset of inner membrane proteins. MitoBloCK-1 also inhibited growth of mammalian cells and import of the ADP/ATP carrier, but not TIM23 substrates, confirming that MitoBloCK-1 can be used to understand mammalian mitochondrial import and dysfunction linked to inherited human disease. Our approach of screening chemical libraries for compounds causing synthetic genetic lethality to identify inhibitors of mitochondrial protein translocation in yeast validates the generation of new probes to facilitate mechanistic studies in yeast and mammalian mitochondria.

The mitochondrion has an outer (OM) and inner (IM) membrane that separates the matrix from the intermembrane space (IMS). The mitochondrion has developed an elaborate translocation system to orchestrate the import and subsequent sorting of proteins to the correct compartment (1). Proteins destined for the mitochondrion, termed precursors until they reach their correct location, utilize Translocase of the Outer Membrane (TOM) and Translocase of the Inner Membrane (TIM) complexes, TIM23 and TIM22, to cross the OM and IM, respectively. Proteins with a typical N-terminal targeting sequence use the TIM23 translocation system, whereas proteins destined for the IM use the TIM22 translocation system.

Components of the TIM22 translocation system include the small Tim proteins, Tim8, Tim9, Tim10, Tim12, and Tim13, and the membrane components Tim18, Tim22, and Tim54. The small Tim proteins assemble in 70-kDa hexameric complexes (referred to as small Tim complexes) in the IMS in which three Tim9 polypeptides partner with three Tim10 polypeptides, and three Tim8 polypeptides partner with three Tim13 polypeptides. Structural studies reveal that the overall structure is similar to that of the Skp and prefoldin chaperones (2), although the sequences are not conserved. The small Tim proteins function as chaperones to maintain the hydrophobic membrane proteins in an import competent state (3, 4). The 300-kDa insertion complex in the IM consists of a fraction of Tim9 and Tim10 with Tim12, Tim22, Tim18, and Tim54. The small Tim proteins escort substrates to the insertion complex, which mediates protein insertion into the membrane.

Substrates of the TIM22 complex include the carrier proteins such as the ADP/ATP carrier (AAC) and the phosphate carrier (PiC) and IM proteins Tim17, Tim22, and Tim23. In addition, the small Tim proteins facilitate the insertion of outer membrane proteins Tom40 and porin and the cardiolipin remodeling enzyme Tafazzin (5-7). The substrates cross the TOM complex as a loop in an unfolded state and then the small Tim proteins bind to the substrate at an early stage of translocation (4, 8, 9).

The Tim8-Tim13 and Tim9-Tim10 complexes display different substrate binding preferences. The Tim9-Tim10 complex can be efficiently cross-linked to carrier proteins and the import components Tim17, Tim23, and Tim22 (10-12). The Tim8-Tim13 complex can be cross-linked to Tim23 and the aspartate-glutamate carriers (10-13). Mutations in the human homolog of Tim8, DDP1, cause the X-linked disease deafness-dystonia syndrome (14, 15), and the disease may be caused by a decrease in specific IM proteins (13). Therefore, understanding the substrate specificity of the small Tim proteins is important for understanding the molecular basis of deafness-dystonia syndrome.

Mitochondrial assembly has been studied extensively using classical yeast genetics and biochemical assays with purified mitochondria. However, new strategies are needed to elucidate the details of protein translocation and its role in development and human disease. Important questions about the substrate specificity of the small Tim proteins and the mechanism by which the small Tim proteins bind substrate have not been resolved. These studies would be facilitated by drug-like inhibitors that modulate protein import. Here we report the development of a small molecule screening approach to identify inhibitors of the TIM22 import pathway. Taking advantage of our large collection of temperature-sensitive mutants for the TIM22 import pathway, we conducted a chemical genetic screen with a tim10-1 mutant to identify small molecules that caused a synthetic lethality at the permissive temperature of 25° C. (16-19). Our results indicate that a new set of tools for mechanistic studies in protein translocation can be developed and may be useful for characterizing protein translocation in mammalian mitochondria, where tools are lacking.

Results

A Screen to Identify Inhibitors of Mitochondrial Protein Translocation

We exploited a large collection of temperature sensitive mutants for the TIM22 import pathway (10, 16-18) and developed a composite synthetic lethal screen to identify small molecule inhibitors that blocked the TIM22 import pathway (19). The tim10-1 mutant was used as the starting strain (16); the strains used in this study are described in Table 51. The rationale in this screen was that small molecules might be identified that target the mutant Tim10 protein or other components of the TIM22 pathway and thereby cause lethality of the tim10-1 mutant at the permissive temperature of 25° C. This approach uses the well characterized synthetic growth defects of the tim10-1 mutant to guide the design of cells genetically sensitized for inhibition of the TIM22 pathway.

To generate a suitable strain for screening, genes for the multidrug resistance pumps PDR5 and SNQ2 were disrupted to increase the steady state intracellular concentration of the drugs in yeast (19). The tim10-1 mutant grew similar to the parental strain (designated TIM10) at 25° C. but failed to grow at the restrictive temperature of 37° C. (FIG. 1A). Growth was inhibited on media that contained glucose (YPD, supporting fermentable growth) or ethanol-glycerol (YPEG, supporting nonfermentable growth) as the sole carbon source. We verified that the abundance of the mutant Tim10 was decreased in the tim10-1 strain; however, the abundance of other mitochondrial proteins was not markedly decreased in mitochondria when the strain was grown at 25° C. (FIG. 7A) (16). In addition, deletion of the multidrug resistance pumps did not compromise growth or the mitochondrial protein profiles of the tim10-1 mutant. In contrast, when we investigated assembly of the soluble 70 kDa Tim9-Tim10 complex in the tim10-1 mutant, the complex was not detected by immunoblot analysis (FIG. 7B). Moreover, in vitro import of the TIM22 pathway substrate, AAC, was inhibited in comparison to mitochondria from the parental strain (FIG. 1B). The tim10-1 mutant thus has excellent growth properties for conducting a synthetic genetic screen with small compounds to target the TIM22 import pathway.

For subsequent testing of the compounds in biochemical assays with isolated mitochondria, a suppressor strain, designated tim10-1 tim9S, was used because growth of the tim10-1 mutant (FIG. 1A) and import of the carrier proteins were restored (FIG. 1B). Suppression in this strain is caused by a Ser-Cys mutation in Tim9; the mutated serine residue is nine amino acids after the second CX3C motif (17). Whereas the specific mechanism of suppression is not understood, the mutant Tim9 protein restored the abundance of Tim10 (FIG. 7A) and the assembly of Tim9-Tim10 complexes, albeit of aberrant sizes (FIG. 7B).

The screen was conducted with an integrated robotic system with plate scheduling. Briefly, diversity oriented commercial libraries of drug-like compounds from Chembridge and Asinex were screened against the tim10-1 strain at a concentration of approximately 10 µM. The screen encompassed a total of approximately 50,000 compounds dissolved in DMSO. Yeast in YPD medium was aliquoted into 384-well plates followed by compound addition with robotic pinning into the assay wells. DMSO was the vehicle for the small molecules, and several plate columns that contained only 1% DMSO were included as a control with the pinned compounds. As a negative control for growth, wells pinned with the mitochondrial uncoupler CCCP, which caused lethality, were also included. After 2 days of incubation at 25° C., cultures in each well were measured for optical density (O.D.) as a measure of growth. A typical reading for the positive control was $OD_{600}$=0.8. Wells in which the growth was inhibited by >50% were deemed as potential inhibitors and chosen for further analysis. Approximately 600 inhibitors from the primary screen were selected for hit confirmation and secondary screens.

To identify possible specific inhibitors of mitochondrial protein translocation from the pool of hit compounds, two counter screens were executed. In the first round, the initial hit compounds were incubated with the tim10-1 mutant and the isogenic control strain carrying an integrated version of the TIM10 gene at the leu2 locus. Small molecules that inhibited growth of the mutant but not the control strain at 10 µM were advanced to the second counter screen. In a second round, compounds were assayed for selective growth inhibition of the tim10-1 mutant, but not the tim10-1 mutant harboring a plasmid containing the wild-type TIM10-1 gene. The second counterscreen was a test for chemical genetic rescue. Compounds that showed inhibition of only the tim10-1 mutant in both counter screens were dubbed "MitoBloCK" compounds based on their potential to inhibit protein translocation in mitochondria. Of 25 potential "lead" inhibitors, MitoBloCK-1 was chosen for additional analysis.

MitoBloCK-1 Inhibits Protein Import of TIM22 Substrates into Mitochondria

MitoBloCK-1 is a tetrahydrodibenzofuran derivative that was identified from the Chembridge library (FIG. 2A). The $MIC_{50}$ for MitoBloCK-1 that inhibited growth of the tim10-1 mutant was approximately 1 µM (FIG. 2B). MitoBloCK-1 had a similar $MIC_{50}$ with another temperature sensitive am/0 mutant, tim10-73. In contrast, the $MIC_{50}$ for the isogenic control was greater than 200 µM. To understand the cell-based activity of MitoBloCK-1, we also determined the $MIC_{50}$ with other yeast mutants that also were disrupted for prd5 and snq2 (Table 1). For mutants within the TIM22 pathway, MitoBloCK-1 displayed an $MIC_{50}$ concentration of 11 µM for the tim9-3 mutant and 10 µM for the tim10-1 tim9S suppressor strain, respectively. In contrast, the $MIC_{50}$ for MitoBloCK-1 in the tim23 mutant was greater than 200 µM. Overexpression of import components, TIME, TIM9, TIM22, and TIM123, in the tim10-1 mutant did not alter the ability of MitoBloCK-1 to inhibit growth. Interestingly, strains lacking the mitochondrial genome (denoted as rho null) were also sensitive to MitoBloCK-1. Thus, MitoBloCK-1 specifically inhibited growth of the tim9 and tim10 mutants, even in the presence of the suppressing mutation in Tim9; this growth analysis suggests MitoBloCK-1 targets the Tim9-Tim10 complex.

Figure 8:
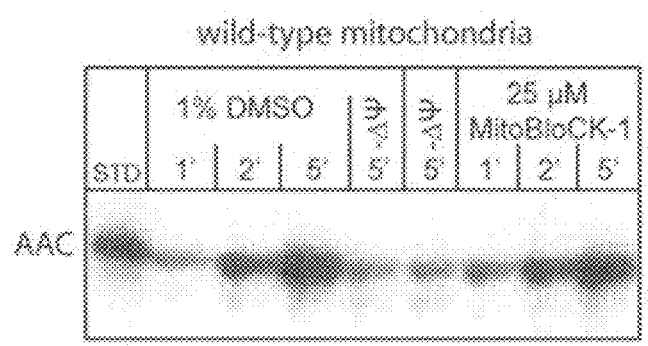
FIG. 8: shows MitoBloCK-1 does not inhibit AAC import into wild-type mitochondria. Import of AAC was performed as described in 3a into wild-type mitochondria. The rate of import was similar in the presence of the vehicle DMSO or MitoBloCK-1.

The ability of MitoBloCK-1 to inhibit import of mitochondrial precursors was tested using the in vitro import assay with radiolabeled substrates. For this analysis, mitochondria from the tim10-1 tim9S strain were used because MitoBloCK-1 inhibited growth of this strain (Table 1) and import of the model substrate, AAC, was restored in comparison to the tim10-1 mutant (FIG. 1B). An import time course was performed in the presence of the vehicle DMSO or varying concentrations of MitoBloCK-1 (FIG. 3). In the presence of DMSO, the import of the TIM22 substrate, AAC, was not inhibited. However, AAC import was markedly decreased in the tim10-1 tim9S mitochondria in the presence of 1 µM MitoBloCK-1 or greater (FIG. 3A). In contrast, MitoBloCK-1 did not inhibit import into WT mitochondria (FIG. 8). Thus, the $MIC_{50}$ in the import assays agree well with the cell growth assays (Table 1 and FIG. 2B).

Figure 9:
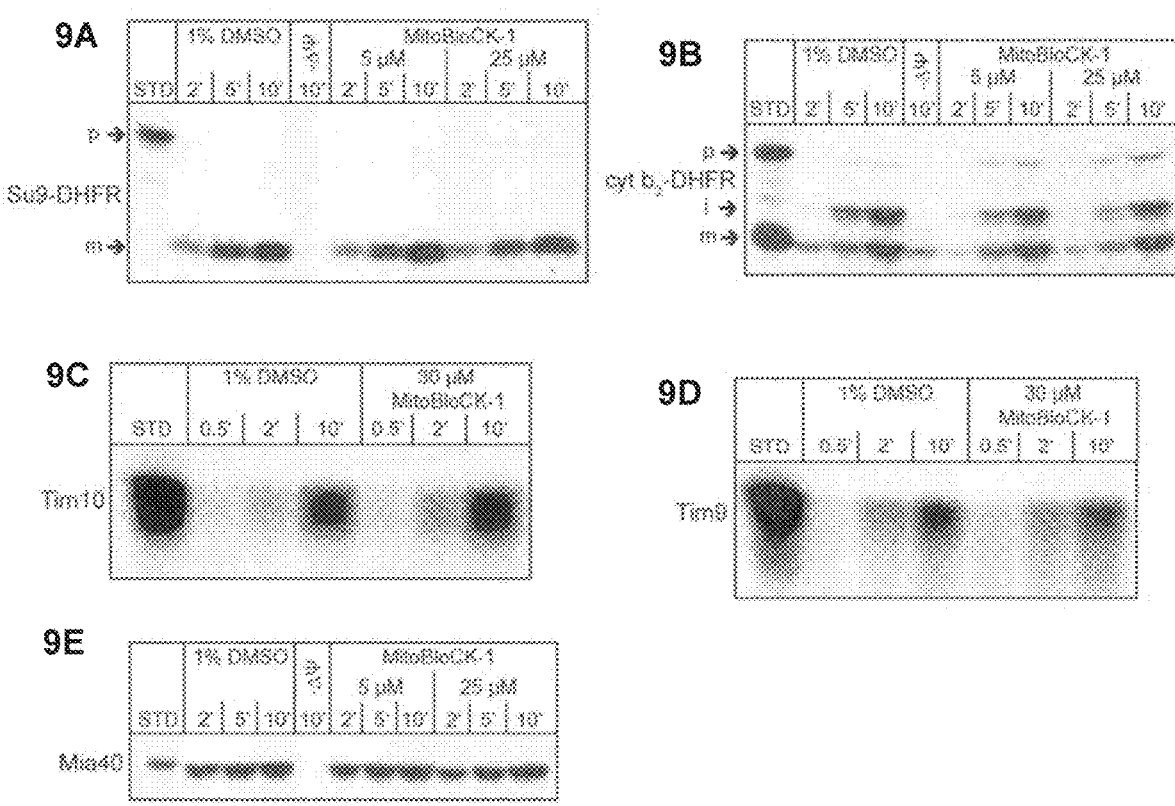
FIG. 9A-FIG. 9E: show MitoBloCK-1 inhibits the import of substrates that use the TIM22 import pathway but not the TIM23 and Mia40/Erv1 import pathways. Import assays were performed as described in FIG. 3. Precursors include (A) Su9-DHFR, (B) cytochrome b$_2$-DHFR, (C) Tim10, (D) Tim9, (E) Mia40. Panels A-B are proteins that use the TIM23 import pathway and panels C-D are intermembrane space proteins that use the Mia40 import pathway.

MitoBloCK-1 also inhibited the import of an additional carrier protein, the phosphate carrier (PiC), and the outer membrane protein Tom40, which requires the small Tim proteins for import (7) (FIG. 3B,C). However, for fusion constructs Su9-DHFR and cyt $b_2$-DHFR as well as Hsp60 that use the TIM23 pathway, MitoBloCK-1 did not impair import (FIG. 3D, 9A,B). In addition, the import of substrates Tim9, Tim10, and Mia40 that use the Mia40/Erv1 import pathway (20) was not inhibited in the presence of MitoBloCK-1 (FIG. 9C-E). Finally, MitoBloCK-1 did not inhibit the import of AAC into tim12-1 mutant mitochondria (16), indicating that import inhibition is specific for the tim10-1 mutant (FIG. 9F). Therefore, MitoBloCK-1 seems to specifically block the import of the carrier proteins and Tom40, which rely on the TIM22 pathway for translocation.

MitoBloCK-1 does not Nonspecifically Damage Mitochondria

A potential mechanism by which MitoBloCK-1 may inhibit protein translocation indirectly is by the disruption of oxidative phosphorylation or dissipation of the membrane potential. We therefore used a battery of tests to determine if MitoBloCK-1 nonspecifically altered mitochondrial integrity or function. As a first test, the ability of MitoBloCK-1 to interfere with respiration was measured (FIG. 10A-C) (21). Mitochondria were incubated in a chamber with an oxygen electrode and respiration was initiated by the addition of NADH. The rate of oxygen consumption was representative of mitochondria that were well coupled. The subsequent addition of vehicle DMSO (FIG. 10A) or 25 µM MitoBloCK-1 (~25-fold above the biochemical $MIC_{50}$) did not significantly alter the rate of respiration (FIG. 10A-C) (p=0.72). As a control, mitochondria were treated with the proton ionophore CCCP; and respiration increased drastically, indicative of uncoupled mitochondria (FIGS. 10A-C).

The membrane potential ($\Delta\psi$) of mitochondria was measured with the fluorescent dye rhodamine 123, which is taken up by mitochondria and then released when the $\Delta\psi$ is dissipated (22, 23). The relative change of fluorescence between dye uptake and release is a relative measure of the $\Delta\psi$; the dye that loads into coupled mitochondria (causing quenching and a decrease in fluorescence) is released when treated with an uncoupling agent such as CCCP (causing an increase in fluorescence). The fluorescence did not change with addition of either DMSO (FIG. 10D) or 25 µM MitoBloCK-1 (FIG. 10E) in contrast to the sharp increase in fluorescence upon CCCP addition. Taken together, the oxygen electrode and dye uptake assays support that MitoBloCK-1 is not a mitochondrial uncoupler.

Another potential mechanism that may alter protein translocation is that the small molecules may nonspecifically permeabilize mitochondrial membranes, and proteins may be released from the mitochondrion, particularly those in the IMS. We therefore incubated mitochondria with MitoBloCK-1 for 30 min followed by centrifugation (FIGS. 10F, G). Released proteins were recovered in the supernatant fraction and analyzed by immunoblot assays for key proteins and Coomassie staining for the collective release of proteins. As a positive control, MitoBloCK-2, another compound from the screen that permeabilized mitochondrial membranes, was included. Immunoblots revealed that the release of marker proteins Tom40 (OM), cytochrome c and Tim10 (IMS), AAC (IM), and Hsp60 (matrix) was similar when mitochondria were treated with MitoBloCK-1 or DMSO (FIG. 10F). In contrast, MitoBloCK-2 treatment resulted in release of the marker proteins from mitochondria, and Coomassie blue staining confirmed the extensive release mitochondrial proteins (FIG. 10G). Finally, MitoBloCK-1 did not alter steady-state stability of the Tim9-Tim10 complex because the complex migrated as a 70 kDa complex in the presence of the small molecule (FIG. 10H). From the aforementioned analysis, MitoBloCK-1 does not alter mitochondrial function or membranes nonspecifically and seems to be a specific inhibitor of protein import for the TIM22 pathway.

MitoBloCK-1 Impairs Substrate Binding by the Tim9-Tim10 Complex

Figure 4:
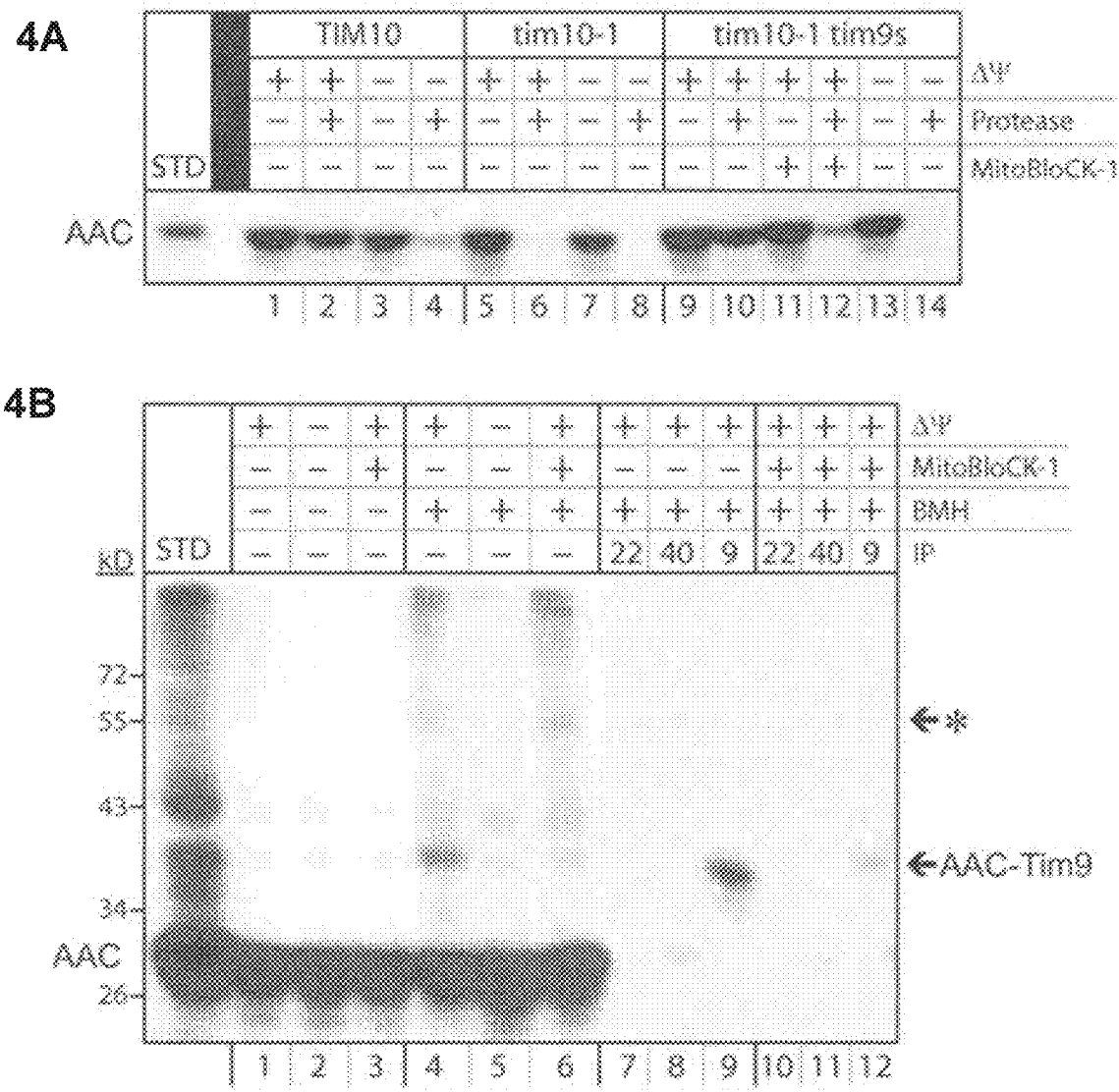
FIG. 4A-FIG. 4B: show shows MitoBloCK-1 impairs substrate binding by the Tim9-Tim10 complex. (A) AAC was imported into mitochondria isolated from TIM10, tim10-1, and suppressor tim10-1 tim9S strains in the presence and absence of a Δψ. Where indicated, MitoBloCK-1 was included in the tim10-1 tim9S mitochondria. After importing AAC 15 min, reactions were stopped with either cold buffer or trypsin (protease). (B) AAC was imported into tim10-1 tim9S mitochondria in the presence of 25 μM MitoBloCK-1 or uncoupled mitochondria (lanes 1-3), A fraction of the import reaction was treated with the irreversible cysteine crosslinker bismaleimidohexane (BMH) (lanes 4-6). BMH-treated samples were divided and aliquots were subjected to immunoprecipitation (IP) with either Tim22 (22), Tom40 (40), or Tim9 (9) polyclonal antibodies bound to protein A-Sepharose beads (lanes 7-12). In addition to the previously characterized Tim9-AAC crosslink, a second crosslink of approximately 55 kD (denoted by *) was prevalent in the MitoBloCK-1 and BMH treated sample (lane 6).

MitoBloCK-1 can be used for mechanistic studies in protein translocation. From our previous analysis of the tim10-1 and tim12-1 mutants, we showed that Tim10 was required to mediate translocation of AAC across the outer membrane and Tim12 was required at a later step to mediate insertion of the AAC into the IM (16); this analysis was determined by monitoring protease sensitivity of the AAC precursor. We adapted this methodology to determine where MitoBloCK-1 impaired AAC translocation. In wild-type mitochondria, a small fraction of the AAC was trapped in the IMS when protease was added to mitochondria in the absence of a membrane potential (FIG. 4A, lane 4). However, in tim10-1 mutant mitochondria, AAC failed to enter the IMS. Therefore, AAC that accumulated at the outer membrane was degraded upon protease addition (FIG. 4A, lane 6, 8), confirming that Tim10 is required for a very early step in protein translocation (24, 25). We added MitoBloCK-1 in this assay. In the presence of MitoBloCK-1, AAC was sensitive to protease in the presence of a membrane potential (FIG. 4A, lane 12), similar to that of the tim10-1 mutant (FIG. 4A, lane 6). This result implies that MitoBloCK-1 blocks protein translocation at a step similar to the block observed with the tim10-1 mutant, namely translocation across the outer membrane.

The early obstruction in protein translocation by MitoBloCK-1 suggested that binding between the Tim9-Tim10 complex and substrate might be abrogated. We have previously used a cross-linking and immunoprecipitation approach in tim10-1 tim9S mitochondria to show that Tim9 binds to substrate during translocation (18). MitoBloCK-1 was therefore added to import assays that were subjected to cross-linking and immunoprecipitation (FIG. 4B). In the absence of MitoBloCK-1, antibodies against Tim9 immunopreciptated a crosslinked product between Tim9 and AAC (FIG. 4B, lane 9). However, the presence of MitoBloCK-1 altered the crosslinking pattern such that the crosslink to Tim9 decreased in abundance (FIG. 4B, compare lane 4,6); instead another crosslinked band, indicative of an interaction with another protein, became more prevalent (FIG. 4B, lane 6 denoted by *). Following immunoprecipitation, the cross-linked Tim9-AAC product was decreased in the presence of MitoBloCK-1 (FIG. 4B, compare lane 9,12). Additional immunoprecipitation assays with antibodies against Tom22 and Tom40 failed to immunoprecipitate crosslinked AAC, regardless of whether MitoBloCK-1 was present. This may indicate that the homobifunctional crosslinker BMH, which is reactive to free sulfhydryls, did not have adequate sites for reactivity. As an additional control, AAC with uncoupled mitochondria (incubated with CCCP) lacked abundant crosslinks (FIG. 4B, lane 5). Therefore, this analysis supports that MitoBloCK-1 impedes protein translocation at an early stage by obstructing the substrate binding site of the Tim9-Tim10 complex.

MitoBloCK-1 can be Used to Determine Substrates of the Tim9-Tim10 Complex.

A central question about the TIM22 pathway has been the specificity of the small Tim complexes. Yeast contain both the Tim8-Tim13 complex and the Tim9-Tim10 complex and a variety of studies have suggested that they might have different substrate specificities (10, 11, 13). Most precursors including the carriers, Tim22, and Tim17 require the Tim9-Tim10 complex, whereas Tim23 and the aspartate-glutamate carriers require the Tim8-Tim13 complex. In addition, the small Tim proteins facilitate the import of outer membrane proteins (5, 7). We therefore examined whether MitoBloCK-1 could be used to determine substrate specificity of the Tim9-Tim10 complex with precursors Tim22, Tim23, and Tafazzin (FIGS. 5A-C). The import of Tim22 but not Tim23 was impaired in the presence of MitoBloCK-1, indicating that Tim23 seems to require the Tim8-Tim13 complex for translocation across the outer membrane (FIGS. 5A,B). Tafazzin is a cardiolipin remodeling enzyme that, when mutated, causes the inherited disease Barth Syndrome (26). Tafazzin import was impaired in mitochondria lacking functional Tim10 (6). When Tafazzin was imported in the presence of MitoBloCK-1, import was inhibited, confirming a role for the Tim9-Tim10 complex in the biogenesis of Tafazzin (FIG. 5C). Studies with MitoBloCK-1 thus support a role for the Tim9-Tim10 complex in the import of Tafazzin and Tim22, but not Tim23.

Taking advantage of commercially available compounds similar to MitoBloCK-1, we purchased additional compounds for an abbreviated structure-activity relationship (SAR) study (FIG. 6A). Similar compounds to MitoBloCK-1 were available in which the side chain was substituted or the tricyclic ring was changed from a dihydrobenzofuran to a carbazole. Analogs A and D were similar to MitoBloCK-1 except that the thiourea of the side chain was modified. Analogs B and C contained changes in the ring (carbazole) as well as the side chain. These compounds were tested in the import assay and Analog D was the only compound to inhibit import of AAC but required an increased concentration of 50 μM (FIG. 6A). A limited SAR analysis showed that properties of the ring structure and side chain are important for MitoBloCK-1 activity.

The long-term goal with these MitoBloCK compounds is to develop small molecules that inhibit protein translocation in mammalian systems for mechanistic studies and for developing tools to alter mitochondrial function with the objective of developing disease models. As a first step, we tested whether MitoBloCK-1 might affect general mitochondrial function in mammalian cells and measured cell viability in mammalian cells using an MTT assay (FIG. 11A). Given that mitochondrial protein import is essential for cell survival, a reduction in translocation would be expected to reduce cell viability. When cells were treated with 25 μM and 50 μM MitoBloCK-1, viability significantly decreased in a dose-responsive manner. We then tested whether MitoBloCK-1 inhibited import into isolated mouse liver mitochondria (FIG. 6B). In the presence of 25 mM MitoBlock-1, the import of AAC was inhibited. In contrast, the import of Su9-DHFR and Hsp60 was not altered in the presence of MitoBloCK-1 (FIGS. 11B,11C) Thus, the addition of MitoBloCK-1 to mammalian mitochondria disrupts the import of AAC, albeit at a higher concentration than with yeast mitochondria.

Discussion

MitoBloCK-1 is the first small molecule inhibitor that blocks the import of substrates that use the TIM22 import pathway. We started this screen with a genetic approach by developing a composite synthetic lethal screen to identify small molecules that inhibited growth of the tim10-1 mutant at the permissive temperature of 25° C. Although MitoBloCK-1 may have many potential targets within a yeast cell, we devised a battery of tests using growth analyses followed by biochemical assays to determine the specific site of inhibition by MitoBloCK-1. Because the small molecules may nonspecifically alter mitochondrial function, we determined its effect on membrane potential, respiration, and mitochondrial integrity; MitoBloCK-1 does not generally damage mitochondria. Moreover, import assays showed that import of TIM22 substrates was specifically inhibited and crosslinking and immunoprecipitation assays showed that the Tim9-Tim10 complex did not bind to substrate effectively. The combination of these assays indicated that MitoBloCK-1 inhibits an early step in protein translocation, when the Tim9-Tim10 complex binds to substrate during translocation across the outer membrane (FIG. 6C) (3, 16, 25).

The characterization of MitoBloCK-1 supports that the chemical-genetic approach is important for developing probes to study assembly of mitochondrial membranes. Mechanistic studies for the assembly of outer and IM proteins still need refinement (1). Our analysis shows that Tim9-Tim10 is important for the import of Tafazzin, Tom40, the carrier proteins, and Tim22, but not Tim23, which supports that the small Tim complexes have different substrate specificity (3, 4, 10, 13). Therefore, development of these probes will yield a new set of tools for studying mitochondrial membrane biogenesis.

A potential drawback of MitoBloCK-1 is that import is inhibited in the tim10-1 tim9S mitochondria but not wild-type mitochondria. The small SAR studies suggest that particular properties of MitoBloCK-1, such as the length of the side chain and the dihydrobenzofuran ring, may be important for its function. Therefore MitoBloCK-1 may serve as a starting point for developing more potent analogs that inhibit protein import in wild-type yeast mitochondria. In addition, the overall structure of the human small Tim proteins is highly conserved with the yeast homologs (2), and we clearly show that import into isolated mammalian mitochondria is inhibited. Following the initial import assays in mammalian mitochondria with an extended SAR approach may lead to the refinement of small molecules that inhibit function of the different mammalian small Tim proteins.

Mitochondria now have been implicated in a wide array of degenerative diseases including Parkinson's and Alzheimer's (27-30). For example, a defect in import has been linked to Alzheimer's when the amyloid precursor protein arrests in the Tom40 translocon (30). These latest developments indicate that alteration of protein translocation pathways may be important for (1) mechanistic studies in these diseases and (2) to create model systems to recapitulate the disease. Thus, having new and specific tools available such as the MitoBloCK compounds may be important for broad research in understanding how mitochondrial dysfunction contributes to disease. The development of small molecule inhibitors also serves as a technological advance over general mitochondrial inhibitors (uncouplers and inhibitors of OXPHOS) that uncouple mitochondria or irreversibly inhibit respiration.

Materials and Methods

Plasmids and Strains.

In general, a standard set of genetic and molecular techniques were used to generate the strains in this study (31, 32). Screening strains were generated based on previously characterized temperature sensitive mutants (see supplementary table 1). The snq1 and pdr5 deletions were introduced in each strain by strain mating with MDY326 or PCR-mediated deletion (33, 34). Overexpression strains were generated by transforming 2p yeast shuttle vectors carrying the gene of interest with the native promoter into the tim10-1 strain using a standard LiCl protocol (35). Transformed yeast was maintained on selective media appropriate for the plasmid's auxotrophic marker. Strains lacking mitochondrial DNA (rho null) were generated by two rounds of selection of the parent on YPD plates supplemented with ethidium bromide (40 µg/ml) followed by two rounds of single colony selection on YPD plates.

High-Throughput Screening.

A primary screen was performed using freshly streaked tim10-1 diluted in YPD to an $OD_{600}$ of approximately 0.0002 and kept on ice throughout the screening run. A Titertek multidrop (Huntsville, Ala.) was used dispense 40 µL of cell suspension to all wells of each clear 384-well plate (Greiner Bio One). After yeast suspension warmed to room temperature, a Biomek FX (Beckman Coulter) was used to pin transfer 0.5 µL of compound from 1 mM stock or DMSO to respective wells. Approximate screening concentration was 12.5 µM. All operations were performed by an automated plate scheduler to ensure consistency across the screening run. After completed compound transfer, all plates were incubated at 25° C. in a humidified incubator until the $OD_{600}$ reached approximately 0.8 in the control wells; the control consisted of the tim10-1 mutant with the vehicle 1% DMSO. Each plate was shaken in a Beckman orbital shaker to resuspend settled cells, and the $OD_{600}$ in each well was read by a Wallac Victor plate reader (Perkin Elmer). The top 600 growth inhibitory compounds were determined and assembled into two plates. Using a similar screening methodology, hit compounds were reconfirmed with the tim10-1 strain and growth inhibition was compared to the WT strain (TIM10) as well as the "rescued" strain (tim10-1 TIM10 that contained a copy of the wild-type TIM10 genes on a centromeric plasmid) strains. Compounds reordered from Asinex and Chembridge were assayed for $MIC_{50}$ using a similar automated technique in 384-well plates as previously described. Serial dilutions of purchased compounds were performed with robotic automation in 100% DMSO. Subsequently, compounds were pinned into assay plate wells containing 50 µL of the respective yeast strain in YPD medium (starting $OD_{600}$=0.0002). Growth duration and conditions were similar to the original screen.

Biochemical Assays with Mitochondria and Additional Methods.

Media and Reagents.

Media used in this study was purchased from EMD Biosciences and US Biological. Chemical reagents were from Chembridge, Asinex, and Sigma unless otherwise noted. YPD medium is 1% Bacto-yeast extract, 2% Bacto-peptone, dextrose added to 2% after sterilization. Yeast cultures for mitochondrial preparation and were either in YPEG (1% yeast extract, 2% peptone, 3% glycerol, 3% ethanol) or selective SEG medium (0.17% yeast nitrogen base, 0.5% ammonium sulfate, 3% glycerol, 3% ethanol) with appropriate amino acid dropout mixture. YPD and YPEG plates used in growth analysis included 2% agar. For MTT assays, cultured HeLa were grown in DMEM high glucose medium (Invitrogen) with glutamine, sodium pyruvate, 10% FBS, and penicillin-streptomycin (complete medium).

Analysis and Statistics.

Unless otherwise stated, all results reported are representative of three experimental replicates. Quantitative analysis was performed in GraphPad Prism 5 software (GraphPad Software, Inc.) unless otherwise stated. Statistical tests for significant deviation between samples were performed with unpaired, two-tailed t tests. The alpha threshold for significance was <0.05 for all tests. In graphs, error bars represent standard deviation from a given mean. Data transformation of rhodamine 123 fluorescence data was performed by setting the maximum OD=530 nm value from a particular trace to 100%. All fluorimetry data was scaled to the 0-100% range using GraphPad Prism's "normalize" function.

Purification of Mitochondria.

Mitochondria were purified from yeast cells grown in YPEG or selective SEG medium as described in previous studies (Glick B S, Pon L A (1995). Methods Enzymol 260:213-223). Yeast cultures were kept at a constant 25° C. with vigorous shaking during growth. After concentration was measured by BCA assay, mitochondria were stored in 25 mg/ml aliquots at −80° C. Mammalian mitochondria were isolated from 2-4 freshly excised mouse livers by differential centrifugation. Briefly, isolated livers were washed 3× with cold PBS and then suspended in 4-5 mL isolation buffer (70 mM Sucrose, 220 mM mannitol, 2mM HEPES-KOH, pH 7.4) per gram of tissue. Livers were first chopped into small pieces and then dounced 5× using a teflon dounce. Homogenized material was then centrifuged at 1,000 RPM for 10 mm in a clinical centrifuge and supernatants were transferred to fresh tubes. Centrifugation at 1,000 RPM for 10 min was then repeated and supernatants were transferred to microfuge tubes. Next, supernatant material was spun for 10 min at 800×g (this process was repeated a second time). The supernatants from these steps were subjected to a high-speed (12,000×g for 20 min) spin to pellet heavy membrane fractions. Pellets were washed in isolation buffer and spun again (12,000×g for 20 min). After the final centrifugation step, supernatants were discarded and heavy membrane fraction was resuspended in mammalian import buffer (250 mM sucrose, 5 mM magnesium acetate, 80 mM potassium acetate, 10 mM sodium succinate, 1 mM dithiothreitol, 0.1 mM ADP, 20 mM Hepes-KOH, pH 7.4) as described in Johnston A J, et al. (2002), *J Biol Chem* 277:42197-42204 and kept on ice. All subsequent imports were performed within 1 hour of isolation of mammalian mitochondria. Mitochondrial concentrations were determined by BCA assay.

Blue Native Gel Electrophoresis.

Steady-state levels of the small Tim complexes were analyzed from mitochondria isolates from TIA110,titn10-1, and titn10-1 titn9S strains following established methods (Murphy M P, et al., (2001), *Mol Cell Biol* 21:6132-6138). Approximately 200 µg of mitochondria from each strain was solubilized at 5 mg/mL in 0.16% n-dodecylmaltoside (Anatrace) for 30 minutes on ice. Following removal of insoluble material (30 minute centrifugation at 14,000 RPM), solubilized protein supernatants were analyzed by blue native gel electrophoresis on a 6 to 16% linear polyacrylamide gradient (Dekker P J, et al., (1996), *Biol Chem* 377:535-538; Schagger H, et al., (1994)m *Anal Biochem* 217:220-230; and Schagger H, von Jagow G (1991), *Anal Biochem* 199:223-231).

Import of Radiolabeled Proteins into Mitochondria and Crosslinking.

Prior to import into purified mitochondria, $^{35}$S-methionine and cysteine labeled proteins were generated with TNT Quick Coupled Transcription/Translation kits (Promega) and plasmids carrying the gene of interest. Transcription of genes was driven by either a T7 or SP6 promoter. Import reactions were conducted according to established methods. After frozen mitochondria aliquots were thawed and added to the import buffer at a final concentration of 100 µg/mL, drug or DMSO vehicle was added as indicated. A final vehicle concentration of 1% was used in all experiments.

Following 15 minute incubation at 25° C., import reactions were initiated by the addition of 5-10 L of translation mix. Aliquots were removed at intervals during the reaction timecourse and import was terminated with either cold buffer, 25 μg/mL trypsin, or a combination of both. If trypsin was added to digest unimported precursor protein, soybean trypsin inhibitor (STI) was subsequently added in excess after 15 minute incubation on ice. After a final recovery of by centrifugation (8,000×g, 5 minutes), mitochondria were disrupted in Laemmli sample buffer. Imports of membrane proteins (AAC, PiC, Tom40, Tim22, and Tim23) included a carbonate extraction step to remove proteins that had not inserted into the membrane (Koehler C M, et al. (1998), *Science* 279:369-373). Samples from import reaction time points were resolved by SDS polyacrylamide gel electrophoresis (SDSPAGE) and gels were dried prior to exposing to film.

Crosslinking and immunoprecipitation experiments were derived from procedures previously utilized (3) with the inclusion of MitoBloCK-1 or DMSO. Following import, a portion of the reaction was subjected to crosslinking with 0.5 mM bis-maleimidohexane (BMH) for 30 minutes on ice. After quenching crosslinking reactions with 1 mM β-mercaptoethanol, a fraction of each sample was subjected to immunoprecipitation with polyclonal antibodies against either Tim9, Tom22, or Tom40. For each immunoprecipitation, 20 μL of antisera was bound to 50 j.tl_, of protein A-sepharose slurry according to established protocols (Murphy M P, et al., (2001), *Mol Cell Biol* 21:6132-6138).

Membrane Potential and Oxygen Consumption.

Oxygen consumption of tim10-1 tim9S mitochondria was measured using methods previously described (8). Briefly, purified tim10-1 tim9S mitochondria aliquots (25 mg/mL) were thawed on ice and tested within 2 hours. A Clark-type oxygen electrode in a stirred, thermostatically controlled 1.5-ml chamber at 25° C. (Oxytherm; Hansatech) facilitated measurement. State II respiration was induced on a suspension of 100 μg/mL mitochondrial in 0.25 M sucrose, 20 mM KCl, 20 mM Tris-Cl, 0.5 mM EDTA, 4 mM KI-$1_2PO_4$, and 3 mM $MgCl_2$, pH 7.2 after adding 2 mM NADH. Consumption rate was monitored for approximately 2 min. Drug or DMSO was then added to a final vehicle concentration of 1% and respiration was measured for another approximately 1.5 minutes. Uncoupled respiration was achieved by adding 10 μM CCCP to the chamber.

Membrane potential measurement assays were conducted with a SPEX spectrofluorometer system (HORIBA Jobin Yvon) with a magnetically stirred cuvette held at 25° C. The quenching of rhodamine 123 fluorescence (Em, =530 nm and Ex=485 nm) was used as previously described (9) to detect changes in mitochondrial membrane potential. Purified tim10-1 tim9S mitochondrial aliquots were thawed and resuspended in respiration buffer (0.65 M mannitol, 0.3 mM EGTA, 3 mm tris-phosphate, 10 mM tris-maleate, pH 6.75). Trials were started by adding 100 nM of rhodamine 123 to respiration buffer. After a period of signal stabilization, mitochondria were added to a concentration of 100 μg/mL. Either drug or DMSO was then added to a final vehicle concentration of 1% following the establishment of baseline quenched fluorescence. Finally, mitochondria were uncoupled with 3 μM CCCP.

Cell Viability Assays.

Measurements of cell viability/toxicity were made with a MTT based toxicology assay kit (Sigma-Aldrich). HeLa cells were grown in 24-well tissue culture dishes to 80% confluency. Following this cells were either left untreated or treated with 1% DMSO or drug in complete medium for 12 hours. Following drug treatment, cells were rinsed with phosphate buffered saline and incubated with complete media with MTT solution supplement for additional 4 hours as described in manufacturer's protocols. This media was removed and 500 μL of MTT solubilization solution was added to dissolve the formazan crystals. The formazan absorbance was measured at OD=570 nm on a Wallac Victor plate reader (Perkin Elmer) along with a turbidity measurement at OD=630 nm. After turbidity subtraction, the percent viability of each cell sample was calculated as: [(absorbance of vehicle treated cells−absorbance of drug treated cells)/(absorbance of vehicle treated cells)]×100.

Miscellaneous.

Steady-state levels of mitochondrial proteins from lysed aliquots of isolated mitochondria were resolved using SDS-PAGE. Western blotting was performed using standard protocols with polyclonal antibodies raised towards highly purified antigens. Proteins were transferred to nitorocellulose membranes and immune complexes were visualized with HRP labeled Protein A in a chemiluminescence assay (Pierce). Chemiluminescent and autoradiographic imaging was performed on film unless otherwise noted. Unless otherwise stated, all results reported are representative of three experimental replicates.

TABLE 1

| Strain | Genotype | Comments | Source |
| --- | --- | --- | --- |
| tim 10-1 rho null | his3, leu2, ura3, tim 10-1: LEU2, Δtim10::HIS3, pdr5Δ 0::HGR, snq24 0::KANMX, rho null | Strain was incubated on ethidium bromide to remove mitochondrial DNA | This study |
| tim10-1 | his3, leu2, ura3, tim 10-1: LEU2, Δtim10::HIS3, pdr5Δ 0::HGR, snq2, 40::KANMX | Strain used for the primaiy screen. Original tim 10-1 strain was mated to MDY326 and sporulated. A tetrad containing the tim10-1 allele and drug pump deletions were selected. | Koehler C M, et al. (1998), *Science* 279: 369-373; this study |
| tim10-73 | ade8, his3, leu2, ura3, Δ trp1 ::LEU2, Δtim10: 1-11S3, pdr5Δ0::URA3, snq2Δ0:: KAMMX, tim10-73: TRPI CEN1, | Original tim 10-73 strain was mated to a version of MDY326-trpl. After spontlation, a tetrad containing tim10-73 allele and drug pump deletions were selected. | Koehler C M, et al. (1998), *Science* 279: 369-373; this study |
| tim9-3 | ade8, his3, leu2, trp 1, ura3, Δ tim9: :TRP1, Δpdr5::HIS3, Δsnq2::URA 3, [ptim9-3: LEU2 GEN' | Original tim9-3 strain was deleted for PDR5 and SNQ2 using PCR mediated deletion. | Leuenberger D, et al., (2003) *Traffic* 4: 144-152; this study |
| tim23-2 | ade8, his3, leu2, trp 1, ura3, tim23-2: TRP 1, Δpdr5::HIS Δsnq2::LEU2 | Original tim23-2 strain was deleted for PDR5 and SNQ2 using PCR mediated deletion. | Hwang D K, et al., (2007), *J Cell* Biol 178: 1161-1175 |

TABLE 1-continued

| Strain | Genotype | Comments | Source |
|---|---|---|---|
| TIM10 rho null | his3, leu2, ura3, TIM10: URA3, Δtim1 0:: HIS3, pdr5Δ 0::HGR, snq2Δ 0::KANMx, rho null | Strain was incubated on ethidium bromide to remove mitochondrial DNA | This study |
| TIM 10 | his3, leu2, ura3, TIM10: URA3, Δtim10:: HIS3, pdr5Δ 0::HGR, snq2Δ0:: KANMx | Strain used as primary screen control. The tim 10-1 strain used for screening was restored to wild-type at the TIM10 locus by integration of the TIM10 allele to replace the | This study |
| tim10-1 TIM10 | his3, leu2, ura3, tim 10-1: LEU2, Δtim 10::HIS3, pdr5Δ0::IIGR, snq2Δ0:: KANMx, [πTIM10: URA 3 CEN] | Centromeric plasmid carrying TIM10 under the control of its native promoter was transformed into the tim10-1 screening strain, This was used as a second control strain in | This study |
| tim 10- 1 tim9S | his3, leu2, ura3, tim 10-1: LEU2, Δtim10::HIS3, pdr5 Δ0: :HGR, snq2Δ0::KANMx, [ptim9S: URA3 CEN1] | Centromeric plasmid carrying a suppressing allele tim 9S under the control of the TIM9 promoter was transformed into the tim10-1 screening strain. | Murphy MP, et al., (2001), Mol Cell Biol 21: 6132-6138; Koehler CM, et al. (1998), EMBO J 17:6477-6486 |
| tim 10-1 TIM9 (2·) | his3, leu2, ura3, tim 10-1: LEU2, Δ tim10::HIS3, pdr5 Δ 0::HGR, snq2 Δ 0:: KANMx, [pTIM9: URA 3] 2, ul | A 2 μ plasmid carrying TIM9 under the control of its native promoter was transformed into the tim 10-1 screening strain. | This study |
| tim 10- I TIM8 (2μ)) | his3, leu2, ura3, tim10-1: LEU2, Δ tim10::HIS3, pdr5 Δ 0::HGR, snq2 Δ 0:: KANMx, [pTIM8: URA 3] 2p] | A 2 μ plasmid carrying TIM8 under the control of its native promoter was transformed into the tim 10-1 screening strain. | This study |
| tim10- I TIM/3 (2μ)) | his3, leu2, ura3, tim 10-1: LEU2, Δ tim10::HIS3, pdr5 Δ 0::HGR, snq2 Δ 0:: KANMx, [pTIM13: URA 3 2μ] | A 2μ plasmid carrying TIM13 under the control outs native promoter was transformed into the tim10-1 screening strain. Plasmid contained a high copy 21i origin of | This study |
| tim10-1 TIM22 (2μ)) | his3, leu2, ura3, tim I 0-1: LEU2, Δ tim 10: :HIS3, pdr5 Δ 0::HGR, snq2 Δ 0:: KANMx, [pTIM22: URA 3 2μ] | A 2μ plasmid carrying TIM22 under the control of its native promoter was transformed into the tim 10-1 screening strain. Plasmid contained a high copy 2μ origin of | This study |
| tim./0-1 TIM23 (2/1) | his3, leu2 ura3, tim10-1: LEU2, Δ tim10:: HIS3, pdr5 Δ 0::HGR, snq2 Δ 0:: KANMx, IPTIA122: URA 3 μ] | A 2μ plasmid carrying TIM23 under the control of its native promoter was transformed into the tim10-1 screening strain. | This study |
| tim 12-1 | his3, leu2, ura3, trp 1, ade8, tim12-1: LEU2, Δ tim 12::HIS3 | Strain used as a control for import studies. The strain is deleted for TIM I 2 and contains the tim 12-1 mutant allele integrated at the LEU2 locus. | Koehler C M, et al. (1998), Science 279: 369-373; |
| M1DY326 | his3, leu2, ura3, pdr5 Δ 0::URA, snq2 Δ 0:: KANMx | Strain with multidrug pumps deleted. | Duncan M C, et al., (2007), Proc Natl Acad Sci U S A 104:6235-6240 |
| MDY326-trpl | his3, leu2, ztra3, Δ trp I ::LEU2 pdr5 Δ 0::URA, snq2 Δ 0:: KANMx | The trp 1 allele was deleted with LEU2 in MDY326. | This study |

REFERENCES (EXAMPLE 1)

1. Chacinska A, Koehler C M, Milenkovic D, Lithgow T, Pfanner N (2009) Importing mitochondrial proteins: machineries and mechanisms. Cell 138:628-644.
2. Webb C T, Gorman M A, Lazarou M, Ryan M T, Gulbis J M (2006) Crystal structure of the mitochondrial chaperone TIM9.10 reveals a six-bladed alpha-propeller. Mol Cell 21:123-133.
3. Curran S P, Leuenberger D, Oppliger W, Koehler C M (2002) The Tim9p-Tim10p complex binds to the transmembrane domains of the ADP-ATP carrier. EMBO J. 21:942-953.
4. Curran S P, Leuenberger D, Schmidt E, Koehler C M (2002) The role of the Tim8p-Tim13p complex in a conserved import pathway for mitochondrial polytopic inner membrane proteins. J Cell Biol 158:1017-1027.
5. Hoppins S C, Nargang F E (2004) The Tim8-Tim13 complex of Neurospora crassa functions in the assembly of proteins into both mitochondrial membranes. J. Biol. Chem. 279:12396-12405.
6. Brandner K, et al. (2005) Taz1, an outer mitochondrial membrane protein, affects stability and assembly of inner membrane protein complexes: implications for Barth Syndrome. Mol Biol Cell 16:5202-5214.
7. Wiedemann N, et al. (2004) Biogenesis of the protein import channel Tom40 of the mitochondrial outer membrane: intermembrane space components are involved in an early stage of the assembly pathway. J. Biol. Chem. 279:18188-18194.
8. Leuenberger D, Curran S P, Wong D, Koehler C M (2003) The Role of Tim9p in the Assembly of the TIM22 Import Complexes. Traffic 4:144-152.

9. Beverly K N, Sawaya M R, Schmid E, Koehler C M (2008) The Tim8-Tim13 complex has multiple substrate binding sites and binds cooperatively to Tim23. *J Mol Biol* 382:1144-1156.
10. Leuenberger D, Bally N A, Schatz G, Koehler C M (1999) Different import pathways through the mitochondrial intermembrane space for inner membrane proteins. *EMBO J* 17:4816-4822.
11. Davis A J, Sepuri N B, Holder J, Johnson A E, Jensen R E (2000) Two intermembrane space TIM complexes interact with different domains of Tim23p during its import into mitochondria. *J Cell Biol* 150:1271-1282.
12. Davis A J, Alder N N, Jensen R E, Johnson A E (2007) The Tim9p/10p and Tim8p/13p complexes bind to specific sites on Tim23p during mitochondrial protein import. *Mol Biol Cell* 18:475-486.
13. Roesch K, Hynds P J, Varga R, Tranebjaerg L, Koehler C M (2004) The calcium-binding aspartate/glutamate carriers, citrin and aralarl, are new substrates for the DDP1/TIMM8a-TIMM13 complex. *Hum. Mol. Genet.* 13:2101-2111.
14. Jin H, et al. (1996) A novel X-linked gene, DDP, shows mutations in families with deafness (DFN-1), dystonia, mental deficiency and blindness. *Nat Genet* 14:177-180.
15. Koehler C M, et al. (1999) Human deafness dystonia syndrome is a mitochondrial disease. *Proc Natl Acad Sci USA* 96:2141-2146.
16. Koehler C M, et al. (1998) Import of mitochondrial carriers mediated by essential proteins of the intermembrane space. *Science* 279:369-373.
17. Koehler C M, et al. (1998) Tim9p, an essential partner subunit of Tim10p for the import of mitochondrial carrier proteins. *EMBO J* 17:6477-6486.
18. Murphy M P, Leuenberger D, Curran S P, Oppliger W, Koehler C M (2001) The essential function of the small Tim proteins in the TIM22 import pathway does not depend on formation of the soluble 70-kilodalton complex. *Mol Cell Biol* 21:6132-6138.
19. Duncan M C, Ho D G, Huang J, Jung M E, Payne G S (2007) Composite synthetic lethal identification of membrane traffic inhibitors. *Proc Natl Acad Sci USA* 104: 6235-6240.
20. Koehler C M, Beverly K N, Leverich E P (2006) Redox pathways of the mitochondrion. *Antioxid Redox Signal* 8:813-822.
21. Claypool S M, Oktay Y, Boontheung P, Loo J A, Koehler C M (2008) Cardiolipin defines the interactome of the major ADP/ATP carrier protein of the mitochondrial inner membrane. *J Cell Biol* 182:937-950.
22. Goyon V, et al. (2008) Yeast cells depleted in Atp14p fail to assemble Atp6p within the ATP synthase and exhibit altered mitochondrial cristae morphology. *J Biol Chem* 283:9749-9758.
23. Emaus R K, Grunwald R, Lemasters J J (1986) Rhodamine 123 as a probe of transmembrane potential in isolated rat-liver mitochondria: spectral and metabolic properties. *Biochim Biophys Acta* 850:436-448.
24. Koehler C M, Merchant S, Schatz G (1999) How membrane proteins travel across the mitochondrial intermembrane space. *Trends Biochem Sci* 24:428-432.
25. Ryan M T, Müller H, Pfanner N (1999) Functional Staging of ADP/ATP Carrier Translocation across the Outer Mitochondrial Membrane. *J. Biol. Chem.* 274: 20619-20627.
26. Claypool S M, McCaffery J M, Koehler C M (2006) Mitochondrial mislocalization and altered assembly of a cluster of Barth syndrome mutant tafazzins. *J Cell Biol* 174:379-390.
27. Silvestri L, et al. (2005) Mitochondrial import and enzymatic activity of PINK1 mutants associated to recessive parkinsonism. *Hum Mol Genet* 14:3477-3492.
28. Mills R D, et al. (2008) Biochemical aspects of the neuroprotective mechanism of PTEN-induced kinase-1 (PINK1). *J Neurochem* 105:18-33.
29. Hansson Petersen C A, et al. (2008) The amyloid beta-peptide is imported into mitochondria via the TOM import machinery and localized to mitochondrial cristae. *Proc Natl Acad Sci USA* 105:13145-13150.
30. Devi L, Prabhu B M, Galati D F, Avadhani N G, Anandatheerthavarada H K (2006) Accumulation of amyloid precursor protein in the mitochondrial import channels of human Alzheimer's disease brain is associated with mitochondrial dysfunction. *J Neurosci* 26:9057-9068.
31. Sikorski R S, Hieter P (1989) A system of shuttle vectors and yeast host strains designed for efficient manipulation of DNA in *Saccharomyces cerevisiae*. Genetics 122:19-27.
32. Guthrie C, Fink G R (1991) Guide to yeast genetics and molecular biology (Academic Press, San Diego, Calif.).
33. Gueldener U, Heinisch J, Koehler G J, Voss D, Hegemann J H (2002) A second set of loxP marker cassettes for Cre-mediated multiple gene knockouts in budding yeast. *Nucleic Acids Res* 30:e23.
34. Guldener U, Heck S, Fielder T, Beinhauer J, Hegemann J H (1996) A new efficient gene disruption cassette for repeated use in budding yeast. *Nucleic Acids Res* 24:2519-2524.
35. Schiestl R H, Manivasakam P, Woods R A, Gietzt R D (1993) Introducing DNA into Yeast by Transformation. *Methods* 5:79-85.

Example 2. Studies on a Small Molecule Inhibitor of Redox-Regulated Protein Translocation in Mitochondria Summary The mitochondrial disulfide relay system of Mia40 and Erv1/ALR facilitates import of the small Tim proteins and cysteine rich proteins. A chemical screen identified small molecules that inhibit Erv1 oxidase activity, thereby facilitating dissection of the disulfide relay system in yeast and vertebrate mitochondria. One molecule, MitoBloCK-6, attenuated the import of Erv1 substrates into yeast mitochondria and inhibited oxidation of Tim13 and Cmc1 in in vitro reconstitution assays. In addition, MitoBloCK-6 revealed an unexpected role for Erv1 in the carrier import pathway, namely transferring substrates from the TOM complex onto the small Tim complexes. Cardiac and somite development was impaired in MitoBloCK-6 exposed zebrafish embryos. Finally, MitoBloCK-6 induced apoptosis via cytochrome c release in human embryonic stem cells (hESCs) but not in differentiated cells, suggesting an unprecedented function for ALR in hESC homeostasis. Our target-based chemical screen validates this approach for generating newtools to dissect the mitochondrial redox system in vertebrates.

Introduction

The mitochondrion has translocons of the outer membrane (TOM) and inner membrane (TIM) to import proteins from the cytosol. Proteins with a typical N-terminal targeting sequence are imported via the TIM23 pathway, whereas polytopic inner membrane proteins use the TIM22 import pathway (Chacinska et al., 2009; Mokranjac and Neupert, 2009; Schmidt et al., 2010). In contrast, most of the proteins imported into the intermembrane space (IMS) lack a mitochondrial targeting sequence and employ diverse routes for mitochondrial import (Herrmann and Hell, 2005).

A recently identified pathway in the IMS mediates oxidation of imported proteins that require disulfide bonds to acquire their native conformation (Deponte and Hell, 2009; Koehler and Tienson, 2009; Riemer et al., 2011; Sideris and Tokatlidis, 2010; Stojanovski et al., 2008b), such as the small Tim proteins and proteins with a twin CX9C motif (Cavallaro, 2010). In the small Tim proteins, the proximal N-terminal cysteine residues serve as internal targeting sequences that are recognized by the IMS oxidoreductase Mia40 (Milenkovic et al., 2009; Sideris et al., 2009), which functions as a receptor to mediate translocation across the outer membrane (Chacinska et al., 2004). Mia40 contains a redox-active cysteine pair that is maintained in an oxidized state by the sulfhydryl oxidase Erv1 (Tienson et al., 2009). As the imported protein substrate is oxidized, electrons are passed from Mia40 to Erv1, followed by transfer to molecular oxygen or cytochrome c (cyt c) (Bien et al., 2010; Dabir et al., 2007). Subsequently, cyt c can be reoxidized by cyt c oxidase of the respiratory chain (Bien et al.) or by cyt c peroxidase (Dabir et al., 2007). Thus, Mia40 and Erv1 constitute a mitochondrial disulfide relay system that is also evolutionarily conserved.

Erv1 belongs to the Erv/ALR sulfhydryl oxidase family and homologous proteins are found in the endoplasmic reticulum (Erv2) of yeast, in the extracellular environment (Quiescin sulfhydryl oxidase, QSOX), and in the poxvirus family (E10R) (Gerber et al., 2001; Senkevich et al., 2002; Thorpe et al., 2002). In addition to protein translocation, the role of Erv1 in various cellular pathways is exemplified by a number of defects observed in cells that lack functional Erv1 protein. For example, Erv1 is required for the maturation of cytosolic iron-sulfur cluster containing proteins (Lange et al., 2001). In erv1 mutant yeast, heme maturation is impaired (Dabir et al., 2007). Also, mutations in mammalian Erv1 homolog, ALR, result in an autosomal-recessive myopathy (Di Fonzo et al., 2009), and ALR has an essential pro-survival role in the maintenance of pluripotent murine embryonic stem cells (Todd et al., 2010b).

Erv1 has several key functions in the IMS, necessitating the characterization of its homolog, ALR, to uncover basic mechanisms in mitochondrial assembly in vertebrate systems. Because Erv1 donates electrons to cyt c, Erv1/ALR may have a central role in apoptotic pathways that lead to cyt c release (Dabir et al., 2007). Classically, mitochondrial protein import has been studied using yeast genetics and biochemical assays. However, new approaches are needed to elucidate disease mechanisms and dissect essential functions in mammalian cells. Here we report a small molecule screening approach to identify Erv1 inhibitors, with the goal of developing a set of probes that can modulate the pathway quickly and recapitulate disease phenotypes. We have taken advantage of the previously developed in vitro Amplex Red assay for monitoring Erv1 activity to identify inhibitors (Dabir et al., 2007). Our results indicate that the small drug-like inhibitor characterized here is specific for Erv1/ALR and can be used to reveal normal functions and disease mechanisms in mammalian mitochondria.

Materials and Methods
High-Throughput Screen for Erv1 Modulators.

The primary chemical screen used fresh recombinant Erv1 (in buffer 30 mM Hepes, pH 7.4, 100 mM NaCl, 1 mM EDTA) at a concentration of 10 µM, which was expressed as described previously. A Titertek multidrop (Beckman Coulter) was used to dispense 25 µl Erv1 or 25 µl of catalytically inactive enzyme Erv1C133S into wells of a clear bottom 384-well plate (Greiner Bio One). A Biomek FX (Beckman Coulter) was used to pin transfer 0.5 µl of compound from 1 mM stock or DMSO to respective wells. Approximate screening

| Strain | Genotype | Source |
| --- | --- | --- |
| WT | his3 leu2 ade8 trp1 ura3 | This study |
| MDY326 | his3 leu2, ura3, pdr5Δ0::URA 3 snq2Δ0::KANMx | This study |
| Erv1-His | his3 leu2 ade8 trp1 ura3 erv1::HIS3[pERV1-10XHis: LEU2 2µ] | This study |
| erv1-12 | his3 leu2 ade8 trp1 ura3 erv1::HIS3 [perv1-12: TRP1 CEN] | This study | concentration was 12.5 µM. After completed compound transfer, all plates were incubated at 25° C. in a humidified incubator for 1 hour. A Titertek multidrop was used to dispense 15 µl of Amplex Red-horseradish peroxidase (HRP) (Sigma) mix into all wells of the 384-well plate. The final concentration of Amplex Red and HRP were 46 µM and 0.092 U/ml, respectively. The Amplex Red-HRP solution was shielded from light during the entire experiment. The plates were incubated for an additional 10 min and then 15 µl of the substrate DTT (20 µM) was added to initiate the reduction of O2 to $H_2O_2$. The plates were incubated for 12 minutes to achieve a maximal signal-to-noise ratio in the kinetic liner range. Plates were then read at an endpoint using an excitation wavelength of 545 nm and an emission wavelength of 590 nm. All operations were performed by an automated plate scheduler to ensure consistency across the screening run. We chose compounds that inhibited Erv1 activity by greater than 50%. Using a similar screening methodology as above, hit compounds were reconfirmed. Compounds that were available were ordered from Asinex and Chembridge and assayed for $IC_{50}$ using a similar automated technique in 384-well plates as previously described. Serial dilutions of purchased compounds were performed with robotic automation in 100% DMSO. Subsequently, compounds were pinned into assay plate wells containing 10 µM Erv1, Erv2, or ALR.

For $MIC_{50}$ analysis in the yeast strains, serial dilution of MitoBloCK-6 (0.5 µl) was pinned into assay plate wells containing 50 µl of yeast (Table 2) in rich ethanol-glycerol media (starting $OD_{600}$=0.0002). Plates were then incubated at 25° C. in a humidified chamber for 40 hours. Each plate was shaken in a Beckman orbital shaker to resuspend settled cells, and the $OD_{600}$ in each well was read by a Wallac Victor plate reader (Perkin Elmer).

To assess the effect of MitoBloCK-6 on $H_2O_2$ production, 25 µl of buffer (30 mM Hepes, pH 7.4, 100 mM NaCl, 1 mM EDTA) containing 2 µM, 5 µM, or 10 µM MitoBloCK-6 was aliquoted into assay well plate. 15 µl of the Amplex Red/HRP was added, and the plates were incubated at room temperature for 30 minutes. The reaction was initiated with addition of 800 nM $H_2O_2$ solution and the fluorescence was measured after 10 min.

Assays

MitoBloCK-6 was analyzed using a battery of established in vitro, yeast, mammalian cell-based, and zebrafish assays. These are described in detail in the Supplemental Data.

Plasmids and Strains

Recombinant Erv1 and Mia40 were expressed and purified under native conditions as described previously (Dabir et al., 2007; Tienson et al., 2009). Recombinant Tim13 was purified under denaturing conditions as described previously (Beverly et al., 2008). Recombinant Cmc1 was generously provided by Dr. Barrientos (Univ. of Miami). Recombinant long form ALR, residues 1 to 205, was purified under native conditions (Daithankar et al., 2010). Proteins Tim13, Mia40, Erv1 and Cmc1 were detected with polyclonal antibodies and immunoblot analysis. Table 2 lists the strains used in this study.

Media and Reagents

Media used in this study was purchased from EMD Biosciences and US Biological. Chemical reagents were from Chembridge, Asinex, and Sigma unless otherwise noted. Yeast cultures for mitochondrial preparation were grown in YPEG (1% yeast extract, 2% peptone, 3% glycerol, 3% ethanol). For MTT assays and fluorescence microscopy, cultured HeLa and HEK293 cells were grown in DMEM high glucose medium (Invitrogen) with glutamine, sodium pyruvate, 10% FBS, and penicillin-streptomycin (complete medium).

Analysis and Statistics

Unless otherwise stated, all results reported are representative of three experimental replicates. Quantitative analysis was performed in GraphPad Prism 5 software unless otherwise stated. Statistical tests for significant deviation between samples were performed with unpaired, two-tailed t-tests. The alpha threshold for significance was <0.05 for all tests. In graphs, error bars represent standard error from a given mean.

Mass Spectrometry

LC-MS experiments were carried out on a Waters Acquity UPLC connected to a Waters LCT-Premier XE Time of Flight Instrument controlled by MassLynx 4.1 software. The mass spectrometer was equipped with a Multi-Mode Source operated in the electrospray mode. Briefly, samples of MitoBloCK-6, ES-1, and ES-2 were separated using an Acquity BEH C18 1.7 um column (2.1×50 mm, Waters) and were eluted with a gradient of 0.5 mL/min water/acetonitrile with 2, 80, and 95% acetonitrile at 0.5, 2.5 and 3.5 min, respectively. Mass spectra were recorded from 80 to 2000 Daltons. All solvents were LC-MS/MS Grade and purchased from Fisher Scientific.

Purification of Mitochondria

Mitochondria were purified from yeast cells grown in YPEG as described in previous studies (Glick and Pon, 1995). Yeast cultures were kept at 25° C. with vigorous shaking during growth. Mitochondria concentration was measured by BCA assay and stored in 25 mg/ml aliquots at −80° C.

Import of Radiolabeled Proteins into Yeast Mitochondria

Prior to import into purified mitochondria, $^{35}$S-methionine and cysteine labeled proteins were generated with TNT Quick Coupled Transcription/Translation kits (Promega) and plasmids carrying the gene of interest. Transcription of genes was driven by either a T7 or SP6 promoter. Import reactions were conducted as previously described (Hasson et al., 2010). After frozen mitochondria aliquots were thawed and added to the import buffer at a final concentration of 100 μg/ml, MitoBloCK-6 or DMSO vehicle was added as indicated. A final concentration of 1% DMSO was used in all experiments. Following incubation at 25° C. for 15 min, import reactions were initiated by the addition of 5-10 μl of translation mix. Aliquots were removed at intervals during the reaction time course and import was terminated with addition either of cold buffer or 25 μg/ml trypsin, or the combination. If trypsin was added to digest non-imported precursor protein, soybean trypsin inhibitor was subsequently added in excess after 15 min incubation on ice. After a final recovery of by centrifugation (8,000×g, 5 min), mitochondria were disrupted in Laemmli sample buffer. Imports of membrane proteins (AAC and Tim23) included a carbonate extraction step to remove proteins that had not inserted into the membrane (Koehler et al., 1998a). Samples from import reaction time points were resolved by SDS-PAGE and visualized by autoradiography. Blue-native gel analysis was performed as described previously (Koehler et al., 1998b).

Oxygen Consumption Measurements

Oxygen consumption of WT mitochondria was measured using methods previously described (Claypool et al., 2008a). Briefly, purified WT mitochondria (25 mg/ml) were thawed on ice and tested within 2 hours. Oxygen consumption assays were performed with a Clark-type oxygen electrode in a stirred thermostatically controlled 1.5-ml chamber at 25° C. (Oxytherm, Hansatech). State II respiration was induced in a suspension of 100 μg/ml mitochondria in 0.25 M sucrose, 20 mM KCl, 20 mM Tris-Cl, 0.5 mM EDTA, 4 mM $KH_2PO_4$, and 3 mM $MgCl_2$, pH 7.2 after adding 2 mM NADH. Consumption rate was monitored for approximately 2 min. MitoBloCK-6 or DMSO was then added to a final vehicle concentration of 1% and respiration was measured for another approximately 1.5 min. Uncoupled respiration was achieved by the addition of 10 μM CCCP to the chamber. For assessing succinate dehydrogenase activity, respiration was induced in a suspension of 200 μg/ml mitochondria in the buffer described above after addition of 10 mM succinate. Consumption rate was monitored for approximately 3 mins. MitoBloCK-6, SAR compounds, or DMSO was then added and respiration measured for another 3 mins. Uncoupled respiration was achieved as described above.

The effect of MitoBloCK-6 or vehicle on oxygen reduction by Erv1 was assayed with the Clark-type oxygen electrode in 1 ml of air-saturated Hepes buffer (pH 7.4) (Dabir et al., 2007) containing 100 mM NaCl and 0.5 mM EDTA. Oxygen consumption was initiated by addition of Erv1 to a final concentration of 2 μM in the reaction mixture containing 2 mM DTT. To test the effect of MitoBloCK-6 or vehicle, Erv1 was pre-incubated with the desired MitoBloCK-6 concentration for 2 min before addition of DTT.

Reconstitution Studies

Reconstitution studies with reduced Tim13 were performed as described previously (Tienson et al., 2009). Briefly, 15 μM reduced Tim13 or reduced Cmc1 was incubated with 1 μM Mia40 and 1 μM Erv1 or ALR for 3 h at 25° C. Where indicated, Erv1 was pretreated with either vehicle or MitoBloCK-6 for 1 hr at 25° C. before adding to the reconstitution mix. $H_2O_2$ levels in the reconstitution assays were measured using the Amplex Red Hydrogen Peroxide/Peroxidase Assay kit according to the manufacturer's protocol (Dabir et al., 2007) (Invitrogen). In brief, Erv1 or ALR and Mia40 were mixed at concentrations mentioned above with 25 μl of the Amplex Red/horseradish peroxidase reaction mix. The reaction was initiated with the addition of reduced Tim13 or reduced Cmc1. The Erv1 or ALR-catalyzed reduction of 02 to $H_2O_2$ was measured by a FlexStation plate reader (Molecular Devices) controlled via the SoftMax Pro software package (Molecular Devices) for data acquisition. The reaction was performed at a shorter time period than the reconstitution assays because the Amplex Red assay is very sensitive (Dabir et al., 2007).

Cell Manipulations

For microscopy experiments, HeLa or HEK293 cells were transiently transfected with Su9-EGFP (Lipofectamine, Invitrogen) at 80% confluency. 12 hours post transfection, cells were co-labeled with Mitotracker red CMXRos (Invitrogen) and visualized with a microscope (Axiovert 200M Carl Zeiss) using a Plan-Fluor 63× oil objective. Images were acquired at room temperature with a charge-coupled device camera (ORCA ER, Hamamatsu Photonics) controlled by Axiovision software (Carl Zeiss). Image files were processed by Photoshop software (Adobe). Membrane potential was disrupted with 20 µM CCCP (Sigma-Aldrich).

For cyt c release assays, a cell fractionation kit (MitoSciences) was used. Briefly, HeLa or HEK293 cells were grown in 10 cm$^2$ dishes to 80% confluency and then cells were treated with DMSO or MitoBloCK-6 in complete medium for 12-16 h. To induce apoptosis as a positive control, cells were treated with 1 µM of staurosporine for 4 h. Cells were fractionated to obtain cytosolic and mitochondrial fractions; 100 µg of each fraction was analyzed by SDS-PAGE. Blots were probed with ApoTrack cyt c apoptosis antibody cocktail (MitoSciences).

Measurements for cell viability were made with a MTT based toxicology assay kit (Sigma) as described previously (Hasson et al., 2010). Briefly, HeLa cells were grown in 24-well tissue culture dishes to 80% confluency. Cells were then treated with DMSO or MitoBloCK-6 in complete medium for 12 h and reacted with MTT solution supplement for additional 4 hr as described in manufacturer's protocols. Percentage viability of each cell sample was calculated as: [(absorbance of vehicle treated cells)−(absorbance of MitoBloCK-6 treated cells)/(absorbance of vehicle treated cells)]×100.

Assays in Embryonic Stem Cells

Human embryonic stem cell (hESCs) line hSF1 was cultured in Stem Pro SFM (Gibco) supplemented with 10 ng/ml bFGF on Matrigel (BD Biosciences) coated plates under 5% CO$_2$, 95% air. Differentiation involved culturing cells in Stem Pro SFM with 10 µM retinoic acid (Acros Organics) for 4 days. Cells were treated with the specific concentration of the compounds or 1% DMSO as a control. For the induction of apoptosis, cells were exposed to 20 µM actinomycin D (Sigma) with or without 100 µM z-VAD-FMK (MP Biomedical). Following treatment, cells were fixed with 3.7% formaldehyde for indirect immunofluorescence study or lysed with Triton buffer (25 mM Tris-HCl pH 7.5, 150 mM NaCl, 1% Triton X-100, 1 mM EDTA) for analysis by SDS-PAGE. Bright field images were acquired with Exi Blue (QImaging). Immunofluorescent images were acquired with a 63× oil immersion objective on an LSM 5 PASCAL Laser Scanning Microscope (Carl Zeiss). Antibodies against cyt c (BD Pharmingen), Tom20 (Santa Cruz), cleaved caspase-3 (Cell Signaling) and poly (ADP-ribose) polymerase (Cell Signaling) were purchased from the indicated vendors. Alkaline phosphatase activity staining was performed with the leukocyte alkaline phosphatase kit (Sigma) as per manufacturer's protocol. Coomassie brilliant blue staining was performed by staining cells with Coomassie brilliant blue solution (0.25% Coomassie brilliant blue R250, 45% methanol, 10% acetic acid) for 1 hour at room temperature. Cells were washed with phosphate-buffered saline followed by visualization as described above.

Zebrafish Manipulations

Zebrafish displaying fluorescent hearts were derived from transgenic TL fish expressing a fusion of the CoxIV targeting sequence with DsRed regulated by a cmlc2 (cardiac myocyte light chain-2) promoter (Shu et al., 2007). Zebrafish used for o-dianisidine staining of red blood cells in DMSO and MitoBloCK-6 treated fish were albino lines generated from crosses of TL and TU fish. Line AB were injected with the ALR morpholino. Lines were maintained in a 14-hr light/10-hr dark cycle and mated for one hour to obtain synchronized embryonic development. Embryos were grown for 3 hpf in E3 buffer (5 mM sodium chloride, 0.17 mM potassium chloride, 0.33 mM calcium chloride, 0.33 mM magnesium sulfate) and then incubated with E3 buffer supplemented with 1% DMSO or MitoBloCK-6 for 3 days at 28.5° C. Following treatment, embryos were imaged using a Leica MZ16F fluorescent stereoscope (TexasRed filter set) at 5× magnification. Alternatively, 3-day embryos were stained with o-dianisidine [40% (v/v) ethanol, 0.01 M sodium acetate, 0.65% hydrogen peroxide, 0.6 mg/ml o-dianisidine] and incubated for 15 min in complete darkness. Embryos were then washed with E3 buffer to remove residual stain and stereoscopically imaged under white light using a Leica S8APO at 1.575× magnification. For comparison, AB embryos at the one-cell stage were microinjected with 4 ng of an ATG morpholino targeted to zebrafish ALR protein (GAGGGTTGCCAGATCTCTGT-TAAAT) (SEQ ID NO:1). Embryos were allowed to mature to 2 dpf and then imaged like the MitoBloCK-6 treated embryos; embryos were imaged at day 2 because of concerns with morpholino dilution. Images were resized to 300 dpi without resampling using Adobe Photoshop software.

Results

A Chemical Screen to Identify Inhibitors of Erv1 Oxidase Activity

We previously developed an assay to test the sulfhydryl oxidase activity of recombinant Erv1 protein based on the oxidation of a non-physiologic substrate, DTT, which produces hydrogen peroxide ($H_2O_2$) (Dabir et al., 2007). $H_2O_2$ production was measured using a standard fluorometric assay with Amplex Red and horseradish peroxidase (HRP). The assay was adapted in high throughput format and a chemical screen was conducted on an integrated robotic system with plate scheduling (FIG. 13A). Briefly, diversity oriented commercial libraries of 50,000 drug-like compounds from Chembridge (Lumsden et al., 2007; Webb, 2005), Kwon (Castellano et al., 2007), and Asinex (Lumsden et al., 2007) at 10 µM concentration were screened for inhibition of Erv1 activity. Erv1 (10 µM) was aliquoted into 384-well plates followed by compound addition with robotic pinning into the assay wells. DMSO (1%, vehicle) was included in several plate columns as a carrier control with the pinned compounds. As a negative control, 10 µM catalytically inactive Erv1 (Erv1C133S) was also aliquoted into several plate columns. Incubation of the pinned compounds with Erv1 for 1 h at 25° C. was followed by addition of Amplex Red-HRP and then DTT (20 µM) to initiate the oxidase assay. After 12 min, the reaction was in the kinetic linear range and a high signal-to-noise ratio was achieved. Fluorescence intensity was measured and reactions that were inhibited by more than 50% were picked as potential Erv1 inhibitors and selected for secondary analysis. In total, 184 primary candidate inhibitors were identified (FIG. 13B). A total of 40 plates were processed with a Z' greater than 0.8 across the screen, indicating that the screen was consistent and robust.

To eliminate false positives, a counter screen was used to test whether the small molecule compounds directly inhibited the Amplex Red-HRP assay. $H_2O_2$ (800 nM) was reacted with Amplex Red-HRP in the presence of the small molecules; this is the approximate amount of $H_2O_2$ that was produced by Erv1 during the assay. Those compounds that did not inhibit the Amplex Red assay directly and showed>50% inhibition of Erv1 activity (~29 compounds) were selected for additional characterization and designated as "MitoBloCK" compounds based on their potential to inhibit Erv1 activity. Of these potential "lead" inhibitors, MitoBloCK-6 was chosen for additional analysis. FIG. 13C verifies that MitoBloCK-6 does not directly hinder the Amplex Red-HRP reaction.

MitoBloCK-6 Inhibits Erv1/Mia40 Activity

MitoBloCK-6 is 2,4-dichloro-6-((((phenylamino)phenyl)imino)methyl)phenol) from the Chembridge library (FIG. 12A), consisting of a 3,5-dichlorosalicylaldehyde derivative. Upon reordering, MitoBloCK-6 showed the same Erv1 inhibitory activity as the original aliquot from the Chembridge library. The $IC_{50}$ for MitoBloCK-6 that inhibited Erv1 oxidase activity in the in vitro Amplex Red-HRP assay was 900 nM (FIG. 12B). We also tested MitoBloCK-6 as an inhibitor of ALR (Farrell and Thorpe, 2005) and the yeast paralog in the endoplasmic reticulum, Erv2 (Gross et al., 2002) using the in vitro Amplex Red-HRP assay. The $IC_{50}$ for MitoBloCK-6 inhibiting ALR and Erv2 was 700 nM and 1.4 µM, respectively (unpublished data).

Figure 15:
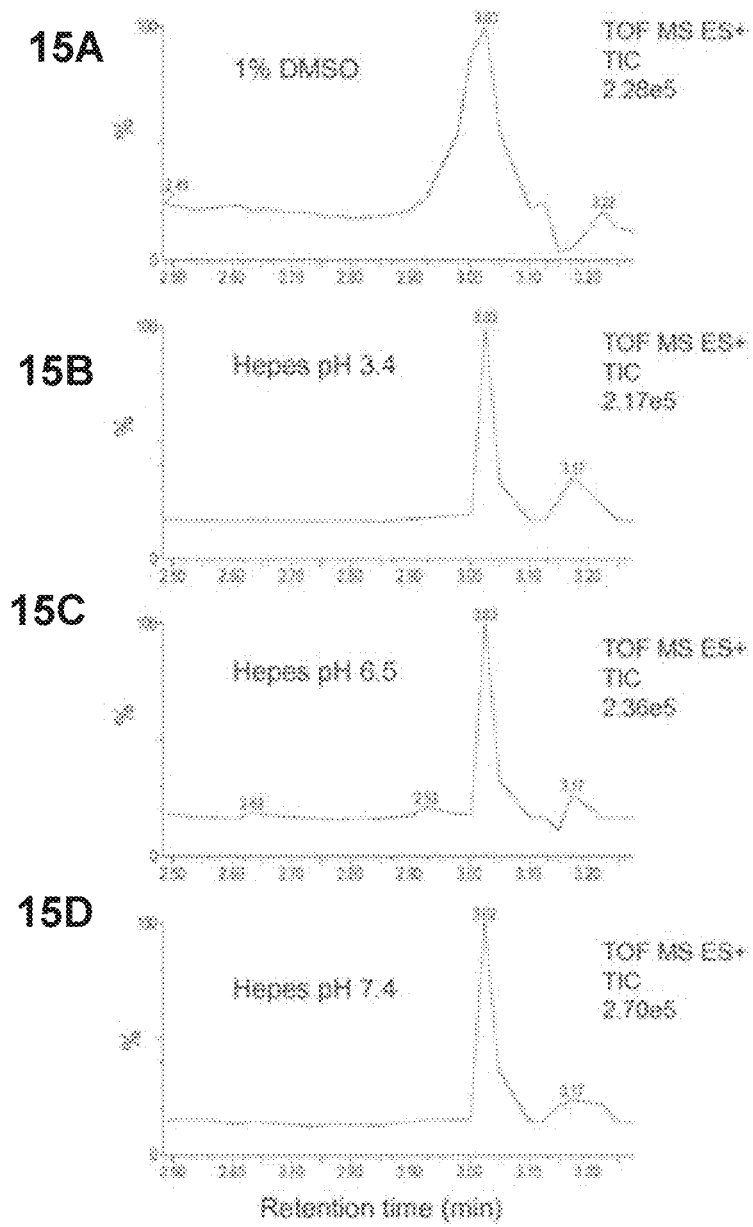
FIG. 15A-FIG. 15D: demonstrates that MitoBloCK-6 is stable. MitoBloCK-6 at a final concentration of 3 mM was incubated with screening buffer (30 mM Hepes, 100 mM NaCl, 1 mM EDTA) at pH 3.4, 6.5, and 7.4 in a reaction volume of 100 µl at room temperature for 1 hour. The sample was injected into the LC-MS and retention was monitored. As a control, 20 mM MitoBloCK-6 in 1% DMSO was also analyzed.

To determine whether MitoBloCK-6 generally impaired redox active enzymes, we investigated the oxidative folding properties of protein disulfide isomerase (PDI). MitoBloCK-6 did not inhibit the ability of PDI to reduce insulin (FIG. 14A). Because MitoBloCK-6 may potentially hinder FAD-containing enzymes, succinate dehydrogenase activity of the mitochondrial respiratory chain was measured in the presence of MitoBloCK-6 (FIG. 14B). Isolated mitochondria were incubated in a Clarke-type oxygen electrode and oxygen consumption was measured with succinate addition. The oxygen consumption rate was indicative of well-coupled mitochondria and subsequent addition of DMSO vehicle or MitoBloCK-6 did not alter the oxygen consumption rate. As controls, succinate dehydrogenase activity was disrupted with the inhibitor malonate, and CCCP addition indicated that respiring mitochondria could be uncoupled. Because a 3,5-dichlorosalicylaldehyde is a potential degradation product of MitoBloCK-6, and the 3,5-dichlorosalicylaldehyde moiety may instead inhibit Erv1 (Doom and Petersen, 2003), commercially available 3,5-dichlorosalicylaldehyde replaced MitoBloCK-6 in the in vitro Amplex Red-HRP assay (FIG. 12C). The addition of 100 µM 3,5-dichlorosalicylaldehyde did not inhibit Erv1 activity. We assessed MitoBloCK-6 stability in our screening conditions at pH 6.5 and 7.4 using liquid chromatography-mass spectrometry (LC-MS) analysis (FIG. 15). Analysis at pH 3.4 was also included, because an acidic pH favors hydrolysis of the imine linkage to release the 3,5-dichlorosalicylaldehyde (Kirdant et al., 2011). MitoBloCK-6 was stable over this pH range as supported by a similar retention time (3.03 min) and a constant area under the curve in the LC-MS analysis (FIG. 15). Thus, MitoBloCK-6 is a stable compound that specifically inhibits Erv1 activity.

Figure 16:
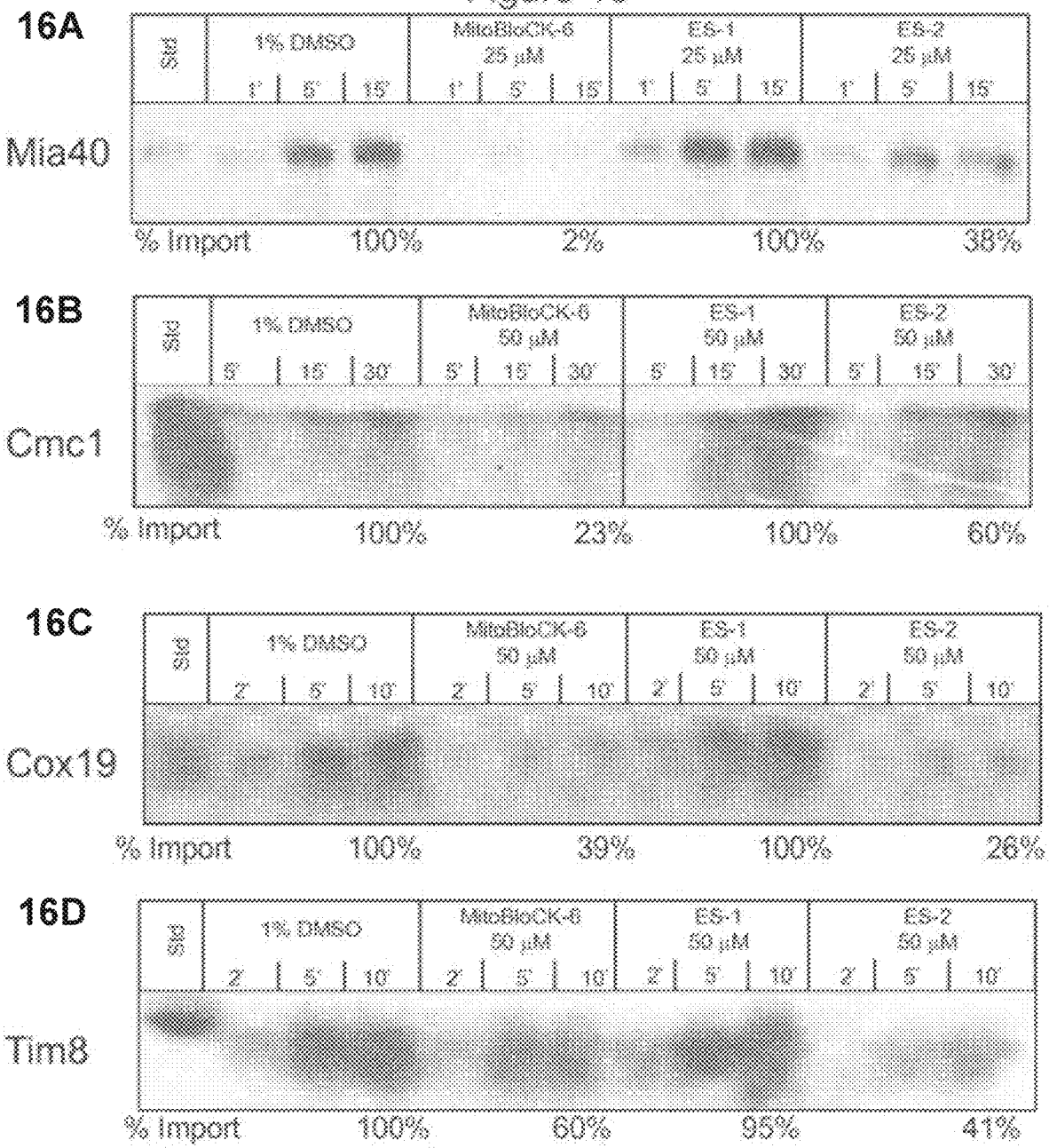
FIG. 16A-FIG. 16D: show that MitoBloCK-6 inhibits the import of substrates of the Mia40/Erv1 pathway. Radiolabeled precursors were imported into WT mitochondria in the presence of 25 or 50 μM MitoBloCK-6, 50 μM SAR compounds or the control 1% DMSO. Non-imported precursor was removed by protease treatment. A 10% standard (Std) from the translation reaction is included. Precursors included (A) Mia40, (B) Cmc1, (C) Cox19, and (D) Tim8. A 10% standard (Std) from the translation reaction is included. Import reactions were quantitated using a BioRad FX Molecular Imager and the affiliated Quantity 1 software; 100% was set as the amount of precursor imported into WT mitochondria at the endpoint in the time course.
Figure 17:
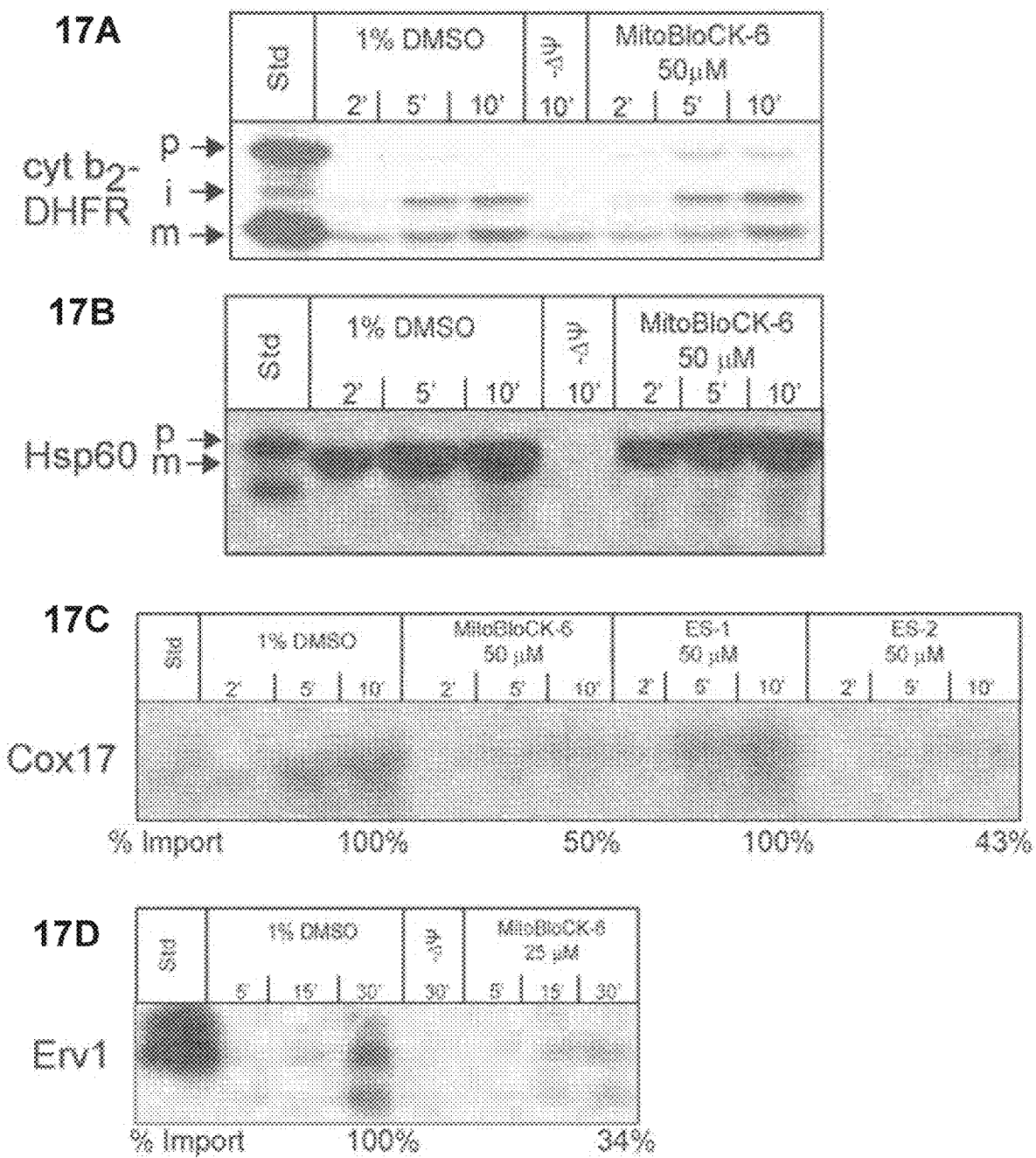
FIG. 17A-FIG. 17D: illustrate that MitoBloCK-6 inhibits import of substrates of the Erv1 oxidative folding pathway. (A) In vitro import assays were performed with TIM23 substrate cyt $b_2$-DHFR into isolated wild-type mitochondria in the presence of control 1% DMSO or 50 μM MitoBloCK-6 as described in FIG. 18C. (B) As in 'A' with Tim23 substrate Hsp60. In vitro import assays were performed into isolated wild-type mitochondria in the presence of control 1% DMSO, 25 or 50 μM MitoBloCK-6 or 50 μM ES-1 or ES-2. Substrates included (C) Cox17 and (D) Erv1. A 10% standard (Std) from the translation reaction is included. Import rates were analyzed as described in FIG. 16.
Figure 18:
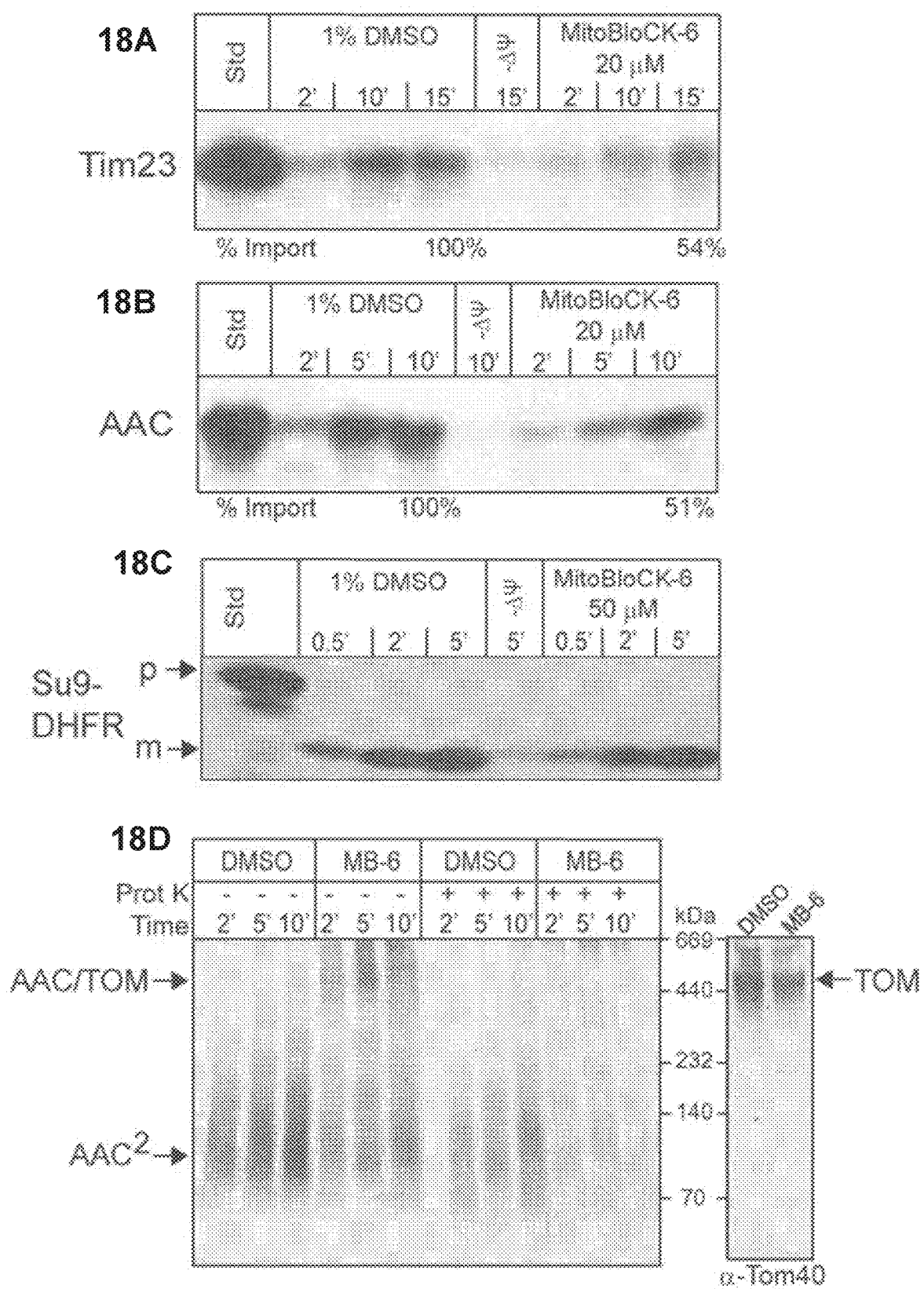
FIG. 18A-FIG. 18D: show that MitoBloCK-6 inhibits the import of substrates of the TIM22 import pathway but not the TIM23 import pathway. As in FIG. 16, import assays were performed. Precursors included TIM22 import substrates (A) Tim23 and (B) AAC. Aliquots were removed at the indicated time points and samples were treated with carbonate extraction to confirm that Tim23 and AAC were inserted into the inner membrane. TIM23 import substrate was (C) Su9-DHFR, (D) AAC was imported in the presence of DMSO or 25 μM MitoBloCK-6, aliquots were removed at indicated time points and samples were subjected to Blue-Native PAGE analysis followed by autoradiography (left panel) or incubateded with antibodies against Tom40 (right panel).

The import of Erv1 substrates was tested with an in organello import assay. Substrates included twin CX9C proteins (Mia40, Cmc1, Cox19, and Cox17), twin CX3C protein Tim8, and Erv1 (FIGS. 16, 17) (Hofmann et al., 2005; Horn et al., 2008; Riemer et al., 2011; Terziyska et al., 2007). Energized mitochondria were preincubated with 20 to 50 MitoBloCK-6 or 1% DMSO for 15 min, followed by the addition of the radiolabeled substrate. A time course assay was performed and aliquots were removed and treated with protease to remove non-imported precursors. Import of the twin CX9C proteins and Erv1 was strongly decreased, whereas the import of Tim8 was impaired by 40% upon treatment with MitoBloCK-6 compared to import in presence of 1% DMSO. We also investigated the import of additional substrates, Tim23 and AAC of the TIM22 import pathway and Su9-DHFR, cyt $b_2$-DHFR, and Hsp60 of the TIM23 import pathway (FIGS. 17, 18). At 20 µM, the import of Tim23 and AAC was decreased by approximately 50% (FIGS. 18A,B), whereas the import of TIM23 substrates was not impaired even with 50 µM MitoBloCK-6 (FIGS. 17A,B, 18C). Given that Erv1 played an unprecedented role in the import of TIM22 substrates, we investigated the import of AAC using blue-native (BN) gel analysis (FIG. 18D). Previous studies have defined the steps of AAC translocation from the cytosol to the inner membrane using mutants and biochemical manipulations (Curran et al., 2002; Ryan et al., 1999; Truscott et al., 2002). Specifically, AAC accumulates in a 500 kDa complex with the TOM complex at the outer membrane in a tim10-2 mutant or in the absence of ATP, and then is passed to the Tim9-Tim10 complex; the mature form of AAC subsequently assembles as a dimer in a 90 kDa complex in the inner membrane. After importing AAC in the presence MitoBloCK-6 or control DMSO, the mitochondria were solubilized in 1% digitonin and separated on BN gels followed by autoradiography. In the presence of DMSO, AAC accumulated in the 90 kDa complex that is indicative of an assembled AAC dimer ($AAC^2$). Moreover, the AAC dimer was protected from exogenous protease, verifying that AAC is indeed present in the inner membrane. In contrast, the addition of MitoBloCK-6 resulted in AAC accumulation in a 500 kDa complex with the TOM complex (FIG. 18D) and this AAC intermediate was sensitive to protease, confirming localization at the outer membrane. MitoBloCK-6 analysis supports a role for Erv1 in transferring AAC from the TOM complex to the Tim9-Tim10 complex in the intermembrane space. Therefore, in addition to the cysteine-rich substrates, Erv1 plays a key role in the TIM22 import pathway.

To confirm specificity of MitoBloCK-6, we purchased two additional compounds, termed ES-1 and ES-2 (Erv1-SAR), for an abbreviated structure-activity relationship (SAR) study (FIG. 12A). Whereas ES-2 inhibited Erv1 function in the in vitro assays, ES-1 did not inhibit Erv1 activity (unpublished data). When included in the import assays, ES-2 mirrored MitoBloCK-6 in its ability to impair import, but ES-1 had no effect (FIGS. 16, 17C,D). Thus, ES-2 and MitoBloCK-6 seem to specifically inhibit Erv1 function, but ES-1, like 3,5-dichlorosalicylaldehyde, did not abrogate Erv1 function.

Figure 19:
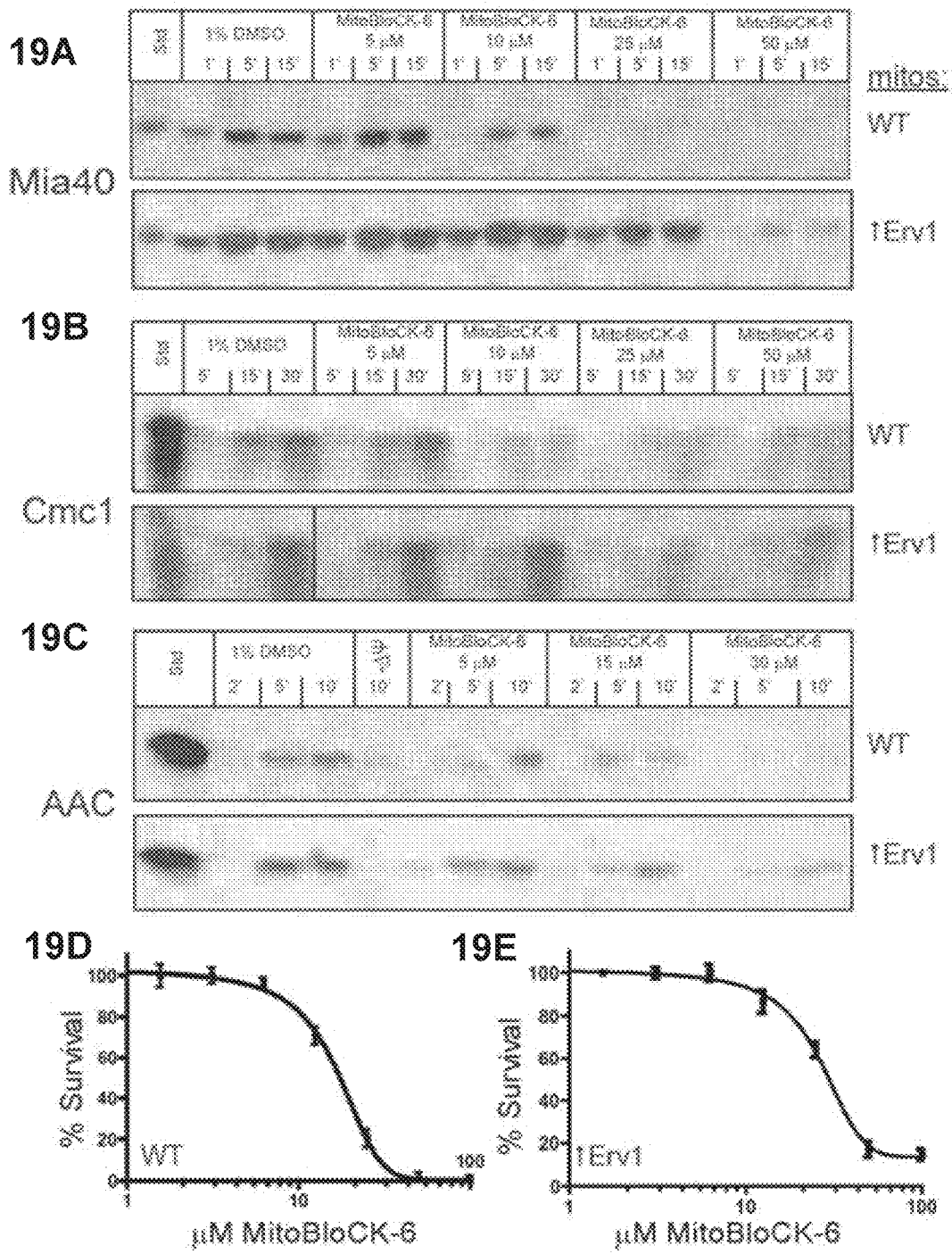
FIG. 19A-FIG. 19E: show that inhibition of import by MitoBloCK-6 is dependent on the concentration of Erv1 in mitochondria. Import assays of precursors (A) Mia40, (B) Cmc1 and (C) AAC were performed as described in FIG. 16 into mitochondria derived from wild-type yeast (WT) or yeast overexpressing Erv1 with a hexahistidine tag (↑Erv1) (Dabir et al., 2007). The concentration of MitoBloCK-6 was varied from 5 to 50 μM as indicated. A 10% standard (Std) from the translation reaction was included. (D) $MIC_{50}$ analysis of the WT yeast strain lacking the drug pumps (Δpdr5 Δsnq2) with varying concentrations of MitoBloCK-6. Average % survival±SEM of n=6 trials. (E) As in 'D', $MIC_{50}$ analysis of the Δpdr5 Δsnq2 yeast strain that overexpresses Erv1-His from a high-copy plasmid (↑Erv1).

To confirm that mitochondrial Erv1 is the target of MitoBloCK-6, an increased abundance of Erv1 should require an increased MitoBloCK-6 concentration to inhibit protein import. Previously, we designed a yeast strain in which Erv1 with a C-terminal hexahistidine tag (designated 1Erv1) was expressed from a high copy plasmid (Dabir et al., 2007).This strain contained an approximate 5-fold increase in Erv1 with no aberrant phenotypes detected. The import of Mia40, Cmc1, and AAC proteins was tested in isolated WT and ↑Erv1 mitochondria. For Mia40 and Cmc1, the concentration of MitoBloCK-6 that was required to inhibit import increased from 10 µM to 50 µM (FIGS. 19A,B). A similar trend was detected for AAC import, with a concentration increase from 15 µM to 30 µM (FIG. 19C). Combined, the data strongly support that Erv1 is the target of MitoBloCK-6.

To evaluate the cell-based activity of MitoBloCK-6, we also determined the $MIC_{50}$ with the Δpdr5Δsnq2 yeast strain in which the genes for the multi-drug resistance pumps PDR5 and SNQ2 were disrupted in the wild-type strain (Duncan et al., 2007; Hasson et al., 2010). Deletion of these pumps increases the steady state intracellular concentration of drugs in yeast. The $MIC_{50}$ was 15.2 μM (FIG. 19D), which is similar to the $IC_{50}$ concentration that inhibited protein import. As in the import assays (FIGS. 19A-C), we measured the $MIC_{50}$ with the Δpdr5Δsnq2 strain overexpressing Erv1 from a high copy plasmid (Dabir et al., 2007). The $MIC_{50}$ increased to 28.3 μM when Erv1 was overexpressed (FIG. 19E).

Mitochondria are not Damaged by MitoBloCK-6

Figure 20:
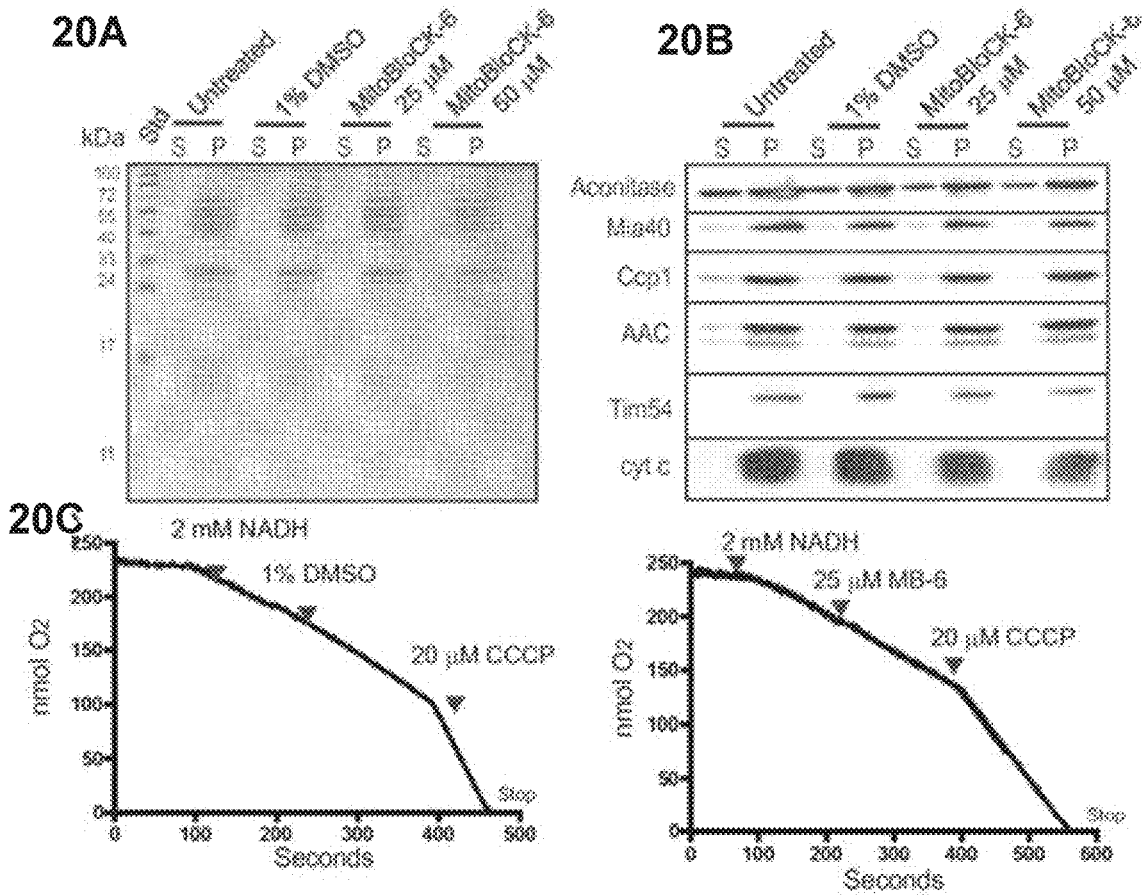
FIG. 20A-FIG. 20D: show that MitoBloCK-6 does not impair general mitochondrial function. (A) 25 or 50 μM MitoBloCK-6 (MB-6) was added to purified 100 μg/ml WT mitochondria for 30 min at 25° C. in import buffer and released proteins (S) were separated from mitochondria (P) by centrifugation. Proteins were visualized by Coomassie staining. (B) As in 'A', except immunoblot analysis was performed to determine the fractionation for aconitase, Mia40, Ccp1, AAC, Tim54, and cyt c. As a control, treatment with the vehicle (1% DMSO) was included. (C) Respiration measurements were performed with a Clark-type oxygen electrode using 100 μg/ml WT mitochondria in the presence of 1% DMSO or MitoBloCK-6. Respiration was initiated with NADH addition. 25 μM MitoBloCK-6 or 1% DMSO was added once steady-state respiration had been established. As a control, CCCP was added to uncouple the electron transport chain. (D) The Clark-type oxygen electrode was used to directly measure oxygen consumed when 10 μM Erv1 oxidized DTT in the presence of MitoBloCK-6 or the control 1% DMSO. The rate (nmol O2 consumed per second) was calculated in the linear portion of the reaction.

A potential mechanism by which MitoBloCK-6 could alter protein translocation is to nonspecifically permeabilize membranes, resulting in the release of mitochondrial proteins, particularly from the IMS. We have previously shown that MitoBloCK-2, an inhibitor of the TIM22 import pathway, nonspecifically permeabilizes mitochondrial membranes (Hasson et al., 2010). We incubated energized mitochondria with 1% DMSO or MitoBloCK-6 followed by centrifugation. Released proteins were recovered in the supernatant fraction and analyzed by Coomassie staining for the collective release of proteins (FIG. 20A) and by immunoblot assay for key proteins (FIG. 20B). The results from Coomassie staining indicated that MitoBlock-6 did not alter mitochondrial membrane integrity, because proteins were not released into the supernatant fraction (FIG. 20A). Similarly, immunoblot analysis showed that marker proteins aconitase (matrix), AAC and Tim54 (inner membrane), and IMS proteins Mia40, Ccp1, and cyt c were not released with MitoBloCK-6 or DMSO treatment (FIG. 20B).

Another potential mechanism by which MitoBloCK-6 may disrupt protein translocation is indirect, by dissipation of the membrane potential (Δψ) or disruption of oxidative phosphorylation, both of which can be measured with a Clark-type oxygen sensing electrode (FIG. 20C) (Claypool et al., 2008b). Isolated mitochondria were incubated in a 0.5 ml chamber at 25° C. with an oxygen electrode and respiration was initiated with NADH. The measured oxygen consumption rate was indicative of well-coupled mitochondria. The subsequent addition of DMSO vehicle or MitoBloCK-6 did not alter the oxygen consumption rate. As a control, mitochondria were treated with the protonophore carbonyl cyanide m-chlorophenylhydrazone (CCCP) and respiration increased drastically, indicative of uncoupled mitochondria (FIG. 20C). Taken together, MitoBloCK-6 does not alter mitochondrial function or disrupt mitochondrial integrity and functions biochemically as a specific inhibitor of Erv1.

MitoBloCK-6 Impairs Substrate Oxidation

Figure 21:
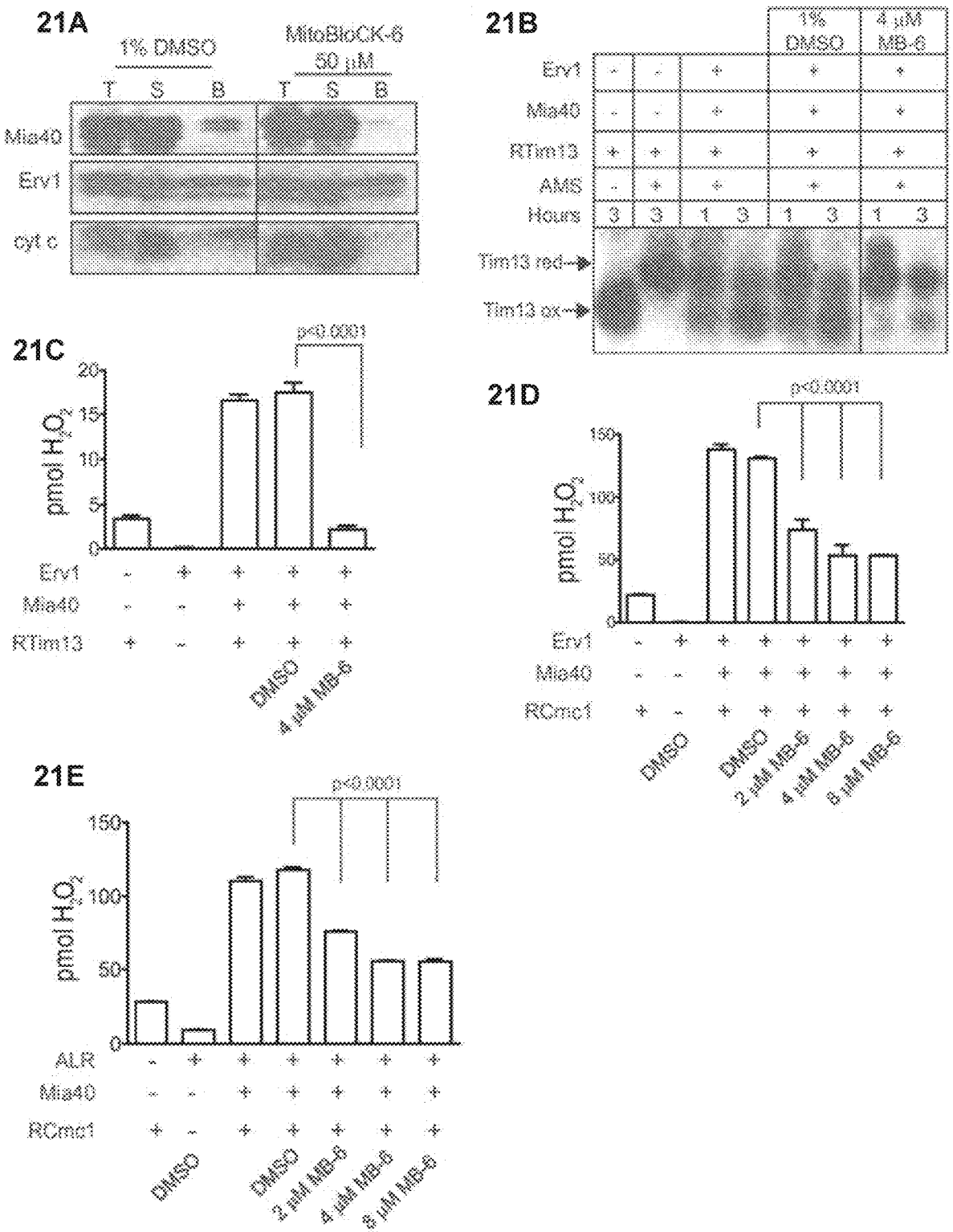
FIG. 21A-FIG. 21E: demonstrate that MitoBloCK-6 impairs substrate oxidation in vitro and disrupts Erv1 binding. (A) Mitochondria from a strain expressing C-terminal histidine-tagged Erv1 were incubated with 50 μM MitoBloCK-6 or 1% DMSO for 30 min at 25° C. followed by solubilization in 1% digitonin buffer. As a control, 100 μg of extract was withdrawn (T), and 500 μg lysate was incubated with $Ni+^2$-agarose beads. The beads were washed and bound proteins (B) were eluted with SDS-PAGE sample buffer. To test effectiveness of binding, 100 μg of the unbound protein fraction (S) was also included. Proteins were analyzed by immunoblotting with polyclonal antibodies against Mia40, Erv1, and cyt c. (B) Recombinant Erv1 was preincubated with MitoBloCK-6 or 1% DMSO for 1 hr at 25° C. and then Erv1 (1 μM) was incubated with reduced Tim13 (15 μM) and Mia40 (1 μM) in a time course assay (Tienson et al., 2009). Aliquots were removed at the indicated times and free thiols on Tim13 were modified with AMS addition. Oxidized and reduced Tim13 were detected by non-reducing SDS-PAGE and immunoblotting with antibodies against Tim13. (C, D, E) The same reconstitution assay was performed as in 'B' with reduced Tim13 (C) or reduced Cmc1 (D,E) or mammalian ALR (E) and $H_2O_2$ production was monitored over a 30-min time period with the indicator Amplex Red and displayed as pmol $H_2O_2$ (n=3).

To determine how MitoBloCK-6 inhibited Erv1 function, we investigated whether MitoBloCK-6 altered Erv1 interactions with partner proteins in isolated mitochondria (FIG. 21A). MitoBloCK-6 was preincubated with mitochondria isolated from the Erv1-His strain followed by solubilization in 1.0% digitonin and Erv1-His was purified with Ni' agarose. In DMSO treated cells, a small fraction of the Mia40 and half of the cyt c co-purified with Erv1, as reported previously (Tienson et al., 2009). However, in the presence of MitoBloCK-6, binding of Mia40 and cyt c to Erv1 was decreased by 75% and 95% respectively (FIG. 21A).

If MitoBloCK-6 interferes with Mia40-Erv1 binding, then the oxidation of substrates may be inhibited in vitro. We therefore evaluated Tim13 oxidation and subsequent production of $H_2O_2$ in vitro (FIG. 21B) (Tienson et al., 2009). Erv1 was preincubated with DMSO or MitoBloCK-6 for 1 h at 25° C. Then, the oxidation of Tim13 was reconstituted by incubating reduced Tim13 with catalytic amounts of Erv1 and Mia40 in an aerobic environment. Oxidation was monitored over a time course by the addition of 4-acetamido-4-maleimidylstilbene-2, 2-disulfonic acid (AMS) followed by non-reducing SDS-PAGE and immunoblot analysis with antibodies against Tim13. AMS addition causes an increase in molecular mass of 0.5 kDa per addition to a cysteine residue. In the presence of DMSO, reconstitution proceeded normally and approximately 80% was oxidized after three hours. By contrast, only 15% of Tim13 was oxidized in the presence of MitoBloCK-6 (FIG. 21B). As Tim13 was oxidized, $H_2O_2$ production was monitored using the Amplex Red-HRP assay (FIG. 21C) (Tienson et al., 2009). The addition of MitoBloCK-6 caused a significant decrease in $H_2O_2$ production compared to the control reactions. We also tested the oxidation of Cmc1 (Horn et al., unpublished data), a substrate of Mia40/Erv1 pathway, with Erv1 (FIG. 21D) and ALR (FIG. 21E). An increase in MitoBloCK-6 concentration correlated with a dose-dependent decrease in $H_2O_2$ production. Thus, MitoBloCK-6 specifically blocks the oxidation of Tim13 and Cmc1 in vitro for both Erv1 and ALR.

As an additional test for MitoBloCK-6 inhibition of Erv1 oxidase activity, we measured the oxygen consumption rate by Erv1 with an oxygen electrode in the presence of excess DTT (Dabir et al., 2007). When Erv1 was added alone or with DMSO, the oxygen consumption rate was similar (FIG. 20D). By contrast, the addition of MitoBloCK-6 resulted in a concentration-dependent decrease in the oxygen consumption rate. Results from these analyses show that MitoBloCK-6 selectively inhibits Erv1 and ALR oxidase activity in vitro.

MitoBloCK-6 Inhibits ALR Function in Vertebrate Mitochondria

The long-term goal in developing the MitoBloCK compounds is to adapt them for studies in vertebrate mitochondria, such as recapitulating biochemical phenotypes similar to those in cells derived from patients with mutations in ALR (Di Fonzo et al., 2009). In addition, MitoBloCK-6 may be useful for studies of apoptosis, iron sulfur cluster and heme export (Dabir et al., 2007), and cell differentiation (Todd et al., 2010b), because ALR has been implicated in these pathways. Since MitoBloCK-6 inhibits ALR oxidase activity in vitro, we asked whether MitoBloCK-6 disrupts mitochondrial function in mammalian cells by investigating mitochondrial morphology, a general readout for mitochondrial defects. HeLa cells were transiently transfected with mitochondrial matrix targeted Su9-EGFP and co-labeled with Mitotracker-Red (FIG. 23A). Cells were treated with 50 μM MitoBloCK-6 for 12-16 h and mitochondrial morphology and integrity was visualized by microscopy. In cells treated with DMSO, Su9-EGFP co-localized with Mitotracker staining and the mitochondrial network was distributed as in the untreated cells. However, the addition of CCCP caused the mitochondrial network to collapse around the nucleus. MitoBloCK-6 addition did not disrupt the mitochondrial network (FIG. 23A), even at concentrations up to 100 μM MitoBloCK-6 (unpublished data). We also examined cell viability with a 1-(4, 5-dimethylthiazol)-3, 5-diphenylformazan (MTT) assay (FIG. 23B). MitoBloCK-6 (100 μM) did not significantly reduce cell viability. In addition, treatment of HEK293 cells with MitoBloCK-6 showed similar results (unpublished data). Because Erv1 passes electrons to cyt c, ALR may play a role in apoptosis in mammalian cells. Therefore, we queried specifically whether cyt c was released in cells exposed to MitoBloCK-6

(FIG. 23C). Cells incubated with a positive control, staurosporine, showed cyt c release and detection in the cytoplasmic fraction as an indication of apoptosis. However, 50 µM MitoBloCK-6 treatment for 12-16 h failed to initiate cyt c release (FIG. 23C). Whereas MitoBloCK-6 inhibits ALR function in vitro, this inhibitory activity is surprisingly lacking in HeLa and HEK293 cells ALR was identified in a set of common genes that are enriched in embryonic, neuronal, and hematopoietic stem cells (Ivanova et al., 2002; Ramalho-Santos et al., 2002), and ALR has a pro-survival role in maintaining pluripotent embryonic stem cells (Todd et al., 2010a). Thus, ALR may have a specific and different role in pluripotent stem cells than in differentiated cells, such as HeLa and HEK293 cells. Therefore, we determined whether MitoBloCK-6 affected hESC survival. HSF1 hESCs and normal human dermal fibroblasts (NHDFs), which represent a differentiated cell type, were exposed with 20 µM MitoBloCK-6 or 0.1% DMSO and visualized using brightfield microscopy (FIG. 24A), including staining with Coomassie brilliant blue to visualize colony morphologies (FIG. 24B) (Mochizuki and Furukawa, 1987). MitoBloCK-6 exposure resulted in marked HSF1 cell death, whereas DMSO exposure did not cause cell death or alter overall colony morphology. MitoBlock-6 may trigger stem cell apoptosis. Release of cyt c was examined in HSF1 cells exposed to MitoBloCK-6 (FIG. 22A) using antibodies against cyt c and visualized by fluorescence microscopy (Waterhouse et al., 2001). MitoBloCK-6 addition resulted in a shift in cyt c localization from mitochondria (marked with Tomm20) into the cytosol (shown as diffuse staining that did not overlap with Tomm20 staining). Quantification indicated that the number of cells in which cyt c was released was similar with addition of MitoBloCK-6 or Actinomycin D, a known apoptosis inducer (FIG. 22B). In addition, downstream events in apoptosis, poly ADP-ribose polymerase (PARP) and caspase-3 cleavage were also detected with MitoBloCK-6 exposure (FIG. 22C).

To confirm that MitoBloCK-6 specifically inhibited the survival of hESCs and not of differentiated cells, HSF1 cells were induced to differentiate with 10 µM retinoic acid followed by MitoBloCK-6 exposure (FIG. 24). Again, the images show that colony morphology remained intact when HSF1 cells were differentiated with retinoic acid treatment and cells did not die. To assess the earliest time point at which MitoBloCK-6 perturbed hESC viability, a time course assay was performed and hESCs were stained for alkaline phosphatase activity (Shamblott et al., 1998). hESC viability started to decline after 5 hours post treatment (FIG. 22D). To confirm the specificity of MitoBloCK-6, the 20 µM SAR compounds ES-1 and ES-2 were applied to hESCs and stained for alkaline phosphatase activity. Whereas ES-1 had no effect on cell growth (FIG. 22E), ES-2 inhibited cell growth similar to MitoBloCK-6 (unpublished data). Taken together, MitoBloCK-6 does not inhibit mitochondrial function in differentiated cells, but hESCs were susceptible to MitoBloCK-6 and apoptosis was induced. The data confirm a key role for ALR in hESC maintenance and show that MitoBloCK-6 is a unique small molecule reagent that identifies this function.

Figure 25:
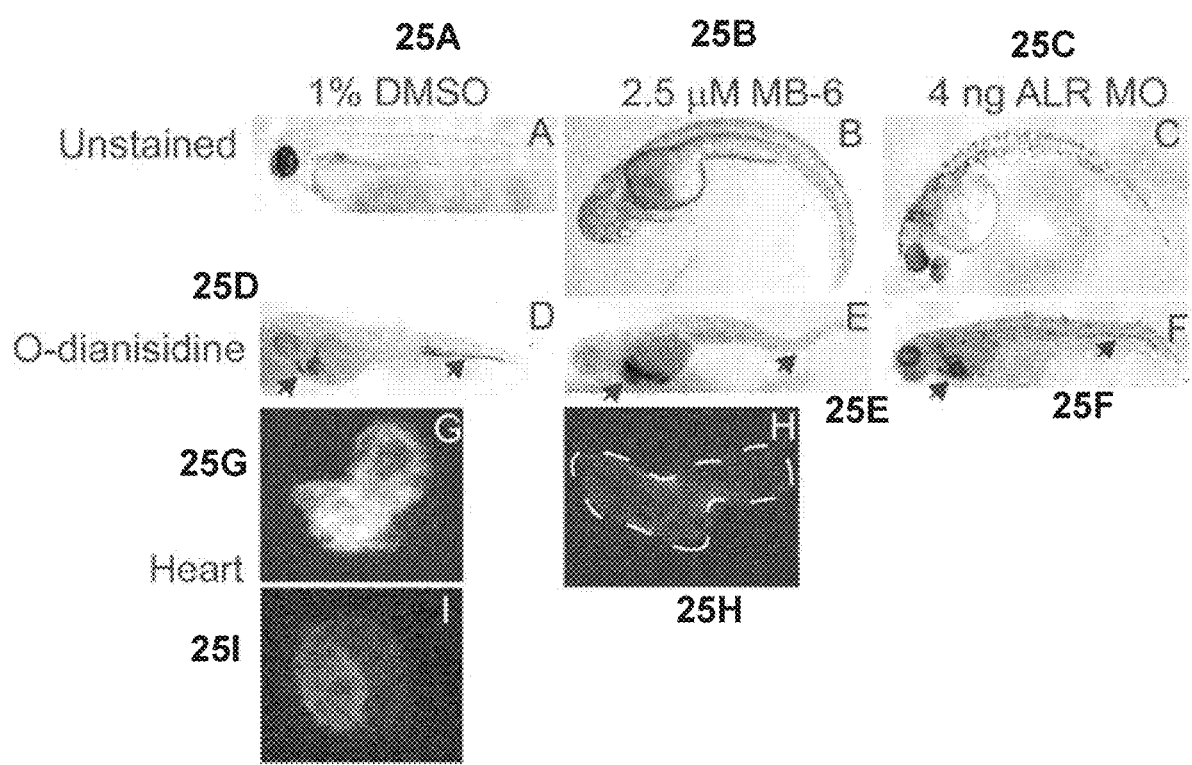
FIG. 25A-FIG. 25I: show that MitoBloCK-6 treatment impairs somite and cardiac development in zebrafish. Embryos (3 hpf) were treated with 2.5 μM MitoBloCK-6 (B, E, H) or 1% DMSO (A,D,G) or embryos were injected with an ATG morpholino against ALR (C,F). Development was visualized by microscopy at 72 hpf (A-B) or 48 hpf (C). Erythrocytes were visualized by o-dianisidine staining at 72 hpf (D-E) or 48 hpf (F); arrows indicate regions of red blood cell accumulation in wild-type fish. Fluorescence microscopy of zebrafish hearts (72 hpf) that contained a mitochondrial-targeted DsRed included embryos treated with 1% DMSO (G), 2.5 μM MitoBloCK-6 (H), and buffer only (I).
Figure 26:
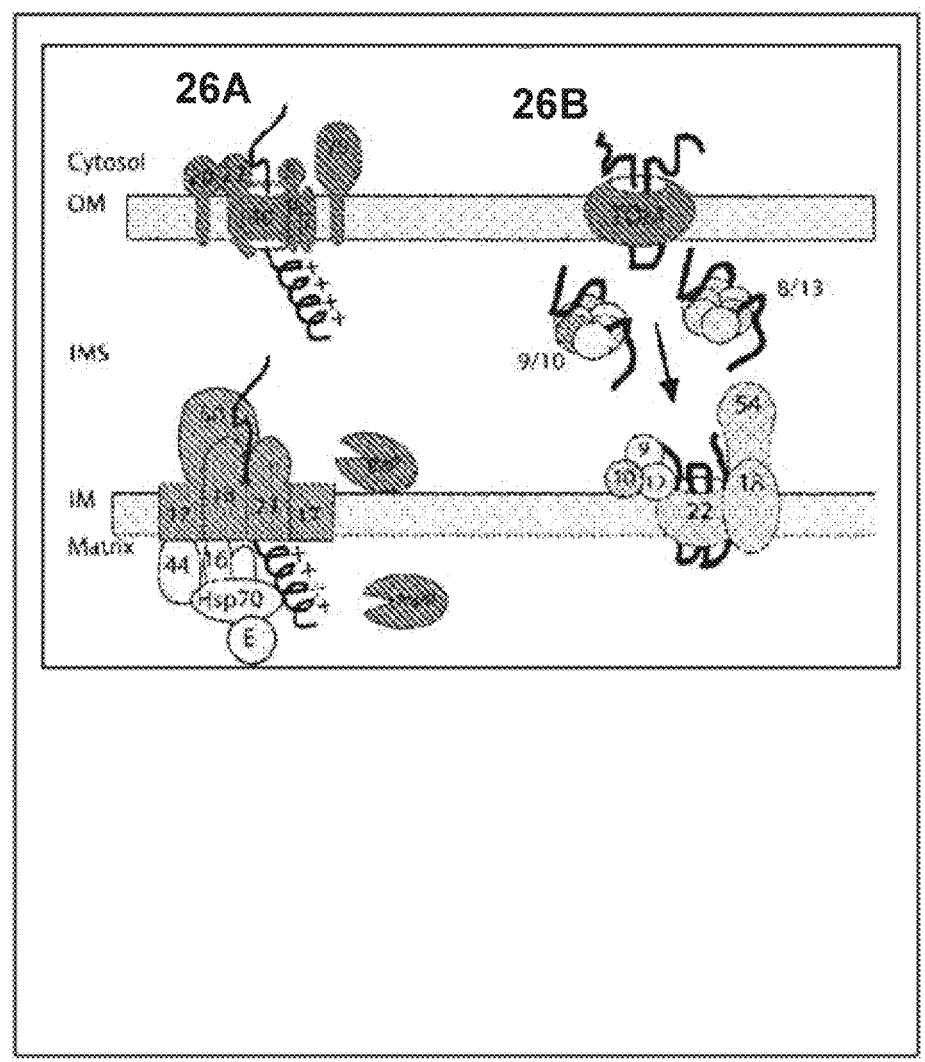
FIG. 26A-FIG. 26B: shows current understanding of the mitochondrial import pathways. (A) The general pathway (carrier independent) for polypeptide carrying a mitochondrial localization signal. (B) The carrier-dependant pathway that utilizes chaperones to translocation and integrate hydrophobic membrane proteins.

Having characterized the effects of MitoBloCK-6 in vitro and in primary cell culture systems, we applied MitoBloCK-6 to developing zebrafish embryos, which is a useful in vivo vertebrate model. The effect of MitoBlock-6 on mitochondrial function and zebrafish development was tested using previously established parameters (Mendelsohn et al., 2006; Murphey and Zon, 2006). Zebrafish embryos were placed in either 1% DMSO or 2.5 µM MitoBloCK-6 at 3 h post fertilization (hpf) and allowed to develop until 72 hpf. Higher concentrations of MitoBloCK-6 were toxic to the fish. MitoBloCK-6 but not DMSO incubated embryos displayed ventral curvature of the body and cardiac edema (FIGS. 25A,B). Furthermore, we also treated fish with MitoBloCK-6 from 3 to 24 hpf, followed by removal of MitoBloCK-6, and the zebrafish embryos were identical to those exposed to DMSO at 72 hpf, indicating that the effects of MitoBloCK-6 are reversible (unpublished data). Because ALR may play a role in FeS cluster assembly and export (Lange et al., 2001), erythropoiesis may be defective (Shaw et al., 2006). Therefore, embryos were stained with o-dianisidine, which binds to heme (Lumsden et al., 2007), as a method to visualize hematopoietic development. Whereas embryos exposed to 1% DMSO or MitoBloCK-6 showed normal hematopoiesis, embryos treated with MitoBloCK-6 showed erythrocyte pooling along the yolk sac prior to entering the lower chamber of the heart and an absence of red blood cells in the tail (FIG. 25D,E). To confirm that the observed phenotypes were specifically caused by ALR inhibition via MitoBloCK-6, 1-cell embryos were also injected with 4 ng of an ATG morpholino targeted to ALR (FIG. 25C,F). This morpholino prevents ALR translation in embryos. The phenotypes observed from the morpholino-injected embryos were identical to that of MitoBlock-6 exposure, strongly suggesting that ALR is specifically targeted. Cardiac development was also investigated in a transgenic zebrafish line in which DsRed is targeted to mitochondria under control of the heart specific cardiac myosin light chain promoter cmlc2 (FIGS. 25G-I) (Shu et al., 2007). Cardiac development at day 3 in embryos exposed to DMSO was similar to that of wild-type fish in that the heart is looped and the mitochondria are also very bright (FIGS. 25G I). In contrast, MitoBloCK-6 exposure retarded cardiac development in that the hearts failed to loop by day 2, instead becoming stringy and extended. In addition, the mitochondria were less fluorescent (FIG. 25H), which is likely indicative of dysfunctional mitochondria. This developmental defect is supported by a decreased heart rate of 50% and 25% in embryos treated with MitoBloCK-6 and the ALR morpholino, respectively. Taken together, the data strongly suggest that MitoBloCK-6 blocks ALR function in zebrafish, which inhibits somite and cardiac development.

Discussion

We have identified MitoBloCK-6 as the first selective inhibitor of the Mia40/Erv1 redox-mediated import pathway. Based on the assay in which oxidation of substrate DTT by Erv1 was inhibited, the mechanism by which MitoBloCK-6 may attenuate Erv1 activity is to potentially interfere with binding or electron transfer between Mia40, cyt c, and/or oxygen. Because the inhibitors were identified in an in vitro assay, it is possible that the small molecules might lack specificity in vivo and generally inhibit mitochondrial function. However, we have used a variety of approaches to show that MitoBloCK-6 specifically inhibits Erv1 function. MitoBloCK-6 is a stable compound and the potential breakdown product, 3,5-dichlorosalicyclaldehyde, does not inhibit Erv1 function. Instead, the hydroxyl group at the ortho-position likely stabilizes the compound (Crugeiras et al., 2009), and a similar class of molecules has been identified in a small molecule screen for inhibitors of Type III secretion (Nordfelth et al., 2005). A small SAR study also supports that similar compound ES-2 inhibits Erv1 function, but ES-1 does not. In addition, MitoBloCK-6 did not alter mitochondrial integrity and respiration; therefore, MitoBloCK-6 does not generally damage mitochondria. Instead, our biochemical assays show that MitoBloCK-6 inhibits oxidation of physiologic substrates Tim13 and Cmc1 and inhibits hydrogen peroxide production.

MitoBloCK-6 also inhibits Erv1 in isolated mitochondria, suggesting that small molecules are valuable for mechanistic studies. As expected, import assays showed that import of substrates of the Erv1-Mia40 pathway was specifically inhibited and this inhibition was dependent on steady-state Erv1 levels, because increased Erv1 expression correlated with increased MitoBloCK-6 addition. Import of CX9C proteins was reduced more than CX3C protein Tim8. Pfanner and colleagues have shown that a ternary complex is formed by the substrate, Mia40, and Erv1 (Stojanovski et al., 2008a); MitoBloCK-6 may potentially interfere with the formation of this ternary complex in a substrate-specific manner. Strong inhibition of Mia40 import by MitoBloCK-6 was also unexpected, because full-length Mia40 in yeast uses the TIM23 pathway (as in FIG. 16A), but a truncated version, similar to human Mia40, that contains the core cysteine residues uses the Mia40/Erv1 pathway (Chacinska et al., 2008). That MitoBloCK-6 blocks Mia40 import suggests that the Erv1 pathway may be important for coordinating disulfide assembly in the imported Mia40, because mia40 mutants with cysteine mutations that prevent correct disulfide bond formation are not viable (Terziyska et al., 2009). Surprisingly, import of substrates of the TIM22 pathway (AAC and Tim23) was also reduced, which suggests a broader role for the Mia40/Erv1 pathway in protein translocation. Detailed analysis of the import pathway supports a role for Erv1 in transferring the TIM22 substrates from the outer membrane TOM complex to the intermembrane space small Tim complexes (FIG. 18D). Redox regulation may be important in the TIM22 pathway, because the small Tim proteins may undergo redox regulation and the cysteine-rich protein Hot13 may also participate (Curran et al., 2004). Alternatively, MitoBloCK-6 inhibition of Erv1 may change the redox potential of the IMS, which may alter import ability of the small Tim proteins. Additional experiments will be required to determine how MitoBloCK-6 specifically alters the TIM22 pathway. Thus, MitoBloCK-6 is advantageous for mechanistic studies in protein translocation because MitoBloCK-6 acts immediately upon addition to mitochondria.

ALR has a Key Function in hESC Maintenance and Zebrafish Development

Our strategy of screening with the yeast protein Erv1 was also constructive because MitoBloCK-6 inhibited the human homolog ALR with an improved $IC_{50}$ of 700 nM. Our biochemical assays also support that MitoBloCK-6 is an effective ALR inhibitor, because the oxidation of Cmc1 was inhibited (FIG. 21E). High-resolution crystallography and NMR studies of four Erv1 family proteins, Arabidopsis thaliana Erv1 (Vitu et al., 2006), rat ALR (Wu et al., 2003), human ALR (Banci et al., 2011), and yeast Erv2 (Gross et al., 2002), reveal that the structure is highly conserved. Given that MitoBloCK-6 inhibits activity for Erv1, ALR, and Erv2, MitoBloCK-6 likely binds to a conserved region. An abbreviated SAR analysis suggests that ES2 has similar inhibitory properties as MitoBLoCK-6; both could share a similar steric volume in inhibiting Erv1. Thus, our screen has produced small molecules that work across species. This also has been shown in an in vivo screen in which we determined that MitoBloCK-1 of yeast Tim10 also inhibited Tim10 in mammalian mitochondria (Hasson et al., 2010). Furthermore, Nunnari and colleagues identified mdivi-1 as an inhibitor of the yeast fission component Drp1 (Cassidy-Stone et al., 2008). mdivi-1 also abrogates mammalian Drp1 and retards apoptosis by preventing mitochondrial outer membrane permeabilization.

Whereas MitoBloCK-6 inhibits activity of the Erv1 family in vitro, a surprising finding was that MitoBloCK-6 did not inhibit growth or function of differentiated cells such as HEK293, HeLa and COS7 cells in vivo. An initial reason may be that a factor in the media inhibited MitoBloCK-6 action. However, several types of media were tested, including the permissive hESC media with differentiated cells, and MitoBloCK-6 remained inactive. In contrast, MitoBloCK-6 specifically induced apoptosis in hESCs, suggesting ALR may have a distinct role in pluripotent stem cell maintenance. Published studies support a role for ALR in stem cells, because ALR expression is enriched in embryonic, neuronal, and hematopoietic stem cells (Ivanova et al., 2002; Ramalho-Santos et al., 2002). ALR has been reported to have a pro-survival role in maintaining mouse pluripotent embryonic stem cells by interacting with Drp1 (Todd et al., 2010a). However, Drp1 is a cytosolic protein mediating mitochondrial fission and it is not apparent how IMS-localized ALR associates with Drp1; our data supports the model that ALR inactivation by MitoBlock-6 results in cyt c release and the mitochondrial network collapses as a consequence of apoptosis (Parone et al., 2006). We and others have shown that Erv1 and ALR shuttle electrons to cyt c (Bihlmaier et al., 2007; Dabir et al., 2007; Farrell and Thorpe, 2005). In differentiated cells, approximately 85% of the cyt c population is distributed in the cristae in association with the respiratory complexes and 15% is located in the IMS in the region between the inner and outer membrane (Bernardi and Azzone, 1981); this 85% population of cyt c is released from the cristae during apoptosis in differentiated cells (Scorrano et al., 2002). However, hESC mitochondria lack numerous cristae and display decreased respiration compared to differentiated cells (Zhang et al., 2011), so the population of cyt c that associates with ALR may be the critical pool that is released during apoptosis. As a result of our preliminary finding, MitoBloCK-6 is an excellent tool to understand the contribution of mitochondrial to pluripotent stem cell function and differentiation. Additional studies are ongoing to understand how MitoBloCK-6 induces apoptosis in hESCs.

In contrast to differentiated culture cells, zebrafish provide a powerful model system for characterizing ALR function because cells are not transformed and are in their normal physiologic setting of cell-cell and cell-extracellular matrix interactions (Murphey and Zon, 2006). The embryos are also in simple buffered water, so MitoBloCK-6 uptake may be enhanced. Defects in mitochondrial biogenesis in zebrafish display varied phenotypes. Mutations in the Tomm22 import component result in defects in liver development (Curado et al., 2010) and mutations in Fe—S cluster biogenesis typically impact erythropoiesis (Shaw et al., 2006; Wingert et al., 2005). Indeed, MitoBloCK-6 also elicited gross morphologic and cardiac defects in zebrafish that were akin to ALR downregulation. Overall, characterization of MitoBloCK-6 supports that the chemical approach is valid for developing probes to study protein translocation and understand the role of protein import in development.

REFERENCES (EXAMPLE 2)

Banci, L., Bertini, I., Calderone, V., Cefaro, C., Ciofi-Baffoni, S., Gallo, A., Kallergi, E., Lionaki, E., Pozidis, C., and Tokatlidis, K. (2011). Molecular recognition and substrate mimicry drive the electron-transfer process between MIA40 and ALR. Proc Natl Acad Sci USA 108, 4811-4816.

Bernardi, P., and Azzone, G. F. (1981). Cytochrome c as an electron shuttle between the outer and inner mitochondrial membranes. J Biol Chem 256, 7187-7192.

Beverly, K. N., Sawaya, M. R., Schmid, E., and Koehler, C. M. (2008). The Tim8-Tim13 complex has multiple substrate binding sites and binds cooperatively to Tim23. J Mol Biol 382, 1144-1156.

Bien, M., Longen, S., Wagener, N., Chwalla, I., Herrmann, J. M., and Riemer, J. (2010). Mitochondrial disulfide bond formation is driven by intersubunit electron transfer in Erv1 and proofread by glutathione. Mol Cell 37, 516-528.

Bihlmaier, K., Mesecke, N., Terziyska, N., Bien, M., Hell, K., and Herrmann, J. M. (2007). The disulfide relay system of mitochondria is connected to the respiratory chain. J Cell Biol 179, 389-395.

Cassidy-Stone, A., Chipuk, J. E., Ingerman, E., Song, C., Yoo, C., Kuwana, T., Kurth, M. J., Shaw, J. T., Hinshaw, J. E., Green, D. R., et al. (2008). Chemical inhibition of the mitochondrial division dynamin reveals its role in Bax/Bak-dependent mitochondrial outer membrane permeabilization. Dev Cell 14, 193-204.

Castellano, S., Fiji, H. D., Kinderman, S. S., Watanabe, M., Leon, P., Tamanoi, F., and Kwon, O. (2007). Small-molecule inhibitors of protein geranylgeranyltransferase type I. J Am Chem Soc 129, 5843-5845.

Cavallaro, G. (2010). Genome-wide analysis of eukaryotic twin CX9C proteins. Mol Biosyst 6, 2459-2470.

Chacinska, A., Guiard, B., Muller, J. M., Schulze-Specking, A., Gabriel, K., Kutik, S., and Pfanner, N. (2008). Mitochondrial biogenesis, switching the sorting pathway of the intermembrane space receptor Mia40. J Biol Chem 283, 29723-29729.

Chacinska, A., Koehler, C. M., Milenkovic, D., Lithgow, T., and Pfanner, N. (2009). Importing mitochondrial proteins: machineries and mechanisms. Cell 138, 628-644.

Chacinska, A., Pfannschmidt, S., Wiedemann, N., Kozjak, V., Sanjuan Szklarz, L. K., Schulze-Specking, A., Truscott, K. N., Guiard, B., Meisinger, C., and Pfanner, N. (2004). Essential role of Mia40 in import and assembly of mitochondrial intermembrane space proteins. EMBO J 23, 3735-3746.

Claypool, S. M., Boontheung, P., McCaffery, J. M., Loo, J. A., and Koehler, C. M. (2008a). The cardiolipin transacylase, tafazzin, associates with two distinct respiratory components providing insight into Barth syndrome. Mol Biol Cell 19, 5143-5155.

Claypool, S. M., Oktay, Y., Boontheung, P., Loo, J. A., and Koehler, C. M. (2008b). Cardiolipin defines the interactome of the major ADP/ATP carrier protein of the mitochondrial inner membrane. J Cell Biol 182, 937-950.

Crugeiras, J., Rios, A., Riveiros, E., and Richard, J. P. (2009). Substituent effects on the thermodynamic stability of imines formed from glycine and aromatic aldehydes: implications for the catalytic activity of pyridoxal-5'-phosphate. J Am Chem Soc 131, 15815-15824.

Curado, S., Ober, E. A., Walsh, S., Cortes-Hernandez, P., Verkade, H., Koehler, C. M., and Stainier, D. Y. (2010). The mitochondrial import gene tomm22 is specifically required for hepatocyte survival and provides a liver regeneration model. Dis Model Mech 3, 486-495.

Curran, S. P., Leuenberger, D., Leverich, E. P., Hwang, D. K., Beverly, K. N., and Koehler, C. M. (2004). The role of Hot13p and redox chemistry in the mitochondrial TIM22 import pathway. J Biol Chem 279, 43744-43751.

Curran, S. P., Leuenberger, D., Oppliger, W., and Koehler, C. M. (2002). The Tim9p-Tim10p complex binds to the transmembrane domains of the ADP-ATP carrier. EMBO J 21, 942-953.

Dabir, D. V., Leverich, E. P., Kim, S. K., Tsai, F. D., Hirasawa, M., Knaff, D. B., and Koehler, C. M. (2007). A role for cytochrome c and cytochrome c peroxidase in electron shuttling from Erv1. EMBO J 26, 4801-4811.

Daithankar, V. N., Schaefer, S. A., Dong, M., Bahnson, B. J., and Thorpe, C. (2010). Structure of the human sulfhydryl oxidase augmenter of liver regeneration and characterization of a human mutation causing an autosomal recessive myopathy. Biochemistry 49, 6737-6745.

Deponte, M., and Hell, K. (2009). Disulphide bond formation in the intermembrane space of mitochondria. J Biochem 146, 599-608.

Di Fonzo, A., Ronchi, D., Lodi, T., Fassone, E., Tigano, M., Lamperti, C., Corti, S., Bordoni, A., Fortunato, F., Nizzardo, M., et al. (2009). The mitochondrial disulfide relay system protein GFER is mutated in autosomal-recessive myopathy with cataract and combined respiratory-chain deficiency. Am J Hum Genet 84, 594-604.

Doom, J. A., and Petersen, D. R. (2003). Covalent adduction of nucleophilic amino acids by 4-hydroxynonenal and 4-oxononenal. Chem Biol Interact 143-144, 93-100.

Duncan, M. C., Ho, D. G., Huang, J., Jung, M. E., and Payne, G. S. (2007). Composite synthetic lethal identification of membrane traffic inhibitors. Proc Natl Acad Sci USA 104, 6235-6240.

Farrell, S. R., and Thorpe, C. (2005). Augmenter of liver regeneration: a flavin-dependent sulfhydryl oxidase with cytochrome c reductase activity. Biochemistry 44, 1532-1541.

Gerber, J., Muhlenhoff, U., Hofhaus, G., Lill, R., and Lisowsky, T. (2001). Yeast ERV2p is the first microsomal FAD-linked sulfhydryl oxidase of the Erv1p/Alrp protein family. J Biol Chem 276, 23486-23491.

Glick, B. S., and Pon, L. A. (1995). Isolation of highly purified mitochondria from Saccharomyces cerevisiae. Methods Enzymol 260, 213-223.

Gross, E., Sevier, C. S., Vala, A., Kaiser, C. A., and Fass, D. (2002). A new FAD-binding fold and intersubunit disulfide shuttle in the thiol oxidase Erv2p. Nat Struct Biol 9, 61-67.

Hasson, S. A., Damoiseaux, R., Glavin, J. D., Dabir, D. V., Walker, S. S., and Koehler, C. M. (2010). Substrate specificity of the TIM22 mitochondrial import pathway revealed with small molecule inhibitor of protein translocation. Proc Natl Acad Sci USA 107, 9578-9583.

Herrmann, J. M., and Hell, K. (2005). Chopped, trapped or tacked—protein translocation into the IMS of mitochondria. Trends Biochem Sci 30, 205-211.

Hofmann, S., Rothbauer, U., Muhlenbein, N., Baiker, K., Hell, K., and Bauer, M. F. (2005). Functional and mutational characterization of human MIA40 acting during import into the mitochondrial intermembrane space. J Mol Biol 353, 517-528.

Horn, D., Al-Ali, H., and Barrientos, A. (2008). Cmc1p is a conserved mitochondrial twin CX9C protein involved in cytochrome c oxidase biogenesis. Mol Cell Biol 28, 4354-4364.

Ivanova, N. B., Dimos, J. T., Schaniel, C., Hackney, J. A., Moore, K. A., and Lemischka, I. R. (2002). A stem cell molecular signature. Science 298, 601-604.

Kirdant, A. S., Shelke, V. A., Shankarwar, S. G., Shankarwar, A. G., and Chondhekar, T. K. (2011). Kinetic study of hydrolysis of N-salicylidene-m-methyl aniline spectrophotometrically. J Chem Pharm Res 3, 790-796.

Koehler, C. M., Jarosch, E., Tokatlidis, K., Schmid, K., Schweyen, R. J., and Schatz, G. (1998a). Import of mitochondrial carriers mediated by essential proteins of the intermembrane space. Science 279, 369-373.

Koehler, C. M., Merchant, S., Oppliger, W., Schmid, K., Jarosch, E., Dolfini, L., Junne, T., Schatz, G., and Tokatlidis, K. (1998b). Tim9p, an essential partner subunit of Tim10p for the import of mitochondrial carrier proteins. EMBO J 17, 6477-6486.

Koehler, C. M., and Tienson, H. L. (2009). Redox regulation of protein folding in the mitochondrial intermembrane space. Biochim Biophys Acta 1793, 139-145.

Lange, H., Lisowsky, T., Gerber, J., Muhlenhoff, U., Kispal, G., and Lill, R. (2001). An essential function of the mitochondrial sulfhydryl oxidase Erv1p/ALR in the maturation of cytosolic Fe/S proteins. EMBO Rep 2, 715-720.

Lumsden, A. L., Henshall, T. L., Dayan, S., Lardelli, M. T., and Richards, R. I. (2007). Huntingtin-deficient zebrafish exhibit defects in iron utilization and development. Hum Mol Genet 16, 1905-1920.

Mendelsohn, B. A., Yin, C., Johnson, S. L., Wilm, T. P., Solnica-Krezel, L., and Gitlin, J. D. (2006). Atp7a determines a hierarchy of copper metabolism essential for notochord development. Cell Metab 4, 155-162.

Milenkovic, D., Ramming, T., Muller, J. M., Wenz, L. S., Gebert, N., Schulze-Specking, A., Stojanovski, D., Rospert, S., and Chacinska, A. (2009). Identification of the signal directing Tim9 and Tim10 into the intermembrane space of mitochondria. Mol Biol Cell 20, 2530-2539.

Mochizuki, Y., and Furukawa, K. (1987). Application of coomassie brilliant blue staining to cultured hepatocytes. Cell Biol Int Rep 11, 367-371.

Mokranjac, D., and Neupert, W. (2009). Thirty years of protein translocation into mitochondria: unexpectedly complex and still puzzling. Biochim Biophys Acta 1793, 33-41.

Murphey, R D., and Zon, L. I. (2006). Small molecule screening in the zebrafish. Methods 39, 255-261.

Nordfelth, R., Kauppi, A. M., Norberg, H. A., Wolf-Watz, H., and Elofsson, M. (2005). Small-molecule inhibitors specifically targeting type III secretion. Infect Immun 73, 3104-3114.

Parone, P. A., James, D. I., Da Cruz, S., Mattenberger, Y., Donze, O., Barja, F., and Martinou, J. C. (2006). Inhibiting the mitochondrial fission machinery does not prevent Bax/Bak-dependent apoptosis. Mol Cell Biol 26, 7397-7408.

Ramalho-Santos, M., Yoon, S., Matsuzaki, Y., Mulligan, R. C., and Melton, D. A. (2002). "Stemness": transcriptional profiling of embryonic and adult stem cells. Science 298, 597-600.

Riemer, J., Fischer, M., and Herrmann, J. M. (2011). Oxidation-driven protein import into mitochondria: Insights and blind spots. Biochim Biophys Acta 1808, 981-989.

Ryan, M. T., Müller, H., and Pfanner, N. (1999). Functional Staging of ADP/ATP Carrier Translocation across the Outer Mitochondrial Membrane. J Biol Chem 274, 20619-20627.

Schmidt, O., Pfanner, N., and Meisinger, C. (2010). Mitochondrial protein import: from proteomics to functional mechanisms. Nat Rev Mol Cell Biol 11, 655-667.

Scorrano, L., Ashiya, M., Buttle, K., Weiler, S., Oakes, S. A., Mannella, C. A., and Korsmeyer, S. J. (2002). A distinct pathway remodels mitochondrial cristae and mobilizes cytochrome c during apoptosis. Dev Cell 2, 55-67.

Senkevich, T. G., White, C. L., Koonin, E. V., and Moss, B. (2002). Complete pathway for protein disulfide bond formation encoded by poxviruses. Proc Natl Acad Sci USA 99, 6667-6672.

Shamblott, M. J., Axelman, J., Wang, S., Bugg, E. M., Littlefield, J. W., Donovan, P. J., Blumenthal, P. D., Huggins, G. R., and Gearhart, J. D. (1998). Derivation of pluripotent stem cells from cultured human primordial germ cells. Proc Natl Acad Sci USA 95, 13726-13731.

Shaw, G. C., Cope, J. J., Li, L., Corson, K., Hersey, C., Ackermann, G. E., Gwynn, B., Lambert, A. J., Wingert, R. A., Traver, D., et al. (2006). Mitoferrin is essential for erythroid iron assimilation. Nature 440, 96-100.

Shu, X., Huang, J., Dong, Y., Choi, J., Langenbacher, A., and Chen, J. N. (2007). Na,K-ATPase alpha2 and Ncx4a regulate zebrafish left-right patterning. Development 134, 1921-1930.

Sideris, D. P., Petrakis, N., Katrakili, N., Mikropoulou, D., Gallo, A., Ciofi-Baffoni, S., Banci, L., Bertini, I., and Tokatlidis, K. (2009). A novel intermembrane space-targeting signal docks cysteines onto Mia40 during mitochondrial oxidative folding. J Cell Biol 187, 1007-1022.

Sideris, D. P., and Tokatlidis, K. (2010). Oxidative protein folding in the mitochondrial intermembrane space. Antioxid Redox Signal 13, 1189-1204.

Stojanovski, D., Milenkovic, D., Muller, J. M., Gabriel, K., Schulze-Specking, A., Baker, M. J., Ryan, M. T., Guiard, B., Pfanner, N., and Chacinska, A. (2008a). Mitochondrial protein import: precursor oxidation in a ternary complex with disulfide carrier and sulfhydryl oxidase. J Cell Biol 183, 195-202.

Stojanovski, D., Muller, J. M., Milenkovic, D., Guiard, B., Pfanner, N., and Chacinska, A. (2008b). The MIA system for protein import into the mitochondrial intermembrane space. Biochim Biophys Acta 1783, 610-617.

Terziyska, N., Grumbt, B., Bien, M., Neupert, W., Herrmann, J. M., and Hell, K. (2007). The sulfhydryl oxidase Erv1 is a substrate of the Mia40-dependent protein translocation pathway. FEBS Lett 581, 1098-1102.

Terziyska, N., Grumbt, B., Kozany, C., and Hell, K. (2009). Structural and functional roles of the conserved cysteine residues of the redox-regulated import receptor Mia40 in the intermembrane space of mitochondria. J Biol Chem 284, 1353-1363.

Thorpe, C., Hoober, K. L., Raje, S., Glynn, N. M., Burnside, J., Turi, G. K., and Coppock, D. L. (2002). Sulfhydryl oxidases: emerging catalysts of protein disulfide bond formation in eukaryotes. Arch Biochem Biophys 405, 1-12.

Tienson, H. L., Dabir, D. V., Neal, S. E., Loo, R., Hasson, S. A., Boontheung, P., Kim, S. K., Loo, J. A., and Koehler, C. M. (2009). Reconstitution of the Mia40-Erv1 oxidative folding pathway for the small tim proteins. Mol Biol Cell 20, 3481-3490.

Todd, L. R., Damin, M. N., Gomathinayagam, R., Horn, S. R., Means, A. R., and Sankar, U. (2010a). Growth factor erv1-like modulates Drp1 to preserve mitochondrial dynamics and function in mouse embryonic stem cells. Mol Biol Cell 21, 1225-1236.

Todd, L. R., Gomathinayagam, R., and Sankar, U. (2010b). A novel Gfer-Drp1 link in preserving mitochondrial dynamics and function in pluripotent stem cells. Autophagy 6, 821-822.

Truscott, K. N., Wiedemann, N., Rehling, P., Muller, H., Meisinger, C., Pfanner, N., and Guiard, B. (2002). Mitochondrial import of the ADP/ATP carrier: the essential TIM complex of the intermembrane space is required for precursor release from the TOM complex. Mol Cell Biol 22, 7780-7789.

Vitu, E., Bentzur, M., Lisowsky, T., Kaiser, C. A., and Fass, D. (2006). Gain of function in an ERV/ALR sulfhydryl oxidase by molecular engineering of the shuttle disulfide. J Mol Biol 362, 89-101.

Waterhouse, N. J., Goldstein, J. C., Kluck, R. M., Newmeyer, D. D., and Green, D. R. (2001). The (Holey) study of mitochondria in apoptosis. Methods Cell Biol 66, 365-391.

Webb, T. R. (2005). Current directions in the evolution of compound libraries. Curr Opin Drug Discov Devel 8, 303-308.

Wingert, R. A., Galloway, J. L., Barut, B., Foott, H., Fraenkel, P., Axe, J. L., Weber, G. J., Dooley, K., Davidson, A. J., Schmid, B., et al. (2005). Deficiency of glutaredoxin 5 reveals Fe—S clusters are required for vertebrate haem synthesis. Nature 436, 1035-1039.

Wu, C. K., Dailey, T. A., Dailey, H. A., Wang, B. C., and Rose, J. P. (2003). The crystal structure of augmenter of liver regeneration: A mammalian FAD-dependent sulfhydryl oxidase. Protein Sci 12, 1109-1118.

Zhang, J., Khvorostov, I., Hong, J. S., Oktay, Y., Vergnes, L., Nuebel, E., Wahjudi, P. N., Setoguchi, K., Wang, G., Do, A., et al. (2011). UCP2 regulates energy metabolism and differentiation potential of human pluripotent stem cells. EMBO J 30, 4860-4873.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention.

We claim:

1. A mitochondrial protein translation inhibitor, wherein the inhibitor is MitoBlock-6:

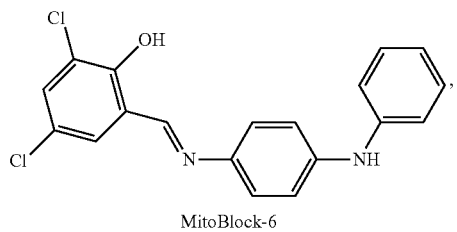

MitoBlock-6 derivatives thereof, or pharmaceutically acceptable salts thereof.

2. A composition comprising a mitochondrial protein translation inhibitor, wherein the inhibitor is MitoBlock-6:

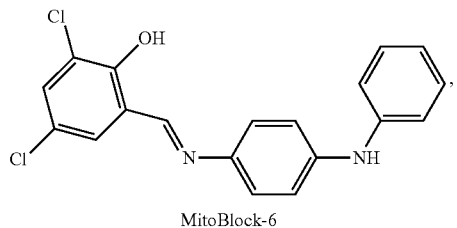

MitoBlock-6 derivatives thereof, or pharmaceutically acceptable salts thereof.

3. The composition of claim 2, further comprising a carrier.

4. A method comprising modulating the assembly or the function of mitochondria by applying to a body of mitochondria or a cell the mitochondrial translocation inhibitor of claim 1.

5. The method of claim 4, wherein the specific inhibitor is included in a composition.

6. The method of claim 5, wherein the composition further comprises a carrier.

7. A method of treating or ameliorating a disorder, comprising administering to a patient in need thereof the mitochondrial translocation inhibitor of claim 1.

8. The method of claim 7, wherein the specific inhibitor is included in a composition.

9. The method of claim 8, wherein the composition further comprises a carrier.

10. The method of claim 7, wherein the disorder is a disease of deafness-dystonia syndrome, cancer, Parkinson's disease, or Alzheimer's disease.

* * * * *